United States Patent
Osaka et al.

(10) Patent No.: US 9,067,916 B2
(45) Date of Patent: *Jun. 30, 2015

(54) HETEROCYCLIC COMPOUND

(75) Inventors: Harue Osaka, Kanagawa (JP); Satoko Shitagaki, Kanagawa (JP); Yasushi Kitano, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 70 days.

This patent is subject to a terminal disclaimer.

(21) Appl. No.: 13/360,066

(22) Filed: Jan. 27, 2012

(65) Prior Publication Data

US 2012/0197020 A1 Aug. 2, 2012

(30) Foreign Application Priority Data

Feb. 1, 2011 (JP) .................................. 2011-020124
Aug. 23, 2011 (JP) .................................. 2011-181469

(51) Int. Cl.
| C07D 241/38 | (2006.01) |
| C07D 403/10 | (2006.01) |
| C07D 405/10 | (2006.01) |
| C07D 409/10 | (2006.01) |

(Continued)

(52) U.S. Cl.
CPC ............ *C07D 403/10* (2013.01); *C07D 405/10* (2013.01); *C07D 409/10* (2013.01); *H01L 51/0059* (2013.01); *H01L 51/0072* (2013.01); *H01L 51/0074* (2013.01); *H01L 51/0085* (2013.01); *H01L 51/5016* (2013.01); *H01L 2251/5384* (2013.01)

(58) Field of Classification Search
CPC .... C09B 17/04; C07D 471/14; C07D 471/04; C07D 241/38; C07D 487/04
See application file for complete search history.

(56) References Cited

U.S. PATENT DOCUMENTS

| 6,723,445 B2 | 4/2004 | Li et al. |
| 7,355,340 B2 | 4/2008 | Shitagaki et al. |

(Continued)

FOREIGN PATENT DOCUMENTS

| CN | 101203968 A | 6/2008 |
| CN | 101853923 A | 10/2010 |

(Continued)

OTHER PUBLICATIONS

English Translation of KR 2011042004 A to Je et al, published Apr. 22, 2011.*

(Continued)

*Primary Examiner* — San-Ming Hui
*Assistant Examiner* — Andrew Lee
(74) *Attorney, Agent, or Firm* — Fish & Richardson P.C.

(57) ABSTRACT

Provided is a novel heterocyclic compound which can be used for a light-emitting element, as a host material of a light-emitting layer in which a light-emitting substance is dispersed. A heterocyclic compound represented by a general formula (G1) is provided. In the formula, A represents any of a substituted or unsubstituted dibenzothiophenyl group, a substituted or unsubstituted dibenzofuranyl group, and a substituted or unsubstituted carbazolyl group, $R^{11}$ to $R^{19}$ separately represent any of hydrogen, an alkyl group having 1 to 4 carbon atoms, and a substituted or unsubstituted aryl group having 6 to 14 carbon atoms, and Ar represents a substituted or unsubstituted arylene group having 6 to 13 carbon atoms.

23 Claims, 20 Drawing Sheets

(51) Int. Cl.
　　　*H01L 51/00*　　　(2006.01)
　　　*H01L 51/50*　　　(2006.01)

(56) References Cited

U.S. PATENT DOCUMENTS

| | | | |
|---|---|---|---|
| 7,601,435 | B2 | 10/2009 | Shitagaki et al. |
| 7,927,720 | B2 | 4/2011 | Nomura et al. |
| 7,931,974 | B2 | 4/2011 | Egawa et al. |
| 8,084,146 | B2 | 12/2011 | Murase et al. |
| 8,119,259 | B2 | 2/2012 | Kadoma et al. |
| 8,138,303 | B2 | 3/2012 | Chebotareva et al. |
| 8,178,216 | B2 | 5/2012 | Nomura et al. |
| 8,231,984 | B2 | 7/2012 | Shitagaki et al. |
| 8,252,433 | B2 | 8/2012 | Egawa et al. |
| 8,314,101 | B2 | 11/2012 | Kadoma et al. |
| 2009/0026922 | A1 | 1/2009 | Iwaki et al. |
| 2009/0072718 | A1 | 3/2009 | Nomura et al. |
| 2009/0140641 | A1 | 6/2009 | Nomura et al. |
| 2009/0140642 | A1 | 6/2009 | Kadoma et al. |
| 2009/0153041 | A1 | 6/2009 | Kawakami et al. |
| 2009/0184633 | A1 | 7/2009 | Kadoma et al. |
| 2009/0203704 | A1 | 8/2009 | Kadoma et al. |
| 2010/0039024 | A1 | 2/2010 | Wendeborn et al. |
| 2010/0090588 | A1 | 4/2010 | Yokoyama et al. |
| 2010/0249349 | A1 | 9/2010 | Chebotareva et al. |
| 2011/0089407 | A1 | 4/2011 | Schmidhalter et al. |
| 2011/0210316 | A1 | 9/2011 | Kadoma et al. |
| 2012/0138907 | A1 | 6/2012 | Murase et al. |
| 2012/0193613 | A1 | 8/2012 | Kadoma et al. |
| 2012/0286257 | A1 | 11/2012 | Shitagaki et al. |
| 2012/0313506 | A1 | 12/2012 | Egawa et al. |

FOREIGN PATENT DOCUMENTS

| | | | |
|---|---|---|---|
| CN | 101867019 A | | 10/2010 |
| CN | 101970448 A | | 2/2011 |
| EP | 1 616 864 A1 | | 1/2006 |
| EP | 1 748 045 A1 | | 1/2007 |
| EP | 1 962 354 A1 | | 8/2008 |
| EP | 2 055 704 A1 | | 5/2009 |
| EP | 2 065 378 A1 | | 6/2009 |
| EP | 2 236 506 A1 | | 10/2010 |
| EP | 2 363 398 A1 | | 9/2011 |
| EP | 2 450 356 A1 | | 5/2012 |
| JP | 2006-324650 A | | 11/2006 |
| JP | 2007-189001 A | | 7/2007 |
| JP | 2008-106051 A | | 5/2008 |
| JP | 2008-239613 A | | 10/2008 |
| JP | 2009-149629 A | | 7/2009 |
| JP | 2009-149631 A | | 7/2009 |
| JP | 2009-149632 A | | 7/2009 |
| JP | 2009-526111 A | | 7/2009 |
| JP | 2011-511821 A | | 4/2011 |
| KR | 2008-0005441 A | | 1/2008 |
| KR | 2010-0123716 A | | 11/2010 |
| KR | 2011-0042004 A | | 4/2011 |
| KR | 2011042004 A | * | 4/2011 |
| TW | 200940554 A1 | | 10/2009 |
| WO | 2003/058667 A1 | | 7/2003 |
| WO | 2004/043937 A1 | | 5/2004 |
| WO | 2004/094389 A1 | | 11/2004 |
| WO | 2005/113531 A1 | | 12/2005 |
| WO | 2006/115232 A1 | | 11/2006 |
| WO | 2007/069569 A1 | | 6/2007 |
| WO | 2007/090773 A1 | | 8/2007 |
| WO | 2008-023628 A1 | | 2/2008 |
| WO | 2008/031743 A1 | | 3/2008 |
| WO | 2009/100991 A1 | | 8/2009 |

OTHER PUBLICATIONS

Wermuth, Molecular Variations Based on Isosteric Replacements, The Practice of Medicinal Chemistry, 1996, pp. 204-237.*
European Search Report (EP Application No. 11155124.8) dated Jun. 24, 2011, 7 pages.
Christian Goldsmith et al.; "C—H Bond Activation by a Ferric Methoxide Complex: Modeling the Rate-Determining Step in the Mechanism of Lipoxygenase"; J. Am. Chem. Soc. (Journal of the American Chemical Society); 2002; pp. 83-96; vol. 124, No. 1.
Toshihiro Ohnishi et al.; "A Method Measuring An Energy Level"; High Molecular EL materials—development of light-emitting high molecular compounds-; Dec. 25, 2004; pp. 64-67; Kyoritsu Shuppan; with English translation.
Ming Zhang et al.; "Highly-efficient solution-processed OLEDs on new bipolar emitters"; Chemical Communications; 2010; pp. 3923-3925; vol. 46.

* cited by examiner

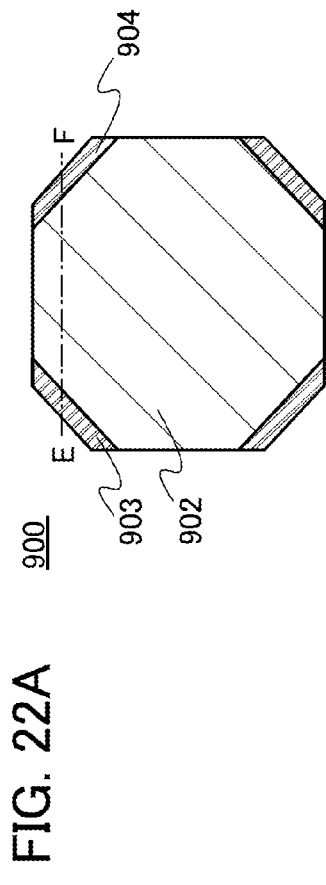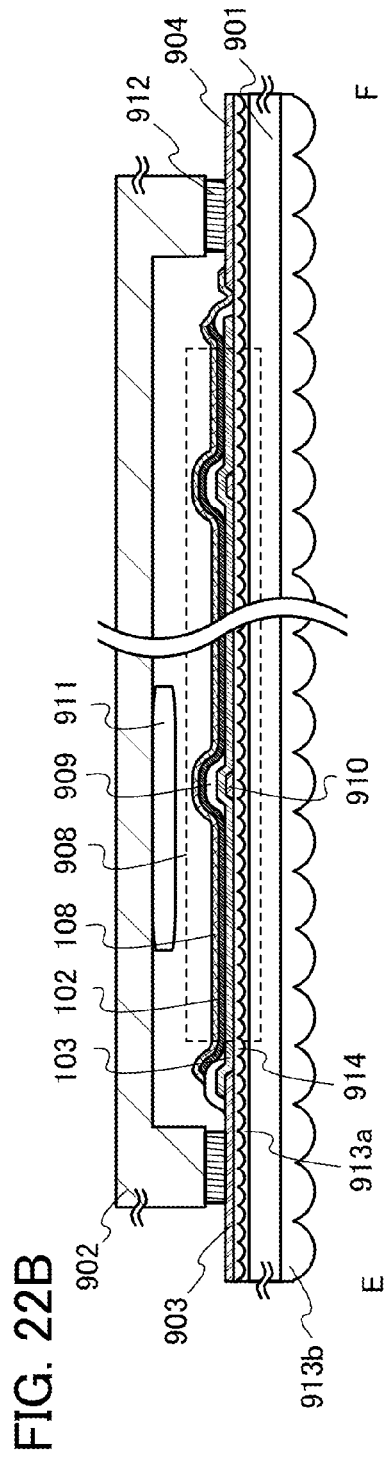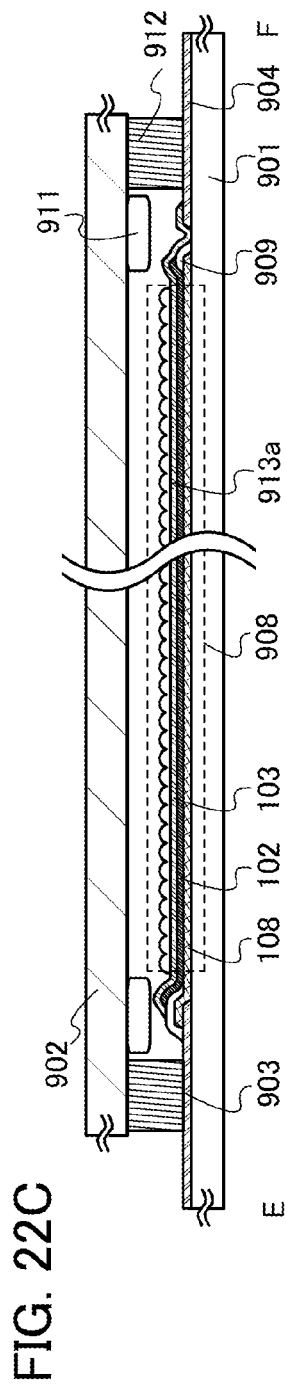

HETEROCYCLIC COMPOUND

BACKGROUND OF THE INVENTION

1. Field of the Invention

The present invention relates to a heterocyclic compound. In particular, the present invention relates to a heterocyclic compound that can be used for a light-emitting element utilizing organic electroluminescence (EL).

2. Description of the Related Art

In recent years, research and development have been extensively conducted on light-emitting elements utilizing EL. In the basic structure of such a light-emitting element, a layer containing a light-emitting substance is interposed between a pair of electrodes. By application of a voltage to this element, light emission from the light-emitting substance can be obtained.

Since such light-emitting elements are of a self-light-emitting type, it is considered that they have advantages over liquid crystal displays that the visibility of pixels is high, backlights are not required, and so on, and therefore the light-emitting elements are suitable as flat panel display elements. The light-emitting elements also have a great advantage that they can be manufactured as thin and lightweight elements. Further, very high-speed response is also one of the features of such elements.

Furthermore, since such light-emitting elements can be formed in a film form, they make it possible to provide planar light emission. Therefore, large-area elements utilizing planar light emission can be easily formed. This feature is difficult to obtain with point light sources typified by incandescent lamps and LEDs or linear light sources typified by fluorescent lamps. Thus, light-emitting elements also have great potential as planar light sources applicable to lighting devices and the like.

Such light-emitting elements utilizing electroluminescence can be broadly classified according to whether the light-emitting substance is an organic compound or an inorganic compound. In the case of an organic EL element in which a layer containing an organic compound used as the light-emitting substance is provided between a pair of electrodes, application of a voltage to the light-emitting element causes electron injection from a cathode and hole injection from an anode into the layer containing the organic compound having a light-emitting property and thus current flows. The injected electrons and holes then lead the organic compound to its excited state, so that light emission is obtained from the excited organic compound.

The excited state formed by an organic compound can be a singlet excited state or a triplet excited state. Light emission from the singlet excited state (S*) is called fluorescence, and emission from the triplet excited state (T*) is called phosphorescence. In addition, the statistical generation ratio thereof in a light-emitting element is considered as follows: S*:T*=1:3.

At room temperature, an observation on a compound that can convert energy of a singlet excited state into light emission (hereinafter, referred to as a fluorescent compound) usually shows only light emission from the singlet excited state (fluorescence) without light emission from the triplet excited state (phosphorescence). Therefore the internal quantum efficiency (the ratio of generated photons to injected carriers) of a light-emitting element using a fluorescent compound is assumed to have a theoretical limit of 25% based on a S*-to-T* ratio of 1:3.

In contrast, an observation on a compound that can convert energy of a triplet excited state into light emission (hereinafter, called a phosphorescent compound) shows light emission from the triplet excited state (phosphorescence). Further, since intersystem crossing (i.e., transition from a singlet excited state to a triplet excited state) easily occurs in a phosphorescent compound, the internal quantum efficiency can be theoretically increased to 100%. That is, higher emission efficiency can be obtained than using a fluorescent compound. For this reason, light-emitting elements using a phosphorescent compound have been under active development recently in order that highly efficient light-emitting elements can be realized.

When formed using the above-described phosphorescent compound, a light-emitting layer of a light-emitting element is often formed such that the phosphorescent compound is dispersed in a matrix containing another compound in order to suppress concentration quenching or quenching due to triplet-triplet annihilation in the phosphorescent compound. Here, the compound as the matrix is called a host material, and the compound dispersed in the matrix, such as a phosphorescent compound, is called a guest material.

In the case where a phosphorescent compound is a guest material, a host material needs to have higher triplet excitation energy (energy difference between a ground state and a triplet excited state) than the phosphorescent compound.

Furthermore, since singlet excitation energy (energy difference between a ground state and a singlet excited state) is higher than triplet excitation energy, a substance that has high triplet excitation energy also has high singlet excitation energy. Therefore the above substance that has high triplet excitation energy is also effective in a light-emitting element using a fluorescent compound as a light-emitting substance.

Studies have been conducted on compounds having dibenzo[f,h]quinoxaline rings, which are examples of the host material used when a phosphorescent compound is a guest material (e.g., see Patent Documents 1 and 2).

REFERENCE

Patent Document

[Patent Document 1] International Publication WO 03/058667 pamphlet
[Patent Document 2] Japanese Published Patent Application No. 2007-189001

SUMMARY OF THE INVENTION

However, the above compounds having dibenzo[f,h]quinoxaline rings have a planar structure, and accordingly, these compounds are easily crystallized. A light-emitting element using a compound that is easy to crystallize has a short lifetime. Further, if another skeleton is directly bonded to the dibenzo[f,h]quinoxaline ring so that the compound has a sterically bulky structure, the conjugated system could possibly extend to cause a decrease in triplet excitation energy.

Further, in order to realize a light-emitting device, an electronic device, and a lighting device each having reduced power consumption and high reliability, a light-emitting element having low driving voltage, a light-emitting element having high current efficiency, or a light-emitting element having a long lifetime have been expected.

Therefore, an object of one embodiment of the present invention is to provide a novel heterocyclic compound which can be used for a light-emitting element, as a host material of a light-emitting layer in which a light-emitting substance is dispersed, in particular, a novel heterocyclic compound which can be suitably used as a host material in which a phosphorescent compound is used as a light-emitting substance.

Another object of one embodiment of the present invention is to provide a light-emitting element having low driving voltage. Yet another object of one embodiment of the present invention is to provide a light-emitting element having high current efficiency. Another object of one embodiment of the present invention is to provide a light-emitting element having a long lifetime. Still another object of one embodiment of the present invention is to provide a light-emitting device, an electronic device, and a lighting device each having reduced power consumption by using the above light-emitting element.

Note that an object of the invention to be disclosed below is to achieve at least one of the above-described objects.

A compound with a quinoxaline skeleton has a high electron-transport property, and the use of such a compound for a light-emitting element enables the element to have low driving voltage. However, a quinoxaline skeleton has a planar structure. Since a compound having a planar structure is easily crystallized when a film is formed using the compound, the use of such a compound for light-emitting elements causes the elements to have a short lifetime. Furthermore, a quinoxaline skeleton is poor at accepting holes. When a compound that cannot easily accept holes is used as a host material of a light-emitting layer, the region of electron-hole recombination concentrates on an interface of the light-emitting layer, leading to a reduction in the lifetime of the light-emitting element. It is likely that these problems will be solved by introduction of a hole-transport skeleton into the molecule. However, if a hole-transport skeleton is directly bonded to a quinoxaline skeleton, the conjugated system extends to cause a decrease in band gap and a decrease in triplet excitation energy.

Nevertheless, the present inventors have found that the above problems can be solved by using, for a light-emitting element, a compound in which a dibenzo[f,h]quinoxaline ring and a hole-transport skeleton are bonded through an arylene group.

As the compound in which a dibenzo[f,h]quinoxaline ring and a hole-transport skeleton are bonded through an arylene group, a heterocyclic compound below can be given.

One embodiment of the present invention is a heterocyclic compound represented by a general formula (G1) below.

[Chemical Formula 1]

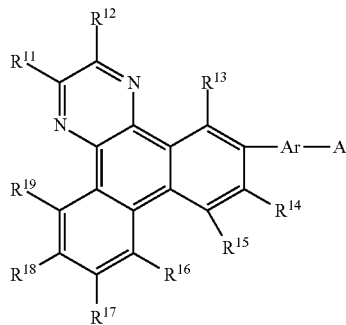

(G1)

In the formula, A represents any of a substituted or unsubstituted dibenzothiophenyl group, a substituted or unsubstituted dibenzofuranyl group, and a substituted or unsubstituted carbazolyl group, $R^{11}$ to $R^{19}$ separately represent any of hydrogen, an alkyl group having 1 to 4 carbon atoms, and a substituted or unsubstituted aryl group having 6 to 14 carbon atoms, and Ar represents a substituted or unsubstituted arylene group having 6 to 13 carbon atoms.

Another embodiment of the present invention is a heterocyclic compound represented by a general formula (G2-1) below.

[Chemical Formula 2]

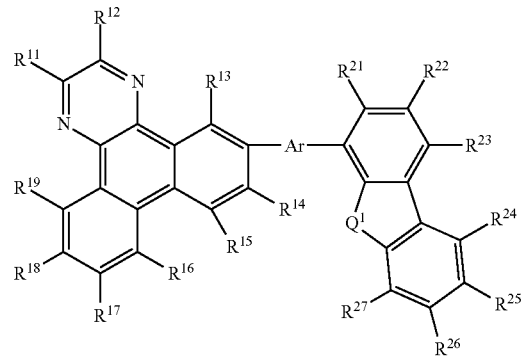

(G2-1)

In the formula, $Q^1$ represents any of an oxygen atom, a sulfur atom, and a nitrogen atom, and the nitrogen atom has an alkyl group having 1 to 4 carbon atoms or a substituted or unsubstituted aryl group having 6 to 13 carbon atoms as a substituent. $R^{11}$ to $R^{19}$ and $R^{21}$ to $R^{27}$ separately represent any of hydrogen, an alkyl group having 1 to 4 carbon atoms, and a substituted or unsubstituted aryl group having 6 to 14 carbon atoms, and Ar represents a substituted or unsubstituted arylene group having 6 to 13 carbon atoms.

Another embodiment of the present invention is a heterocyclic compound represented by a general formula (G2-2) below.

[Chemical Formula 3]

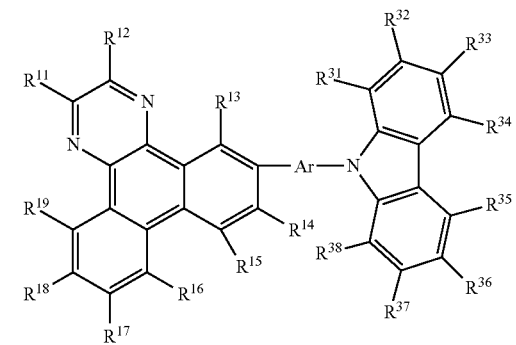

(G2-2)

In the formula, $R^{11}$ to $R^{19}$ and $R^{31}$ to $R^{38}$ separately represent any of hydrogen, an alkyl group having 1 to 4 carbon atoms, and a substituted or unsubstituted aryl group having 6 to 14 carbon atoms, and Ar represents a substituted or unsubstituted arylene group having 6 to 13 carbon atoms.

Another embodiment of the present invention is a heterocyclic compound represented by a general formula (G2-3) below.

[Chemical Formula 4]

(G2-3)

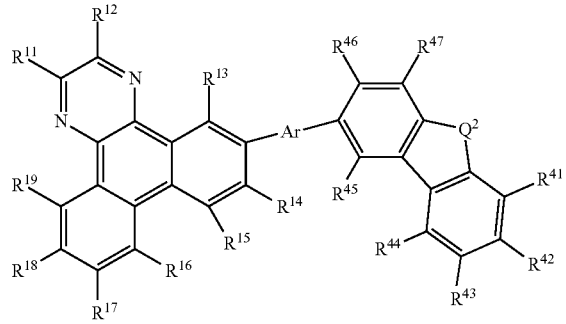

In the formula, $R^{11}$ to $R^{19}$ and $R^{41}$ to $R^{47}$ separately represent any of hydrogen, an alkyl group having 1 to 4 carbon atoms, and a substituted or unsubstituted aryl group having 6 to 14 carbon atoms, Ar represents a substituted or unsubstituted arylene group having 6 to 13 carbon atoms, $Q^2$ represents any of a sulfur atom, an oxygen atom, and a nitrogen atom, and the nitrogen atom has an alkyl group having 1 to 4 carbon atoms or a substituted or unsubstituted aryl group having 6 to 14 carbon atoms as a substituent.

In the general formulae (G1), (G2-1), (G2-2), and (G2-3), Ar is preferably a substituted or unsubstituted phenylene group or a substituted or unsubstituted biphenyldiyl group, particularly a substituted or unsubstituted phenylene group. Furthermore, Ar is much preferably a substituted or unsubstituted m-phenylene group so as to have a high level of triplet excitation energy (T1 level) or a high level of singlet excited energy (S1 level).

Another embodiment of the present invention is a heterocyclic compound represented by a general formula (G3-1) below.

[Chemical Formula 5]

(G3-1)

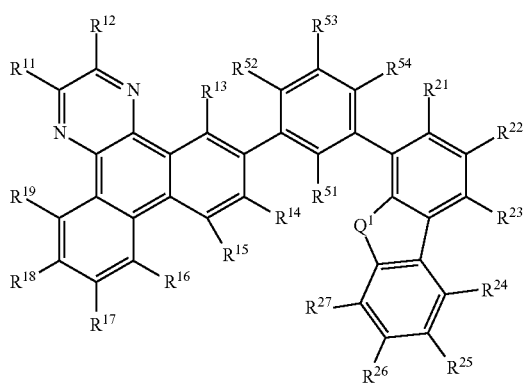

In the formula, $Q^1$ represents any of a sulfur atom, an oxygen atom, and a nitrogen atom, and the nitrogen atom has an alkyl group having 1 to 4 carbon atoms or a substituted or unsubstituted aryl group having 6 to 13 carbon atoms as a substituent. In addition, $R^{11}$ to $R^{19}$, $R^{21}$ to $R^{27}$, and $R^{51}$ to $R^{54}$ separately represent any of hydrogen, an alkyl group having 1 to 4 carbon atoms, and a substituted or unsubstituted aryl group having 6 to 14 carbon atoms.

Yet another embodiment of the present invention is a heterocyclic compound represented by a general formula (G3-2) below.

[Chemical Formula 6]

(G3-2)

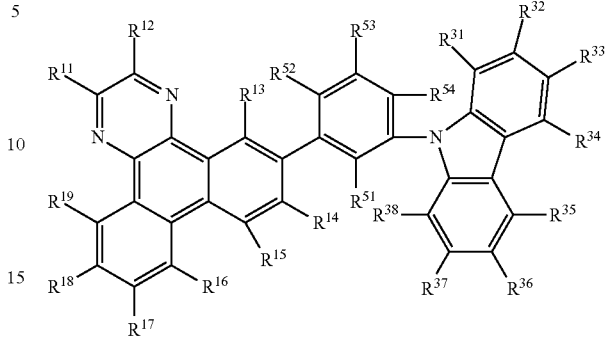

In the formula, $R^{11}$ to $R^{19}$, $R^{31}$ to $R^{38}$, and $R^{51}$ to $R^{54}$ separately represent any of hydrogen, an alkyl group having 1 to 4 carbon atoms, and a substituted or unsubstituted aryl group having 6 to 14 carbon atoms.

Yet another embodiment of the present invention is a heterocyclic compound represented by a general formula (G3-3) below.

[Chemical Formula 7]

(G3-3)

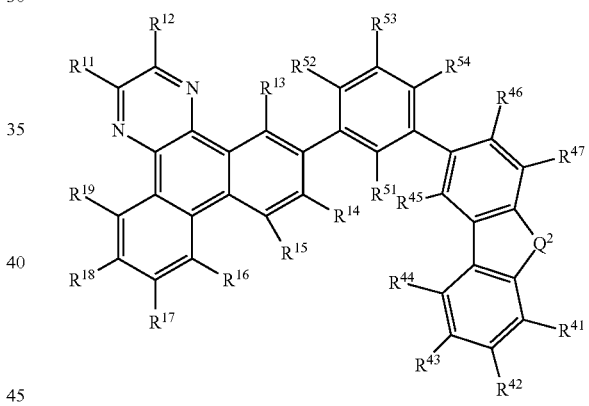

In the formula, $R^{11}$ to $R^{19}$, $R^{41}$ to $R^{47}$, and $R^{51}$ to $R^{54}$ separately represent any of hydrogen, an alkyl group having 1 to 4 carbon atoms, and a substituted or unsubstituted aryl group having 6 to 14 carbon atoms, $Q^2$ represents any of a sulfur atom, an oxygen atom, and a nitrogen atom, and the nitrogen atom has an alkyl group having 1 to 4 carbon atoms or a substituted or unsubstituted aryl group having 6 to 14 carbon atoms as a substituent.

The introduction of a hole-transport skeleton into a dibenzo[f,h]quinoxaline ring enables any of the compounds according to one embodiment of the present invention to have a sterically bulky structure, and the compound is difficult to crystallize when a film is formed using the compound. By the use of the compound for a light-emitting element, the element can have a long lifetime. Moreover, in this compound, since a dibenzo[f,h]quinoxaline ring and a hole-transport skeleton are bonded through an arylene group, decreases in band gap and triplet excitation energy can be prevented as compared with a compound in which a dibenzo[f,h]quinoxaline ring and a hole-transport skeleton are directly bonded. By the use of the compound for a light-emitting element, the element can have high current efficiency.

Thus, any of the compounds according to one embodiment of the present invention can be suitably used as a material for an organic device such as a light-emitting element or an organic transistor.

One embodiment of the present invention is a light-emitting element including the above-described heterocyclic compound.

One embodiment of the present invention is a light-emitting element which includes a light-emitting layer between a pair of electrodes. The light-emitting layer contains a light-emitting substance and the above-described heterocyclic compound.

By the use of any of the heterocyclic compounds according to one embodiment of the present invention, a light-emitting element can have low driving voltage. Further, by the use of any of the heterocyclic compounds according to one embodiment of the present invention, a light-emitting element can have high current efficiency. In addition, by the use of any of the heterocyclic compounds according to one embodiment of the present invention, a light-emitting element can have a long lifetime. Low power consumption can be realized in a light-emitting device (such as an image display device) which includes the above light-emitting element. Thus, one embodiment of the present invention is a light-emitting device including the above light-emitting element. One embodiment of the present invention also includes an electronic device using the light-emitting device in its display portion and a lighting device using the light-emitting device in its light-emitting portion.

The light-emitting device in this specification covers an image display device using a light-emitting element and also the following devices: a module including a light-emitting element to which a connector such as an anisotropic conductive film, a TAB (tape automated bonding) tape, or a TCP (tape carrier package) is attached; a module in which the top of a TAB tape or a TCP is provided with a printed wiring board; a module in which an IC (integrated circuit) is directly mounted on a light-emitting element by a COG (chip on glass) technique; and further a light-emitting device used for a lighting device and the like.

Furthermore, a heterocyclic compound used for the synthesis of any of the heterocyclic compounds according to one embodiment of the present invention is also a novel substance; therefore, this heterocyclic compound is also included in the present invention. Therefore, another embodiment of the present invention is a heterocyclic compound represented by a general formula (G4).

[Chemical Formula 8]

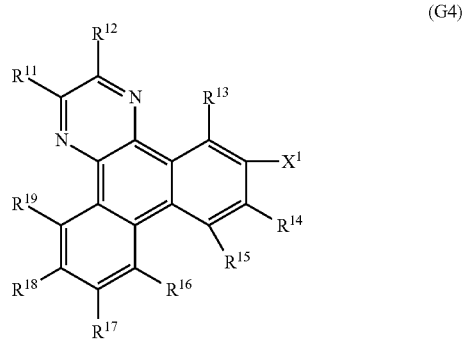

(G4)

In the formula, $R^{11}$ to $R^{19}$ separately represent any of hydrogen, an alkyl group having 1 to 4 carbon atoms, and a substituted or unsubstituted aryl group having 6 to 14 carbon atoms, and $X^1$ represents a halogen.

One embodiment of the present invention can provide a novel heterocyclic compound which can be used for a light-emitting element, as a host material of a light-emitting layer in which a light-emitting substance is dispersed. Another embodiment of the present invention can provide a light-emitting element having low driving voltage. Yet another embodiment of the present invention can provide a light-emitting element having high current efficiency. Still another embodiment of the present invention can provide a light-emitting element having a long lifetime. By using the light-emitting element, another embodiment of the present invention can provide a light-emitting device, an electronic device, and a lighting device each having reduced power consumption.

BRIEF DESCRIPTION OF THE DRAWINGS

In the accompanying drawings:

FIGS. 22A to 22C illustrate light-emitting devices according to one embodiment of the present invention;

DETAILED DESCRIPTION OF THE INVENTION

Figure 1A:
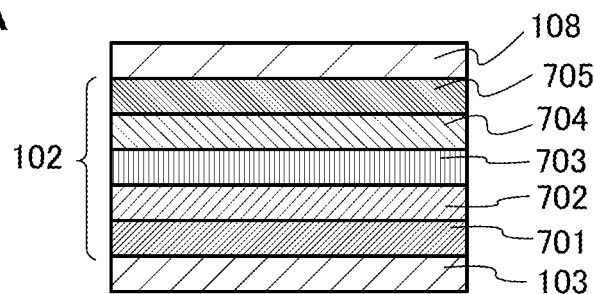
FIGS. 1A to 1C each illustrate a light-emitting element according to one embodiment of the present invention.

Embodiments of the present invention will now be described with reference to the accompanying drawings. Note that the invention is not limited to the description below, and it will be easily understood by those skilled in the art that various changes and modifications can be made without departing from the spirit and scope of the invention. Therefore, the invention should not be construed as being limited to the description in the following embodiments.

Embodiment 1

In Embodiment 1, heterocyclic compounds according to one embodiment of the present invention will be described.

One embodiment of the present invention is the heterocyclic compound represented by the general formula (G1).

[Chemical Formula 9]

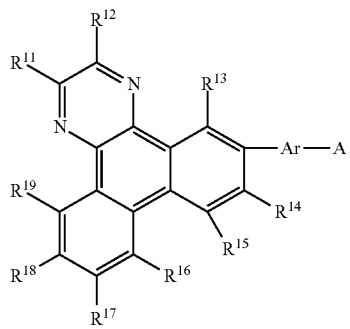

(G1)

In the general formula (G1), A represents any of a substituted or unsubstituted dibenzothiophenyl group, a substituted or unsubstituted dibenzofuranyl group, and a substituted or unsubstituted carbazolyl group, $R^{11}$ to $R^{19}$ separately represent any of hydrogen, an alkyl group having 1 to 4 carbon atoms, and a substituted or unsubstituted aryl group having 6 to 14 carbon atoms, and Ar represents a substituted or unsubstituted arylene group having 6 to 13 carbon atoms.

Another embodiment of the present invention is a heterocyclic compound represented by the general formula (G2-1) below.

[Chemical Formula 10]

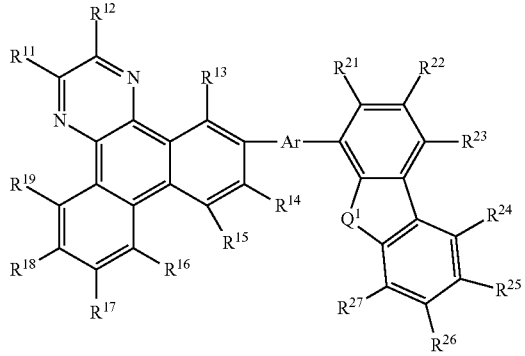

(G2-1)

In the general formula (G2-1), $Q^1$ represents any of a sulfur atom, an oxygen atom, and a nitrogen atom, and the nitrogen atom has an alkyl group having 1 to 4 carbon atoms or a substituted or unsubstituted aryl group having 6 to 13 carbon atoms as a substituent. In addition, $R^{11}$ to $R^{19}$ and $R^{21}$ to $R^{27}$ separately represent any of hydrogen, an alkyl group having 1 to 4 carbon atoms, and a substituted or unsubstituted aryl group having 6 to 14 carbon atoms, and Ar represents a substituted or unsubstituted arylene group having 6 to 13 carbon atoms.

Another embodiment of the present invention is a heterocyclic compound represented by the general formula (G2-2) below.

[Chemical Formula 11]

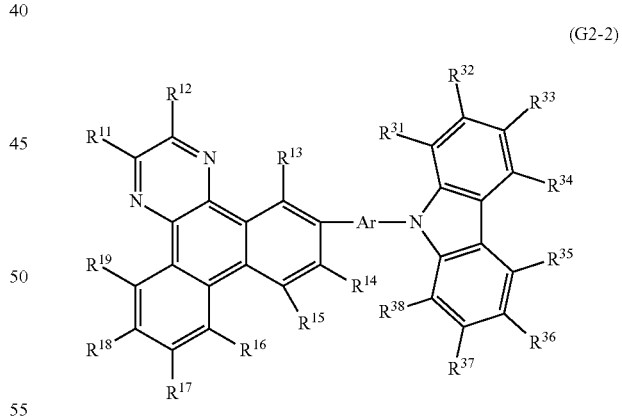

(G2-2)

In the general formula (G2-2), $R^{11}$ to $R^{19}$ and $R^{31}$ to $R^{38}$ separately represent any of hydrogen, an alkyl group having 1 to 4 carbon atoms, and a substituted or unsubstituted aryl group having 6 to 14 carbon atoms, and Ar represents a substituted or unsubstituted arylene group having 6 to 13 carbon atoms.

Another embodiment of the present invention is a heterocyclic compound represented by the general formula (G2-3) below.

[Chemical Formula 12]

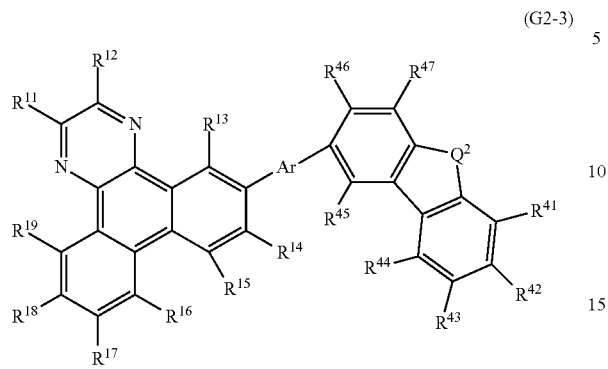

(G2-3)

In the general formula (G2-3), $R^{11}$ to $R^{19}$ and $R^{41}$ to $R^{47}$ separately represent any of hydrogen, an alkyl group having 1 to 4 carbon atoms, and a substituted or unsubstituted aryl group having 6 to 14 carbon atoms, Ar represents a substituted or unsubstituted arylene group having 6 to 13 carbon atoms, $Q^2$ represents any of a sulfur atom, an oxygen atom, and a nitrogen atom, and the nitrogen atom has an alkyl group having 1 to 4 carbon atoms or a substituted or unsubstituted aryl group having 6 to 14 carbon atoms as a substituent.

As Ar in the general formulae (G1), (G2-1), (G2-2), and (G2-3), there are a substituted or unsubstituted phenylene group, a substituted or unsubstituted biphenyldiyl group, a substituted or unsubstituted naphthalenediyl group, a substituted or unsubstituted fluorenediyl group, and the like. When the heterocyclic compound according to one embodiment of the present invention has any of these substituents, the heterocyclic compound has a high T1 level and can be favorably used as a host material in the case where a phosphorescent compound is used as a light-emitting substance. As specific structures, there are substituents represented by structural formulae (1-1) to (1-5), for example. When Ar has a substituent, it is preferable that the substituent be an alkyl group having 1 to 4 carbon atoms.

[Chemical Formula 13]

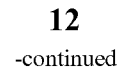

(1-1)

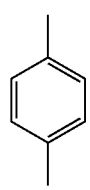

(1-2)

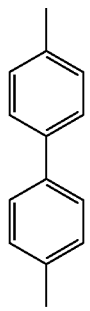

(1-3)

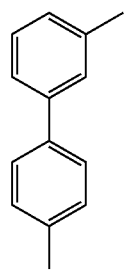

(1-4)

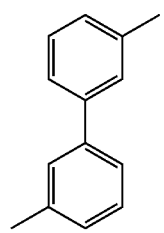

(1-5)

It is preferable that an arylene group be bonded at a para position as in the structural formulae (1-1) and (1-3) because, in such a case, a favorable carrier-transport property can be obtained. It is also preferable that an arylene group be bonded at a meta position as in the structural formulae (1-2), (1-4), and (1-5) because, in such a case, the heterocyclic compound has a high T1 level or a high S1 level.

When the heterocyclic compound represented by the general formulae (G1), (G2-1), (G2-2), or (G2-3) is used as a host material in the case where a phosphorescent compound which emits light having a shorter wavelength than light of the heterocyclic compound is used as a light-emitting substance, Ar is preferably a substituted or unsubstituted phenylene group or a substituted or unsubstituted biphenyldiyl group, particularly a substituted or unsubstituted phenylene group. Furthermore, Ar is much preferably a substituted or unsubstituted m-phenylene group so as to have a high T1 level or a high S1 level. Moreover, when Ar is a substituted or unsubstituted p-phenylene group, a favorable carrier-transport property can be obtained, which is preferable.

Another embodiment of the present invention is the heterocyclic compound represented by the general formula (G3-1) below.

[Chemical Formula 14]

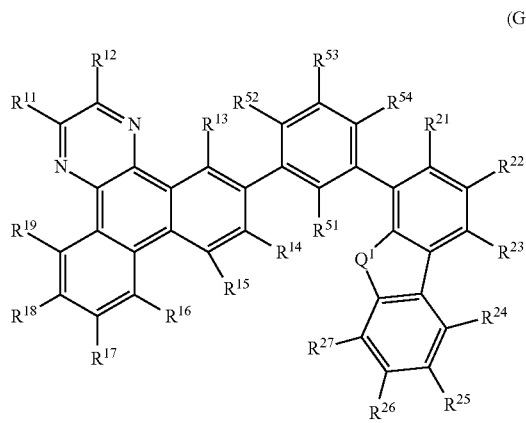

(G3-1)

In the general formula (G3-1), $Q^1$ represents any of a sulfur atom, an oxygen atom, and a nitrogen atom, and the nitrogen atom has an alkyl group having 1 to 4 carbon atoms or a substituted or unsubstituted aryl group having 6 to 13 carbon atoms as a substituent. In addition, $R^{11}$ to $R^{19}$, $R^{21}$ to $R^{27}$, and $R^{51}$ to $R^{54}$ separately represent any of hydrogen, an alkyl group having 1 to 4 carbon atoms, and a substituted or unsubstituted aryl group having 6 to 14 carbon atoms.

Yet another embodiment of the present invention is the heterocyclic compound represented by the general formula (G3-2) below.

[Chemical Formula 15]

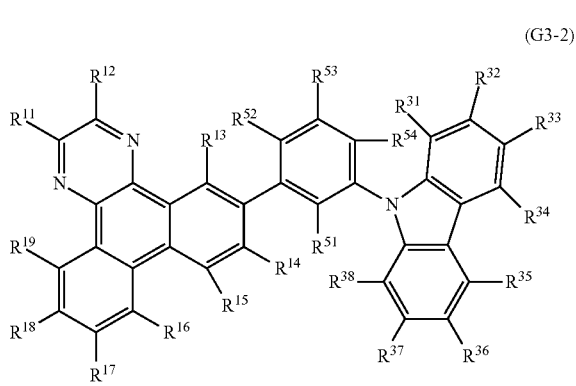

(G3-2)

In the general formula (G3-2), $R^{11}$ to $R^{19}$, $R^{31}$ to $R^{38}$, and $R^{51}$ to $R^{54}$ separately represent any of hydrogen, an alkyl group having 1 to 4 carbon atoms, and a substituted or unsubstituted aryl group having 6 to 14 carbon atoms.

Yet another embodiment of the present invention is the heterocyclic compound represented by the general formula (G3-3) below.

[Chemical Formula 16]

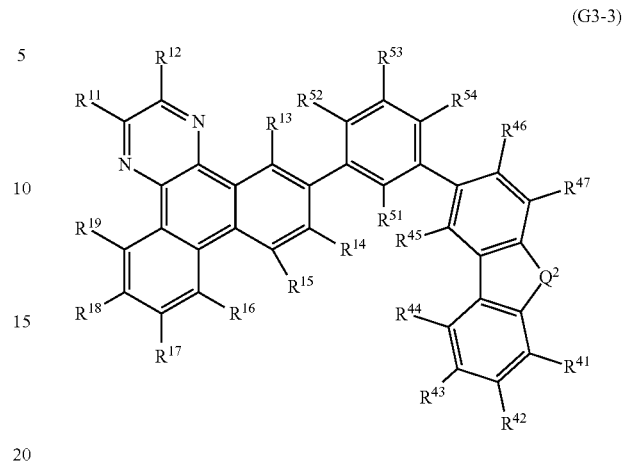

(G3-3)

In the general formula (G3-3), $R^{11}$ to $R^{19}$, $R^{41}$ to $R^{47}$, and $R^{51}$ to $R^{54}$ separately represent any of hydrogen, an alkyl group having 1 to 4 carbon atoms, and a substituted or unsubstituted aryl group having 6 to 14 carbon atoms, $Q^2$ represents any of a sulfur atom, an oxygen atom, and a nitrogen atom, and the nitrogen atom has an alkyl group having 1 to 4 carbon atoms or a substituted or unsubstituted aryl group having 6 to 14 carbon atoms as a substituent.

As $R^{11}$ to $R^{19}$, $R^{21}$ to $R^{27}$, $R^{31}$ to $R^{38}$, $R^{41}$ to $R^{47}$, and $R^{51}$ to $R^{54}$ in the general formulae (G1), (G2-1), (G2-2), (G2-3), (G3-1), (G3-2) and (G3-3), there are an alkyl group having 1 to 4 carbon atoms, a substituted or unsubstituted phenyl group, a substituted or unsubstituted biphenyl group, a substituted or unsubstituted naphthyl group, a substituted or unsubstituted fluorenyl group, a substituted or unsubstituted phenanthryl group, and the like. In the case of an alkyl group, high solubility in a solvent is obtained to facilitate synthesis or film formation using a wet process, which is preferable. In the case of an aryl group, a carrier-transport property is improved, which is also preferable. When the heterocyclic compound according to one embodiment of the present invention has any of these substituents, the heterocyclic compound has a high T1 level and thus can be favorably used as a host material in the case where a phosphorescent compound is used as a light-emitting substance. Moreover, a higher amorphous property and stable film quality can be obtained, which is preferable. As specific structures, there are substituents represented by structural formulae (2-1) to (2-15), for example. Further, when any of $R^{11}$ to $R^{19}$, $R^{21}$ to $R^{27}$, $R^{31}$ to $R^{38}$, $R^{41}$ to $R^{47}$, and $R^{51}$ to $R^{54}$ is an aryl group having a substituent, it is preferable that the substituent be an alkyl group having 1 to 4 carbon atoms.

[Chemical Formula 17]

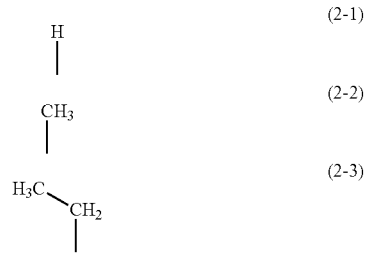

(2-1)

(2-2)

(2-3)

(2-4) 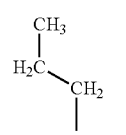

(2-5) 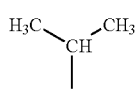

(2-6) 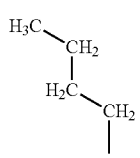

(2-7) 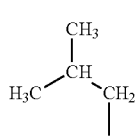

(2-8) 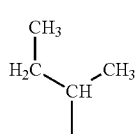

(2-9) 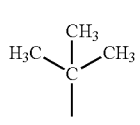

(2-10) 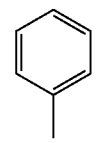

(2-11) 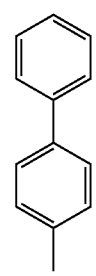

(2-12) 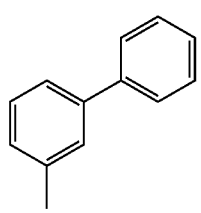

(2-13) 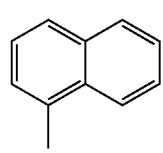

(2-14) 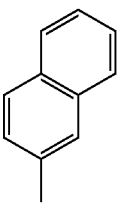

(2-15) 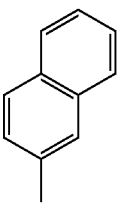

However, in consideration of the ease of synthesis, $R^{11}$ to $R^{19}$, $R^{21}$ to $R^{27}$, $R^{31}$ to $R^{38}$, $R^{41}$ to $R^{47}$, and $R^{51}$ to $R^{54}$ are preferably hydrogen.

In the case where $Q^1$ in the general formulae (G2-1) and (G3-1) or $Q^2$ in the general formulae (G2-3) and (G3-3) is a nitrogen atom, as examples of a substituent of the nitrogen atom, there are an alkyl group having 1 to 4 carbon atoms, a substituted or unsubstituted phenyl group, a substituted or unsubstituted biphenyl group, a substituted or unsubstituted naphthyl group, a substituted or unsubstituted fluorenyl group, a substituted or unsubstituted phenanthryl group, and the like. When the heterocyclic compound according to one embodiment of the present invention has any of these substituents, the heterocyclic compound has a high T1 level and thus can be favorably used as a host material in the case where a phosphorescent compound is used as a light-emitting substance. As specific structures, there are substituents represented by structural formulae (3-1) to (3-6), for example. In addition, when any of the heterocyclic compounds according to one embodiment of the present invention has a nitrogen atom and the nitrogen atom has an aryl group having a substituent as a substituent, the substituent of the aryl group is preferably an alkyl group having 1 to 4 carbon atoms.

[Chemical Formula 18]

(3-1) 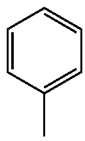

(3-2) 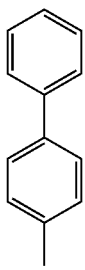

(3-3)
(3-4)
(3-5)
(3-6)
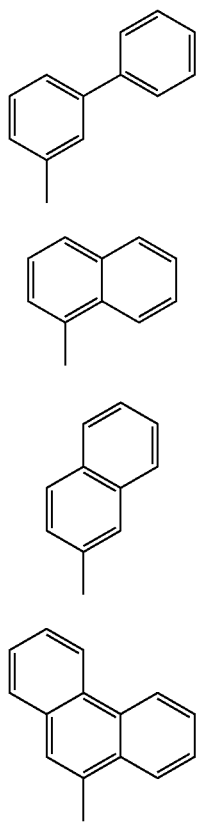
Specific examples of the heterocyclic compound represented by the general formula (G1) include, but are not limited to, heterocyclic compounds represented by structural formulae (100) to (129).
[Chemical Formula 19]
(100)
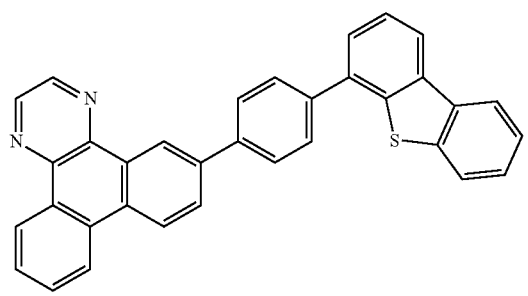
(101)
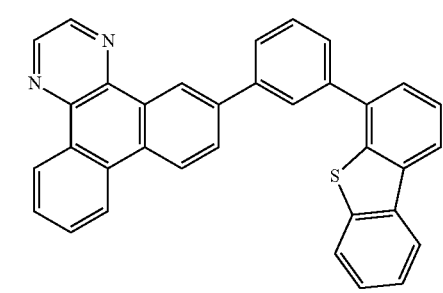
(102)
(103)
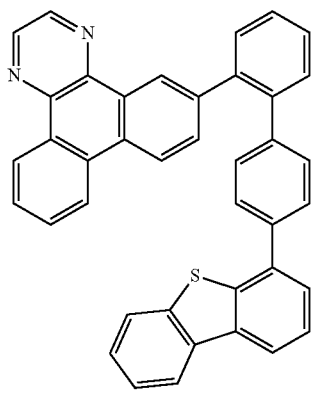
(104)
(105)
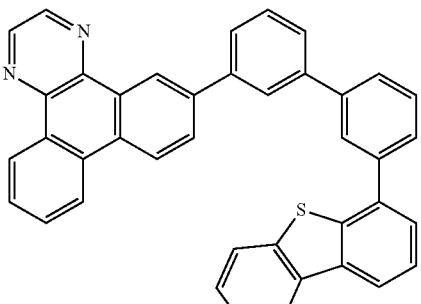

[Chemical Formula 20]
(106)
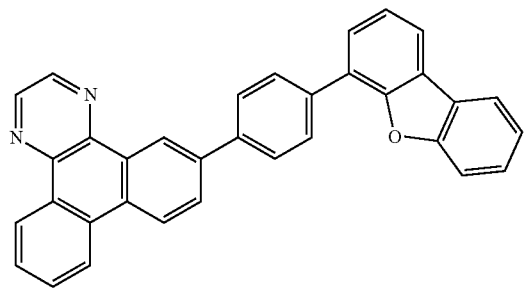
(107)
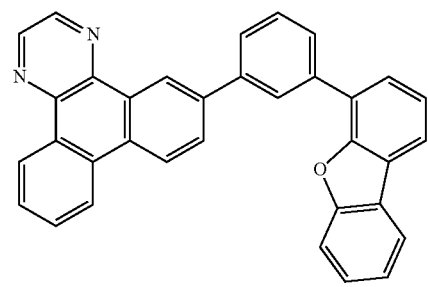
(108)
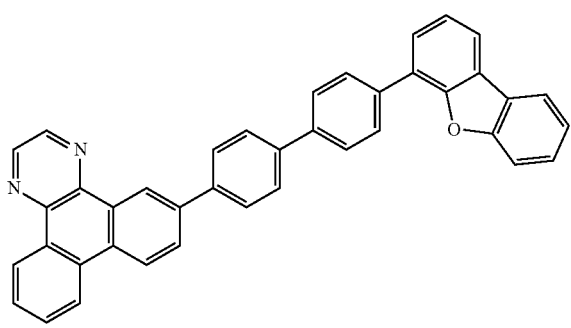
(109)
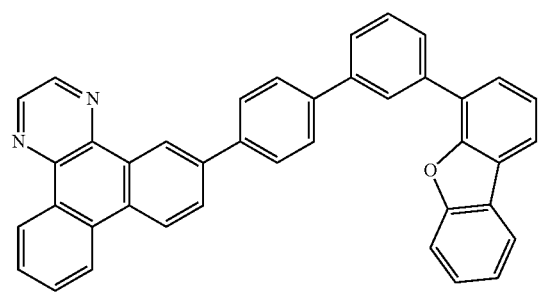
(110)
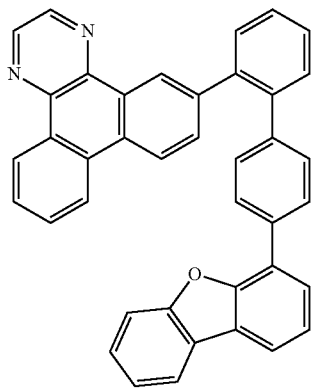
(111)
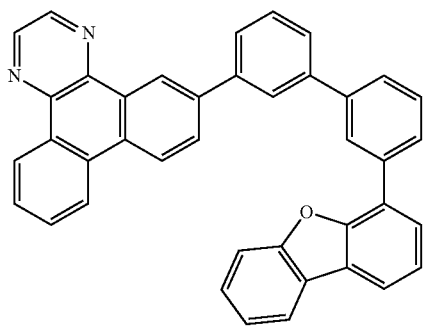
[Chemical Formula 21]
(112)
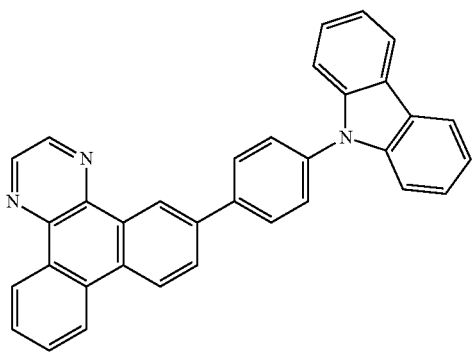
(113)
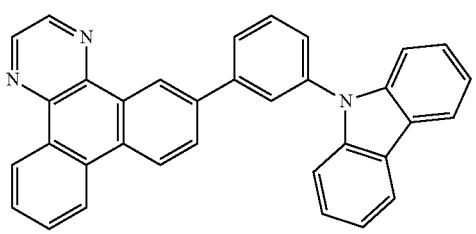

[Chemical Formula 22]
(114)
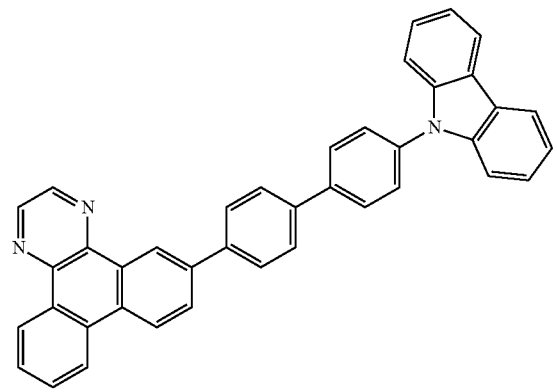
(115)
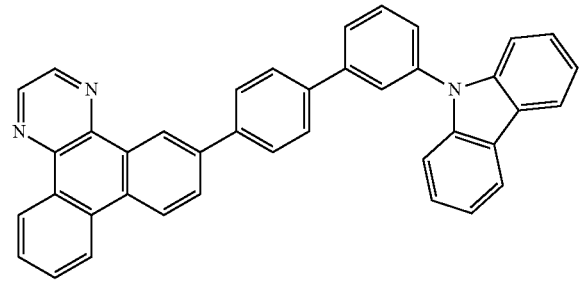
(116)
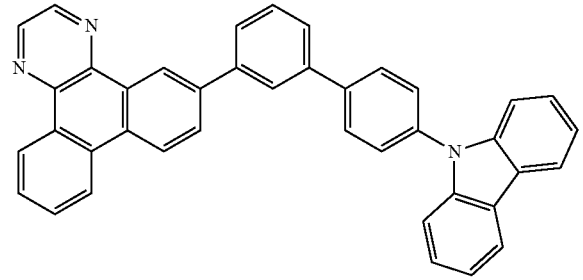
(117)
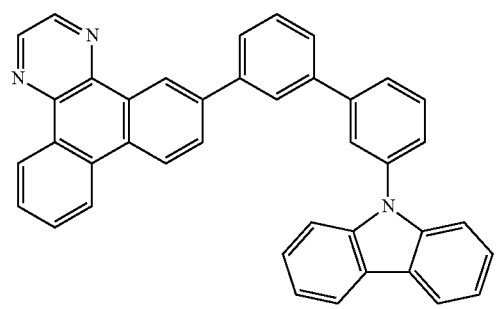
(118)
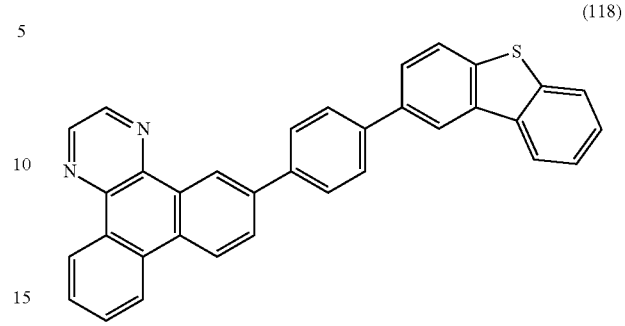
(119)
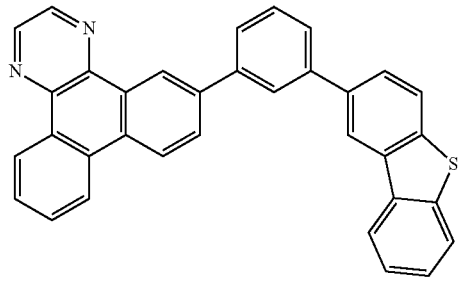
(120)
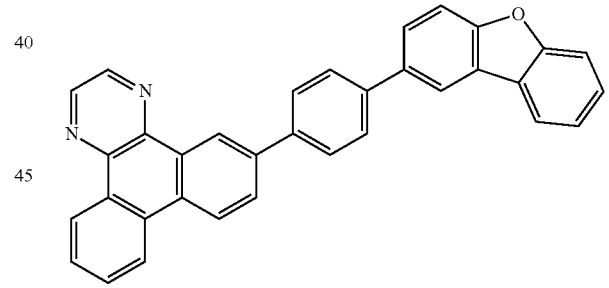
(121)
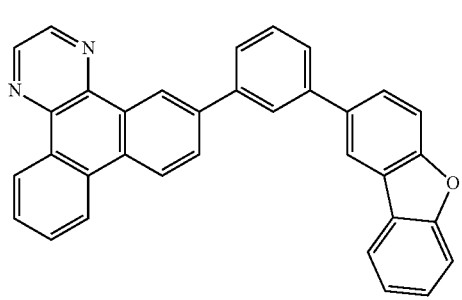

(122)
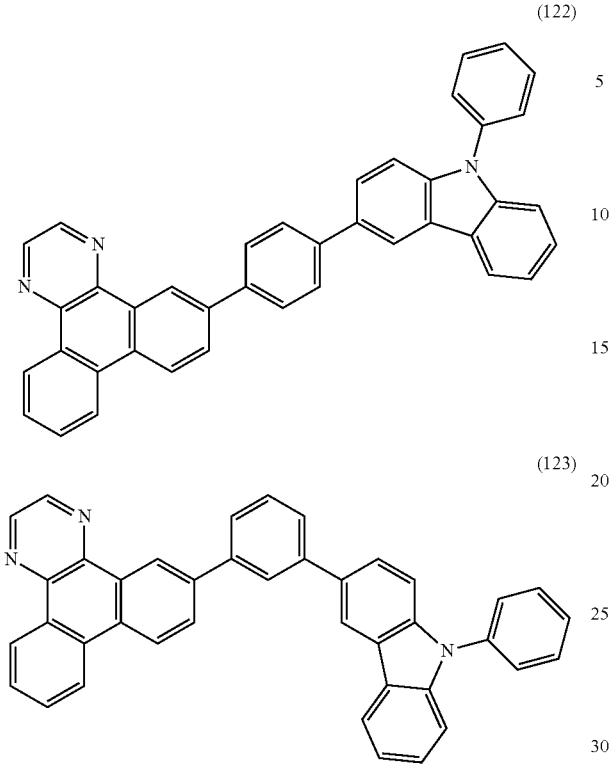

(123)

[Chemical Formula 23]

(124)
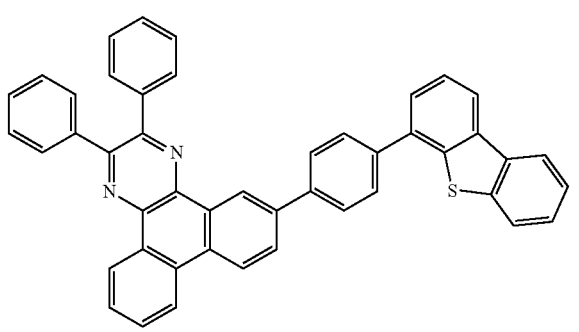

(125)
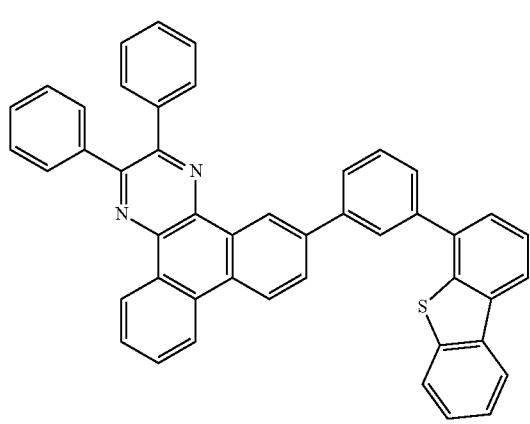

(126)
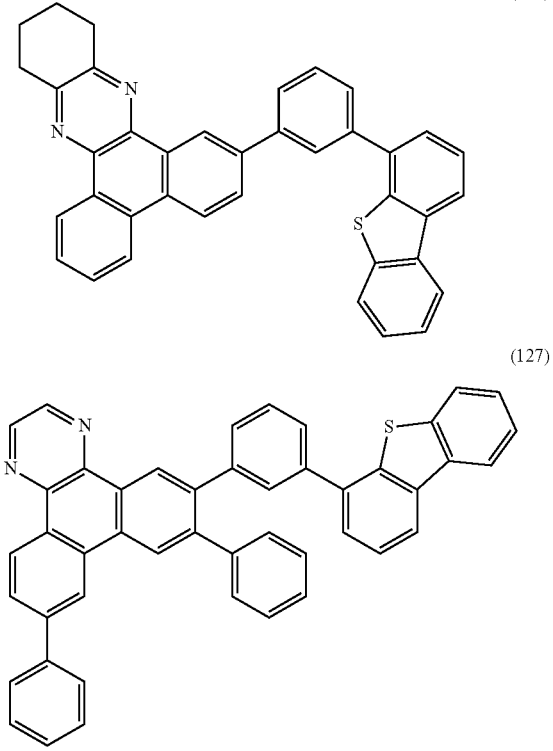

(127)

(128)
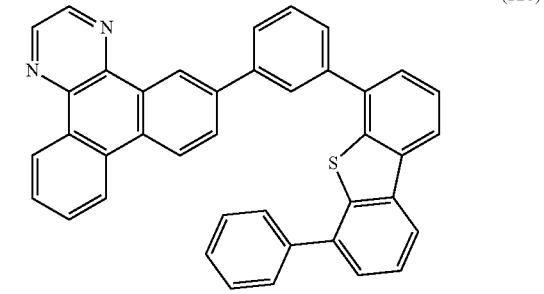

(129)
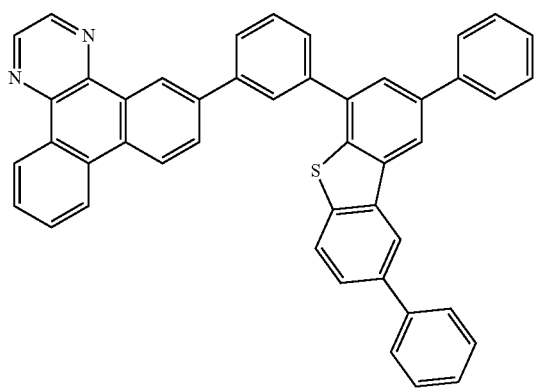

Furthermore, a heterocyclic compound used for the synthesis of any of the heterocyclic compounds of this embodiment is also a novel substance; therefore, this heterocyclic compound is also included in one embodiment of the present invention. Therefore, another embodiment of the present invention is a heterocyclic compound represented by the general formula (G4).

[Chemical Formula 24]

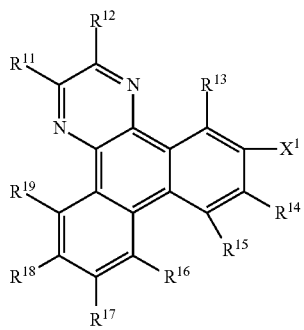

In the general formula (G4), $R^{11}$ to $R^{19}$ separately represent any of hydrogen, an alkyl group having 1 to 4 carbon atoms, and a substituted or unsubstituted aryl group having 6 to 14 carbon atoms, and $X^1$ represents a halogen.

A variety of reactions can be applied to a method of synthesizing any of the heterocyclic compounds according to one embodiment of the present invention. For example, synthesis reactions described below enable the synthesis of any of the heterocyclic compounds according to one embodiment of the present invention represented by the general formula (G1). Note that the method of synthesizing any of the heterocyclic compounds according to one embodiment of the present invention is not limited to the synthesis methods below.

<<Method of Synthesizing Heterocyclic Compound Represented by General Formula (G1)>>

<Step 1>

As illustrated in a synthesis scheme (A-1), a phenanthrenedione compound (a1) is halogenated, so that a halogenated phenanthrenedione compound (a2) is obtained.

[Chemical Formula 25]

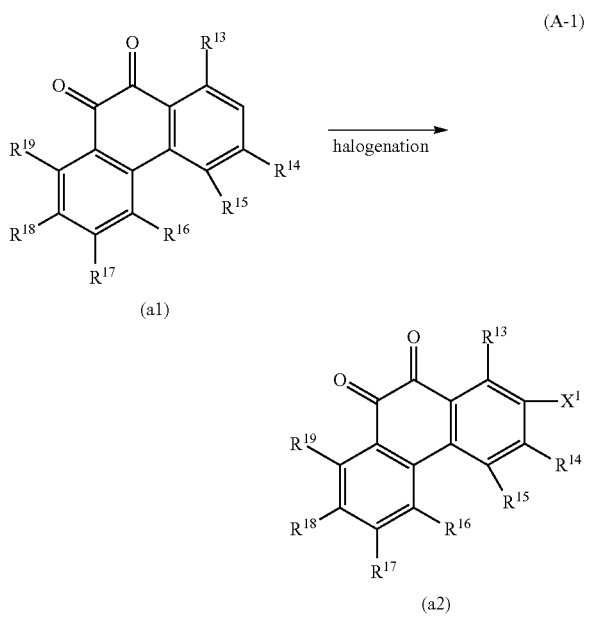

In the synthesis scheme (A-1), $R^{13}$ to $R^{19}$ separately represent any of hydrogen, an alkyl group having 1 to 4 carbon atoms, and a substituted or unsubstituted aryl group having 6 to 14 carbon atoms. $X^1$ represents a halogen (chlorine, bromine, or iodine). $X^1$ preferably represents bromine, more preferably iodine, which have high reactivity.

Note that a variety of reaction conditions can be employed for the halogenation reaction in the synthesis scheme (A-1). For example, in the case of bromination, there is a synthesis method in which N-bromosuccinimide reacts in sulfuric acid. In the case of iodination, there is a synthesis method in which iodine reacts in a mixture of glacial acetic acid, sulfuric acid, and nitric acid.

<Step 2>

Then, as illustrated in a synthesis scheme (A-2), the halogenated phenanthrenedione compound (a2) and an ethylenediamine compound (a3) are subjected to dehydration condensation, so that a halogenated dibenzoquinoxaline compound (G4) is obtained.

[Chemical Formula 26]

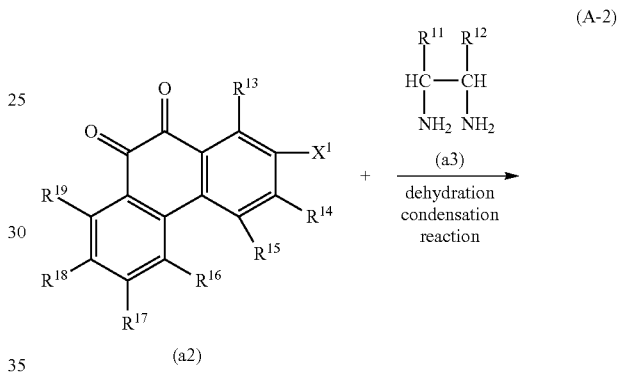

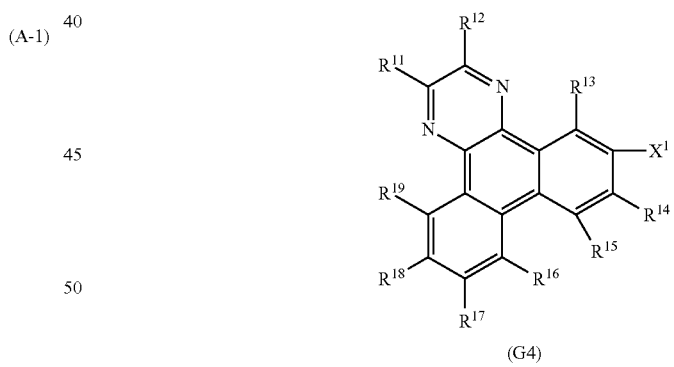

In the synthesis scheme (A-2), $R^{11}$ to $R^{19}$ separately represent any of hydrogen, an alkyl group having 1 to 4 carbon atoms, and a substituted or unsubstituted aryl group having 6 to 14 carbon atoms. $X^1$ represents a halogen (chlorine, bromine, or iodine). $X^1$ preferably represents bromine, more preferably iodine, which have high reactivity.

<Step 3>

Next, as illustrated in the following synthesis scheme (A-3), the halogenated dibenzoquinoxaline compound (G4) and a boron compound (a4) are coupled, so that the heterocyclic compound represented by the general formula (G1) is obtained.

[Chemical Formula 27]

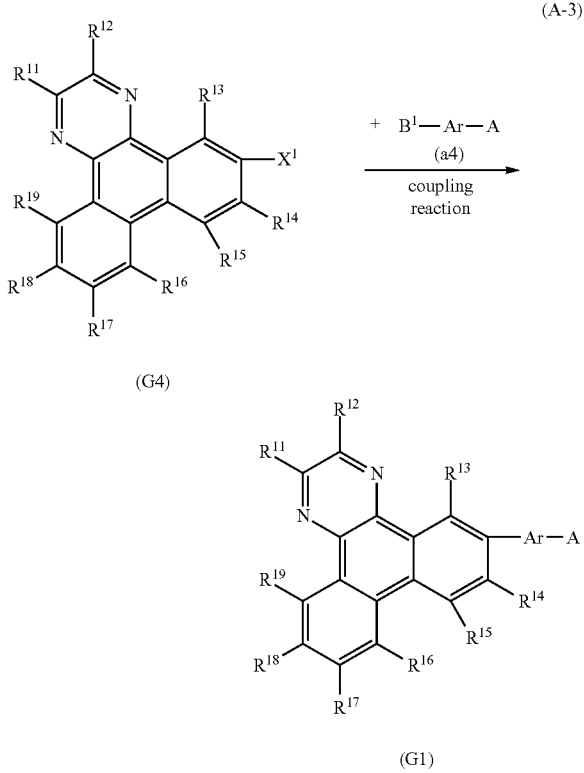

(G4)

(G1)

In the synthesis scheme (A-3), A represents any of a substituted or unsubstituted dibenzofuranyl group, a substituted or unsubstituted dibenzothiophenyl group, and a substituted or unsubstituted carbazolyl group, $R^{11}$ to $R^{19}$ separately represent any of hydrogen, an alkyl group having 1 to 4 carbon atoms, and a substituted or unsubstituted aryl group having 6 to 14 carbon atoms, and Ar represents a substituted or unsubstituted arylene group having 6 to 13 carbon atoms. $X^1$ represents a halogen (chlorine, bromine, or iodine). $X^1$ preferably represents bromine, more preferably iodine, which have high reactivity. $B^1$ represents a boronic acid or dialkoxyboron.

Note that there are a variety of reaction conditions for the coupling reaction in the synthesis scheme (A-3). As an example, a synthesis method using a metal catalyst in the presence of a base can be employed. For example, a Suzuki-Miyaura reaction can be employed.

Although another method can be employed for synthesizing a halogenated dibenzoquinoxaline compound, the synthesis method according to one embodiment of the present invention, which is an easy synthesis method, allows halogenation to be performed in one step. This is because of a halide of dibenzoquinoxaline having a halogen at the 6-position (involving halogenation of the 2-position of the phenanthrenedione compound). Thus, the heterocyclic compounds of this embodiment can be easily synthesized.

Thus, the heterocyclic compounds of this embodiment can be synthesized.

The heterocyclic compounds of this embodiment have a wide energy gap. Accordingly, by the use of any of the heterocyclic compounds for a light-emitting element, as a host material of a light-emitting layer in which a light-emitting substance is dispersed, high current efficiency can be obtained. In particular, the heterocyclic compounds of this embodiment are suitably used as a host material in which a phosphorescent compound is dispersed. Further, since the heterocyclic compounds of this embodiment are substances having a high electron-transport property, any of the heterocyclic compounds can be suitably used as a material for an electron-transport layer in a light-emitting element. By the use of any of the heterocyclic compounds of this embodiment, a light-emitting element having low driving voltage can be realized. In addition, a light-emitting element having high current efficiency can be realized. A light-emitting element having a long lifetime can also be realized. Furthermore, by the use of this light-emitting element, a light-emitting device, an electronic device, and a lighting device each having reduced power consumption can be obtained.

Embodiment 2

In this embodiment, as one mode of the present invention, a light-emitting element in which any of the heterocyclic compounds described in Embodiment 1 is used for a light-emitting layer is described with reference to FIGS. 1A to 1C.

A light-emitting element having an EL layer 102 between a first electrode 103 and a second electrode 108 is illustrated in FIG. 1A. The light-emitting element illustrated in FIG. 1A includes a hole-injection layer 701, a hole-transport layer 702, a light-emitting layer 703, an electron-transport layer 704, and an electron-injection layer 705 which are stacked in this order over the first electrode 103, and the second electrode 108 provided over the layers. The light-emitting layer 703 includes any of the heterocyclic compounds according to one embodiment of the present invention which are described in Embodiment 1.

For the first electrode 103, any of metals, alloys, electrically conductive compounds, mixtures thereof, and the like which has a high work function (specifically, a work function of 4.0 eV or more) is preferably used. Specific examples are indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide (IWZO), and the like. Films of these conductive metal oxides are usually formed by sputtering, but may be formed by application of a sol-gel method or the like. For example, a film of indium oxide-zinc oxide can be formed by a sputtering method using a target obtained by addition of 1 wt % to 20 wt % of zinc oxide to indium oxide. Further, an IWZO film can be formed by a sputtering method using a target obtained by addition of 0.5 wt % to 5 wt % of tungsten oxide and 0.1 wt % to 1 wt % of zinc oxide to indium oxide. Other examples are graphene, gold, platinum, nickel, tungsten, chromium, molybdenum, iron, cobalt, copper, palladium, nitrides of metal materials (e.g., titanium nitride), and the like.

However, when a layer which is in contact with the first electrode 103 and included in the EL layer 102 is formed using a composite material described later in which an organic compound and an electron acceptor (acceptor) are mixed, as a substance used for the first electrode 103, any of a variety of metals, alloys, and electrically conductive compounds, a mixture thereof, and the like can be used regardless of work function. For example, aluminum, silver, an alloy containing aluminum (e.g., Al—Si), or the like can also be used.

The first electrode 103 can be formed by, for example, a sputtering method, an evaporation method (including a vacuum evaporation method), or the like.

For the second electrode 108, any of metals, alloys, electrically conductive compounds, mixtures thereof, and the like which has a low work function (preferably 3.8 eV or less) is preferably used. Specifically, in addition to elements that belong to Group 1 or Group 2 in the periodic table, that is, alkali metals such as lithium and cesium, alkaline earth metals such as calcium, strontium, and magnesium, alloys thereof (e.g., Mg—Ag and Al—Li), rare earth metals such as europium and ytterbium, and alloys thereof, aluminum, silver, or the like can be used.

When a composite material described later in which an organic compound and an electron donor (donor) is used for a layer included in the EL layer 102 which is formed in contact with the second electrode 108, a variety of conductive materials such as Al, Ag, ITO, and indium oxide-tin oxide containing silicon or silicon oxide can be used regardless of work function.

When the second electrode 108 is formed, a vacuum evaporation method or a sputtering method can be used. When a silver paste or the like is used, a coating method, an inkjet method, or the like can be used.

The EL layer 102 has at least the light-emitting layer 703, which is formed so as to include any of the heterocyclic compounds according to one embodiment of the present invention. A known substance can also be used for a part of the EL layer 102, and either a low molecular compound or a high molecular compound can be used. Note that a substance included in the EL layer 102 is not limited to an organic compound, and may be a structure in which an inorganic compound is included as a part.

As illustrated in FIG. 1A, the EL layer 102 is formed in such a way that, in addition to the light-emitting layer 703, the hole-injection layer 701 which includes a substance having a high hole-injection property, the hole-transport layer 702 which includes a substance having a high hole-transport property, the electron-transport layer 704 which includes a substance having a high electron-transport property, the electron-injection layer 705 which includes a substance having a high electron-injection property, and the like are combined and stacked as appropriate.

The hole-injection layer 701 is a layer that includes a substance having a high hole-injection property. As the substance having a high hole-injection property, a metal oxide such as molybdenum oxide, titanium oxide, vanadium oxide, rhenium oxide, ruthenium oxide, chromium oxide, zirconium oxide, hafnium oxide, tantalum oxide, silver oxide, tungsten oxide, or manganese oxide can be used. A phthalocyanine-based compound such as phthalocyanine (abbreviation: $H_2Pc$), or copper(II) phthalocyanine (abbreviation: CuPc) can also be used.

Any of the following aromatic amine compounds which are low molecular organic compounds can also be used: 4,4', 4"-tris(N,N-diphenylamino)triphenylamine (abbreviation: TDATA), 4,4',4"-tris[N-(3-methylphenyl)-N-phenylamino] triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

A high molecular compound (e.g., an oligomer, a dendrimer, or a polymer) can also be used. Examples are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl] phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). A high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can also be used.

For the hole-injection layer 701, the composite material in which an organic compound and an electron acceptor (acceptor) are mixed may be used. Such a composite material is excellent in a hole-injection property and a hole-transport property because the electron acceptor causes hole generation in the organic compound. In this case, the organic compound is preferably a material excellent in transporting the generated holes (a substance having a high hole-transport property).

As the organic compound used for the composite material, any of a variety of compounds such as aromatic amine compounds, carbazole derivatives, aromatic hydrocarbons, and high molecular compounds (e.g., oligomers, dendrimers, and polymers) can be used. The organic compound used for the composite material is preferably an organic compound having a high hole-transport property. Specifically, a substance having a hole mobility of $10^{-6}$ cm$^2$/Vs or more is preferably used. Note that other than these substances, a substance that has a property of transporting more holes than electrons may be used. The organic compounds which can be used for the composite material are specifically given below.

Examples of the organic compounds that can be used for the composite material include the following: aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)phenyl]-10-phenylanthracene (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl]-2,3,5,6-tetraphenylbenzene.

Any of the following aromatic hydrocarbon compounds can be used: 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl) anthracene (abbreviation: t-BuDBA), 9,10-di(2-naphthyl) anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, and 2,3,6,7-tetramethyl-9,10-di(1-naphthyl)anthracene.

Any of the following aromatic hydrocarbon compounds can be used: 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl) phenyl]anthracene (abbreviation: DPVPA).

Examples of the electron acceptor include organic compounds such as 7,7,8,8-tetracyano-2,3,5,6-tetrafluoroquinodimethane (abbreviation: $F_4$-TCNQ) and chloranil and transition metal oxides. Other examples include oxides of metals that belong to any of Groups 4 to 8 in the periodic table. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide, which is easy to handle owing to its stability in the air and low hygroscopic property, is particularly preferred.

The composite material may be formed using the above-described electron acceptor and the above-described high molecular compound such as PVK, PVTPA, PTPDMA, or Poly-TPD, and used for the hole-injection layer 701.

The hole-transport layer 702 is a layer that includes a substance having a high hole-transport property. Examples of the substance having a high hole-transport property include aromatic amine compounds such as NPB, TPD, BPAFLP, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly substances that have a hole mobility of $10^{-6}$ cm$^2$/Vs or more. Note that other than these substances, a substance that has a property of transporting more holes than electrons may be used. Note that the layer that includes a substance having a high hole-transport property is not limited to a single layer, and may be a stack of two or more layers including any of the above substances.

For the hole-transport layer 702, a carbazole derivative such as CBP, CzPA, or PCzPA or an anthracene derivative such as t-BuDNA, DNA, or DPAnth may also be used.

For the hole-transport layer 702, a high molecular compound such as PVK, PVTPA, PTPDMA, or Poly-TPD can also be used.

The light-emitting layer 703 is a layer that includes a light-emitting substance. The light-emitting layer 703 of this embodiment includes any of the heterocyclic compounds according to one embodiment of the present invention. In the light-emitting layer in which a light-emitting substance (guest material) is dispersed in another substance (host material), the heterocyclic compound according to one embodiment of the present invention can be used for the host material. The guest material which is a light-emitting substance is dispersed in the heterocyclic compound according to one embodiment of the present invention, so that light emission from the guest material can be obtained.

Any of the heterocyclic compounds according to one embodiment of the present invention has a high S1 level and a high T1 level and thus can be used as a host material for a fluorescent compound which emits blue to red fluorescence or a phosphorescent compound which emits yellow to red phosphorescence.

In addition, a plurality of kinds of substances can be used as the substances (host materials) in which the light-emitting substance (guest material) is dispersed. The light-emitting layer may thus include a different material as a host material in addition to the heterocyclic compound according to one embodiment of the present invention.

In particular, a material having a hole-transport property such as an amine-based compound or a carbazole-based compound may be mixed as the different host material. Since any of the heterocyclic compounds according to one embodiment of the present invention is a material having an extremely favorable electron-transport property, emission efficiency can be further improved when a host material that can favorably inject holes into the light-emitting layer and any of the heterocyclic compounds according to one embodiment of the present invention are contained as a host material of the light-emitting layer.

As the light-emitting substance, for example, a fluorescent compound which emits fluorescence or a phosphorescent compound which emits phosphorescence can be used. Examples of a fluorescent substance that can be used for the light-emitting layer 703 are the following light-emitting materials: materials that emit blue light, such as N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and 4-(10-phenyl-9-anthryl)-4'-(9-phenyl-9H-carbazol-3-yl) triphenylamine (abbreviation: PCBAPA); materials that emit green light, such as N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), and N,N,9-triphenylanthracen-9-amine (abbreviation: DPhAPhA); materials that emit yellow light, such as rubrene and 5,12-bis(1,1'-biphenyl-4-yl)-6,11-diphenyltetracene (abbreviation: BPT); and materials that emit red light, such as N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-diamine (abbreviation: p-mPhAFD).

In addition, the phosphorescent compounds that can be used for the light-emitting layer 703 are the following light-emitting materials, for example: materials that emit green light, such as tris(2-phenylpyridinato-N,C$^{2'}$)iridium(III) (abbreviation: [Ir(ppy)$_3$]), bis(2-phenylpyridinato-N,C$^{2'}$)iridium (III)acetylacetonate (abbreviation: [Ir(ppy)$_2$(acac)]), bis(1,2-diphenyl-1H-benzimidazolato)iridium(III)acetylacetonate (abbreviation: [Ir(pbi)$_2$(acac)]), bis(benzo[h]quinolinato)iridium(III)acetylacetonate (abbreviation: [Ir(bzq)$_2$(acac)]), tris(benzo[h]quinolinato)iridium(III) (abbreviation: [Ir(bzq)$_3$]); materials that emit yellow light, such as bis(2,4-diphenyl-1,3-oxazolato-N,C$^{2'}$)iridium(III)acetylacetonate (abbreviation: [Ir(dpo)$_2$(acac)]), bis {2-[4'-(perfluorophenylphenyl)]pyridinato-N,C$^{2'}$}iridium(III)acetylacetonate (abbreviation: [Ir(p-PF-ph)$_2$(acac)]), bis(2-phenylbenzothiazolato-N,C$^{2'}$)iridium(III)acetylacetonate (abbreviation: [Ir(bt)$_2$(acac)]), (acetylacetonato)bis[2,3-bis(4-fluorophenyl)-5-methylpyrazinato]iridium(III) (abbreviation: [Ir(Fdppr-Me)$_2$(acac)]), and (acetylacetonato)bis[2-(4-methoxyphenyl)-3,5-dimethylpyrazinato]iridium(III) (abbreviation: [Ir(dmmoppr)$_2$(acac)]); materials that emit orange light, such as tris(2-phenylquinolinato-N,C$^{2'}$)iridium (III) (abbreviation: [Ir(pq)$_3$]), bis(2-phenylquinolinato-N, C$^{2'}$)iridium(III)acetylacetonate (abbreviation: [Ir(pq)$_2$(acac)]), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]); and materials that emit red light, examples of which are organometallic complexes such as bis[2-(2'-benzo[4,5-α] thienyl)pyridinato-N,C$^{3'}$)iridium(III)acetylacetonate (abbreviation: [Ir(btp)$_2$(acac)]), bis(1-phenylisoquinolinato-N,C$^{2'}$) iridium(III)acetylacetonate (abbreviation: [Ir(piq)$_2$(acac)], (acetylacetonato)bis[2,3-bis(4-fluorophenyl)quinoxalinato] iridium(III) (abbreviation: [Ir(Fdpq)$_2$(acac)]), (acetylacetonato)bis(2,3,5-triphenylpyrazinato)iridium(III) (abbreviation: [Ir(tppr)$_2$(acac)]), (dipivaloylmethanato)bis(2,3,5-triphenylpyrazinato)iridium(III) (abbreviation: [Ir(tppr)$_2$(dpm)]), and (2,3,7,8,12,13,17,18-octaethyl-21H,23H-porphine)platinum(II) (abbreviation: PtOEP). As the phosphorescent compound, any of the following rare earth metal complexes can be used: tris(acetylacetonato)(monophenanthroline)terbium(III) (abbreviation: [Tb(acac)$_3$(Phen)]), tris(1,3-diphenyl-1,3-propanedionato)(monophenanthroline)europium(III) (abbreviation: [Eu(DBM)$_3$(Phen)]), and tris[1-(2-thenoyl)-3,3,3-trifluoroacetonato](monophenanthroline)europium(III) (abbreviation: [Eu(TTA)$_3$(Phen)]), because their light emission is from the rare earth metal ion (electron transfer between different multiplicities) in such a rare earth metal complex.

As the light-emitting substance, a high molecular compound can be used. Specific examples are the following light-emitting materials: materials that emit blue light, such as poly(9,9-dioctylfluorene-2,7-diyl) (abbreviation: PFO), poly[(9,9-dioctylfluorene-2,7-diyl)-co-(2,5-dimethoxybenzene-1,4-diyl)] (abbreviation: PF-DMOP), and poly{(9,9-dioctylfluorene-2,7-diyl)-co-[N,N'-di-(p-butylphenyl)-1,4-diaminobenzene]} (abbreviation: TAB-PFH); materials that emit green light, such as poly(p-phenyleneyinylene) (abbreviation: PPV), poly[(9,9-dihexylfluorene-2,7-diyl)-alt-co-(benzo[2,1,3]thiadiazole-4,7-diyl)] (abbreviation: PFBT), and poly[(9,9-dioctyl-2,7-diyinylenefluorenylene)-alt-co-(2-methoxy-5-(2-ethylhexyloxy)-1,4-phenylene)]; and materials that emit orange to red light, such as poly[2-methoxy-5-(2'-ethylhexoxy)-1,4-phenyleneyinylene] (abbreviation: MEH-PPV), poly(3-butylthiophene-2,5-diyl) (abbreviation: R4-PAT), poly{[9,9-dihexyl-2,7-bis(1-cyanoyinylene)fluorenylene]-alt-co-[2,5-bis(N,N'-diphenylamino)-1,4-phenylene]}, and poly{[2-methoxy-5-(2-ethylhexyloxy)-1,4-bis(1-cyanoyinylenephenylene)]-alt-co-[2,5-bis(N,N'-diphenylamino)-1,4-phenylene]} (abbreviation: CN-PPV-DPD).

Further, when a plurality of light-emitting layers are provided and emission colors of the layers are made different, light emission of a desired color can be obtained from the light-emitting element as a whole. For example, the emission colors of first and second light-emitting layers are complementary in a light-emitting element having the two light-emitting layers, so that the light-emitting element can be made to emit white light as a whole. Note that the term "complementary" means color relationship in which an achromatic color is obtained when colors are mixed. That is, emission of white light can be obtained by mixture of light emitted from substances whose emission colors are complementary colors. Further, the same applies to a light-emitting element having three or more light-emitting layers.

The electron-transport layer 704 is a layer that includes a substance having a high electron-transport property. Since any of the heterocyclic compounds according to one embodiment of the present invention is a substance having a favorable electron-transport property, the heterocyclic compound can be used for the electron-transport layer 704. When the same heterocyclic compound according to one embodiment of the present invention is used for the host material of the light-emitting layer and the electron-transport layer, the manufacturing cost of the light-emitting element can be suppressed, which can be regarded as a favorable structure.

As other examples of a substance that can be used for the electron-transport layer 704, there are metal complexes such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, and bis[2-(2-hydroxyphenyl)benzothiazolato]zinc (abbreviation: Zn(BTZ)$_2$). A heteroaromatic compound can be used, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs). A high molecular compound can be used, such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy). The substances described here are mainly substances having an electron mobility of 10$^{-6}$ cm$^2$/Vs or more. Other than the above substances, a substance that has a property of transporting electrons holes than holes may be used.

Further, the electron-transport layer is not limited to a single layer, and may be a stack of two or more layers including any of the above substances.

In addition, the carrier-transport layer (the hole-transport layer or the electron-transport layer) that is in contact with the light-emitting layer preferably has a higher S1 level (in the case where the light-emitting substance emits fluorescence) or a higher T1 level (in the case where the light-emitting substance emits phosphorescence) than the light-emitting substance contained in the light-emitting layer.

The electron-injection layer 705 is a layer that includes a substance having a high electron-injection property. For the electron-injection layer 705, an alkali metal, an alkaline earth metal, and a compound thereof, such as lithium, cesium, calcium, lithium fluoride, cesium fluoride, calcium fluoride, or lithium oxide can be used. A rare earth metal compound such as erbium fluoride can be used. The above-mentioned substances for forming the electron-transport layer 704 can also be used.

Alternatively, the composite material in which an organic compound and an electron donor (donor) are mixed may be used for the electron-injection layer 705. Such a composite material is excellent in an electron-injection property and an electron-transport property because the electron donor causes electron generation in the organic compound. In this case, the organic compound is preferably a material excellent in transporting the generated electrons. Specifically, for example, the substances for forming the electron-transport layer 704 (e.g., a metal complex or a heteroaromatic compound), which are described above, can be used. The electron donor is preferably a substance showing an electron-donating property with respect to the organic compound. Specifically, an alkali metal, an alkaline earth metal, and a rare earth metal are preferable, and lithium, cesium, magnesium, calcium, erbium, ytterbium, and the like can be given. Alkali metal oxides or alkaline earth metal oxides are also preferable and examples are lithium oxide, calcium oxide, barium oxide, and the like. A Lewis base such as magnesium oxide can also be used. An organic compound such as tetrathiafulvalene (abbreviation: TTF) can also be used.

Note that the hole-injection layer 701, the hole-transport layer 702, the light-emitting layer 703, the electron-transport layer 704, and the electron-injection layer 705 which are described above can be formed by a method, such as an evaporation method (e.g., a vacuum evaporation method), an inkjet method, or a coating method.

Figure 1B:
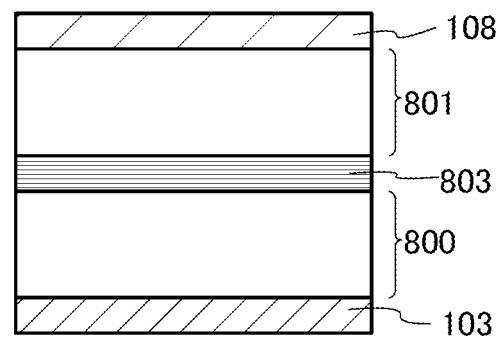

As illustrated in FIG. 1B, a plurality of EL layers may be stacked between the first electrode 103 and the second electrode 108. In this case, a charge generation layer 803 is preferably provided between a first EL layer 800 and a second EL layer 801 which are stacked. The charge generation layer 803 can be formed with either of the above-mentioned composite materials. Further, the charge generation layer 803 may have a stacked structure including a layer formed of the composite material and a layer formed of another material; in this case, as the layer formed of another material, a layer that includes a substance having an electron-donating property and a substance having a high electron-transport property, a layer formed of a transparent conductive film, or the like can be used. A light-emitting element having such a structure is less likely to have problems such as energy transfer and quenching, and gives an extensive choice of materials, and, accordingly, can easily be a light-emitting element having both high emission efficiency and a long lifetime. Further, a structure in which phosphorescence is obtained from one of the EL layers and fluorescence is obtained from the other is easily obtained. This structure can be combined with the above-mentioned structures of the EL layer.

Furthermore, when emission colors of EL layers are made different, light emission of a desired color can be obtained from the light-emitting element as a whole. For example, the emission colors of first and second EL layers are complementary in a light-emitting element having the two EL layers, so that the light-emitting element can be made to emit white light as a whole. Further, the same applies to a light-emitting element having three or more EL layers.

Figure 1C:
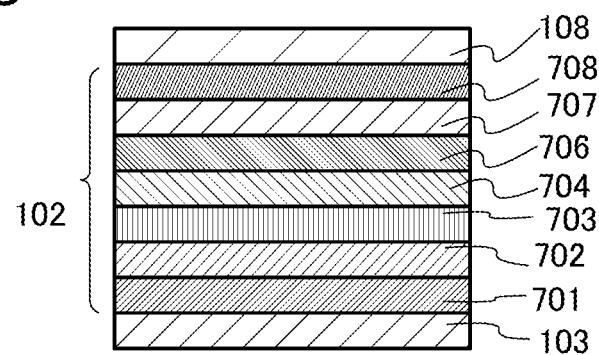

As illustrated in FIG. 1C, the EL layer 102 may include the hole-injection layer 701, the hole-transport layer 702, the light-emitting layer 703, the electron-transport layer 704, an electron-injection buffer layer 706, an electron-relay layer 707, and a composite material layer 708 which is in contact with the second electrode 108, between the first electrode 103 and the second electrode 108.

It is preferable to provide the composite material layer 708 which is in contact with the second electrode 108, because, in this case, damage to the EL layer 102 caused particularly when the second electrode 108 is formed by a sputtering method can be reduced. The composite material layer 708 can be formed using the above-described composite material in which a substance having an acceptor property is contained with an organic compound having a high hole-transport property.

Further, with the electron-injection buffer layer 706, an injection barrier between the composite material layer 708 and the electron-transport layer 704 can be reduced; thus, electrons generated in the composite material layer 708 can be easily injected into the electron-transport layer 704.

A substance having a high electron-injection property, such as an alkali metal, an alkaline earth metal, a rare earth metal, a compound of the above metal (e.g., an alkali metal compound (e.g., an oxide such as lithium oxide, a halide, or a carbonate such as lithium carbonate or cesium carbonate), an alkaline earth metal compound (e.g., an oxide, a halide, or a carbonate), or a rare earth metal compound (e.g., an oxide, a halide, or a carbonate), can be used for the electron-injection buffer layer 706.

Further, in the case where the electron-injection buffer layer 706 includes a substance having a high electron-transport property and a substance having a donor property, the substance having a donor property is preferably added so that the mass ratio thereof to the substance having a high electron-transport property is greater than or equal to 0.001 and less than or equal to 0.1. Note that as the substance having a donor property, an organic compound such as tetrathianaphthacene (abbreviation: TTN), nickelocene, or decamethylnickelocene can be used as well as an alkali metal, an alkaline earth metal, a rare earth metal, and a compound of the above metal (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)). Note also that as the substance having a high electron-transport property, a material similar to the material for the electron-transport layer 704 described above can be used.

Furthermore, it is preferable that the electron-relay layer 707 be formed between the electron-injection buffer layer 706 and the composite material layer 708. The electron-relay layer 707 is not necessarily provided; however, with the electron-relay layer 707 having a high electron-transport property, electrons can be rapidly transported to the electron-injection buffer layer 706.

The structure in which the electron-relay layer 707 is interposed between the composite material layer 708 and the electron-injection buffer layer 706 is a structure in which the substance having an acceptor property included in the composite material layer 708 and the substance having a donor property included in the electron-injection buffer layer 706 are less likely to interact with each other, and thus their functions hardly interfere with each other. Accordingly, an increase in driving voltage can be suppressed.

The electron-relay layer 707 includes a substance having a high electron-transport property and is formed so that the LUMO level of the substance having a high electron-transport property is located between the LUMO level of the substance having an acceptor property included in the composite material layer 708 and the LUMO level of the substance having a high electron-transport property included in the electron-transport layer 704. In the case where the electron-relay layer 707 includes a donor substance, the donor level of the donor substance is controlled so as to be located between the LUMO level of the substance having an acceptor property included in the composite material layer 708 and the LUMO level of the substance having a high electron-transport property included in the electron-transport layer 704. As a specific value of the energy level, the LUMO level of the substance having a high electron-transport property included in the electron-relay layer 707 is preferably higher than or equal to −5.0 eV, more preferably higher than or equal to −5.0 eV and lower than or equal to −3.0 eV.

As the substance having a high electron-transport property included in the electron-relay layer 707, a phthalocyanine-based material or a metal complex having a metal-oxygen bond and an aromatic ligand is preferably used.

As the phthalocyanine-based material included in the electron-relay layer 707, any of the following is preferably used: CuPc, SnPc (phthalocyanine tin(II) complex), ZnPc (phthalocyanine zinc complex), CoPc (cobalt(II) phthalocyanine, β-form), FePc (phthalocyanine iron), and PhO-VOPc (vanadyl 2,9,16,23-tetraphenoxy-29H,31H-phthalocyanine).

A metal complex having a metal-oxygen double bond is preferably used as the metal complex having a metal-oxygen bond and an aromatic ligand, which is included in the electron-relay layer 707. The metal-oxygen double bond has an acceptor property (a property of easily accepting electrons); accordingly, electrons can be transferred (donated and accepted) more easily. Further, the metal complex having a metal-oxygen double bond is considered stable. Thus, the use of the metal complex having the metal-oxygen double bond enables the light-emitting element to be driven more stably at low voltage.

As the metal complex having a metal-oxygen bond and an aromatic ligand, a phthalocyanine-based material is preferable. Specifically, any of VOPc (vanadyl phthalocyanine), SnOPc (phthalocyanine tin(IV) oxide complex), and TiOPc (phthalocyanine titanium oxide complex) is preferable because a metal-oxygen double bond is likely to act on another molecule in terms of a molecular structure and an acceptor property is high.

Note that as the phthalocyanine-based materials described above, a phthalocyanine-based material having a phenoxy group is preferable. Specifically, a phthalocyanine derivative having a phenoxy group, such as PhO-VOPc, is preferable. The phthalocyanine derivative having a phenoxy group is soluble in a solvent and therefore has the advantage of being easy to handle during formation of a light-emitting element and the advantage of facilitating maintenance of an apparatus used for film formation.

The electron-relay layer 707 may further include a substance having a donor property. As the substance having a donor property, an organic compound such as tetrathianaphthacene (abbreviation: TTN), nickelocene, or decamethylnickelocene can be used as well as an alkali metal, an alkaline earth metal, a rare earth metal, and a compound of the above metal (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)). When such a substance having a donor property is included in the electron-relay layer 707, electrons can be transferred easily and the light-emitting element can be driven at lower voltage.

In the case where the substance having a donor property is included in the electron-relay layer 707, other than the materials described above as the substance having a high electron-transport property, a substance having a LUMO level higher than the acceptor level of the substance having an acceptor property included in the composite material layer 708 can be used. Specifically, it is preferable to use a substance having a LUMO level higher than or equal to −5.0 eV, preferably higher than or equal to −5.0 eV and lower than or equal to −3.0 eV. Examples of such a substance are perylene derivatives, nitrogen-containing condensed aromatic compounds, and the like. Note that a nitrogen-containing condensed aromatic compound is preferably used for a material used for formation of the electron-relay layer 707 because of its stability.

Specific examples of the perylene derivative are 3,4,9,10-perylenetetracarboxylic dianhydride (abbreviation: PTCDA), 3,4,9,10-perylenetetracarboxylic-bis-benzimidazole (abbreviation: PTCBI), N,N'-dioctyl-3,4,9,10-perylenetetracarboxylic diimide (abbreviation: PTCDI-C8H), N,N'-dihexyl-3,4,9,10-perylenetetracarboxylic diimide (abbreviation: Hex PTC), and the like.

Specific examples of the nitrogen-containing condensed aromatic compound are pirazino[2,3-f][1,10]phenanthroline-2,3-dicarbonitrile (abbreviation: PPDN), 2,3,6,7,10,11-hexacyano-1,4,5,8,9,12-hexaazatriphenylene (abbreviation: HAT(CN)$_6$), 2,3-diphenylpyrido[2,3-b]pyrazine (abbreviation: 2PYPR), 2,3-bis(4-fluorophenyl)pyrido[2,3-b]pyrazine (abbreviation: F2PYPR), and the like.

Besides, 7,7,8,8-tetracyanoquinodimethane (abbreviation: TCNQ), 1,4,5,8-naphthalenetetracarboxylic dianhydride (abbreviation: NTCDA), perfluoropentacene, copper hexadecafluorophthalocyanine (abbreviation: F$_{16}$CuPc), N,N'-bis(2,2,3,3,4,4,5,5,6,6,7,7,8,8,8-pentadecafluorooctyl)-1,4,5,8-naphthalenetetracarboxylic diimide (abbreviation: NTCDI-C8F), 3',4'-dibutyl-5,5"-bis(dicyanomethylene)-5,5"-dihydro-2,2':5",2"'-terthiophene (abbreviation: DCMT), a methanofullerene (e.g., [6,6]-phenyl C$_{61}$ butyric acid methyl ester), or the like can be used.

Note that in the case where the substance having a donor property is included in the electron-relay layer 707, the electron-relay layer 707 can be formed by a method such as co-evaporation of the substance having a high electron-transport property and the substance having a donor property.

The hole-injection layer 701, the hole-transport layer 702, the light-emitting layer 703, and the electron-transport layer 704 can be formed using any of the above-described materials.

As described above, the EL layer 102 of this embodiment can be fabricated.

In the above-described light-emitting element, a current flows due to a potential difference generated between the first electrode 103 and the second electrode 108, and holes and electrons recombine in the EL layer 102, which leads to light emission. Then, this light emission is extracted out through one or both of the first electrode 103 and the second electrode 108. One or both of the first electrode 103 and the second electrode 108 thus have a property of transmitting visible light.

Further, the structure of the layers provided between the first electrode 103 and the second electrode 108 is not limited to the above-described structure. A structure other than the above may be employed as long as a light-emitting region in which holes and electrons recombine is provided in a portion away from the first electrode 103 and the second electrode 108 so as to prevent quenching due to proximity of the light-emitting region to metal.

In other words, there is no particular limitation on a stacked structure of the layers. A layer that includes a substance having a high electron-transport property, a substance having a high hole-transport property, a substance having a high electron-injection property, a substance having a high hole-injection property, a bipolar substance (a substance having a high electron-transport property and a high hole-transport property), a hole-blocking material, or the like can be freely combined with a light-emitting layer including any of the heterocyclic compounds according to one embodiment of the present invention as a host material.

With the use of a light-emitting element described in this embodiment, a passive matrix light-emitting device or an active matrix light-emitting device in which driving of the light-emitting element is controlled by a transistor can be manufactured.

In fabrication of an active matrix light-emitting device, there is no particular limitation on the structure of the transistor; for example, a staggered transistor or an inverted staggered transistor can be used as appropriate. In addition, a driver circuit formed over a substrate may be formed with an n-type transistor and a p-type transistor, or with either an n-type transistor or a p-type transistor. Further, there is no particular limitation on the crystallinity of a semiconductor film used for the transistor; for example, an amorphous semiconductor film or a crystalline semiconductor film can be used. As a material of the semiconductor film, a compound semiconductor such as GaAs, InP, SiC, ZnSe, GaN, or SiGe can be used in addition to an elemental substance such as silicon or germanium. An oxide semiconductor such as zinc oxide, tin oxide, magnesium zinc oxide, gallium oxide, or indium oxide, an oxide semiconductor including two or more of the above oxide semiconductors, or the like can be used.

Thus, a light-emitting element can be fabricated using any of the heterocyclic compounds according to one embodiment of the present invention. By use of any of the heterocyclic compounds according to one embodiment of the present invention for a light-emitting element, it is possible to obtain a light-emitting element having low driving voltage, a light-emitting element having high current efficiency, or a light-emitting element having a long lifetime.

Furthermore, a light-emitting device (such as an image display device) using a light-emitting element according to one embodiment of the present invention which is obtained as above can have low power consumption.

Embodiment 3

In Embodiment 3, a light-emitting device having a light-emitting element according to one embodiment of the present invention will be described with reference to FIGS. 2A and 2B. Note that FIG. 2A is a top view illustrating the light-emitting device, and FIG. 2B is a cross-sectional view taken along lines A-B and C-D of FIG. 2A.

The light-emitting device of this embodiment includes a source side driver circuit 401 and a gate side driver circuit 403 which are driver circuit portions, a pixel portion 402, a sealing substrate 404, a sealing material 405, a flexible printed circuit (FPC) 409, and an element substrate 410. A portion enclosed by the sealing material 405 is a space.

A lead wiring 408 is a wiring for transmitting signals that are to be input to the source side driver circuit 401 and the gate side driver circuit 403, and receives a video signal, a clock signal, a start signal, a reset signal, and the like from the FPC 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Figure 2A:
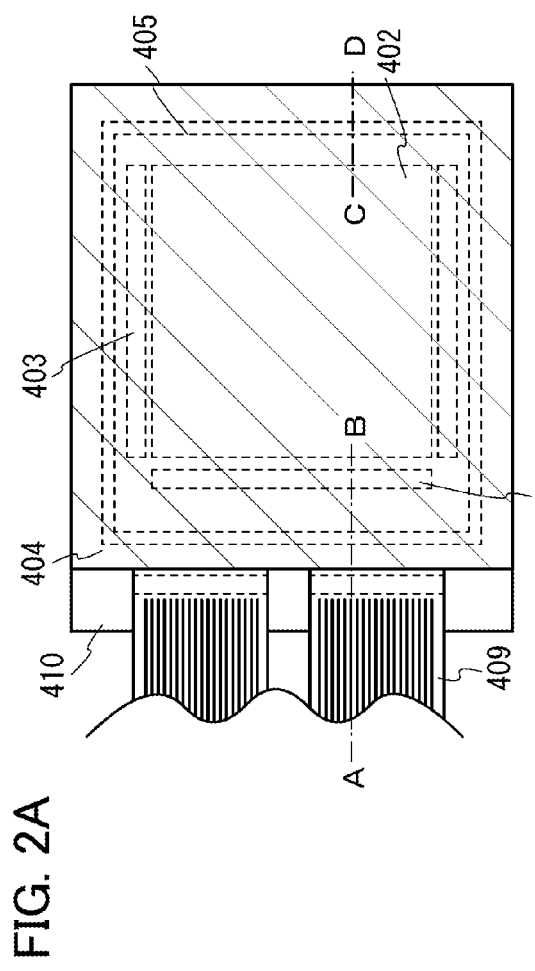
FIGS. 2A and 2B illustrate a light-emitting device according to one embodiment of the present invention.
Figure 2B:
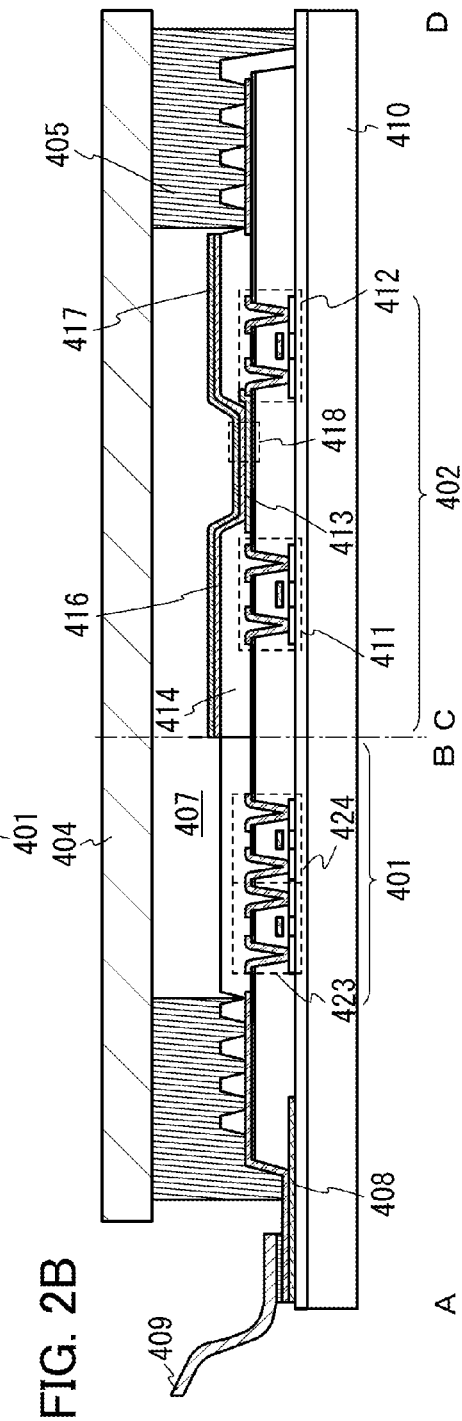

The driver circuit portion and the pixel portion are formed over an element substrate 410 illustrated in FIG. 2A. In FIG. 2B, the source side driver circuit 401 which is the driver circuit portion and one pixel in the pixel portion 402 are illustrated.

Note that as the source side driver circuit 401, a CMOS circuit in which an n-channel TFT 423 and a p-channel TFT 424 are combined is formed. The driver circuit may be any of a variety of circuits formed with TFTs, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413. Here, the insulator 414 is formed by use of a positive type photosensitive acrylic resin film.

In order to improve coverage, the insulator 414 is provided such that either an upper end portion or a lower end portion of the insulator 414 has a curved surface with a curvature. For example, when positive photosensitive acrylic is used as a material for the insulator 414, it is preferable that only an upper end portion of the insulator 414 have a curved surface with a radius of curvature (0.2 μm to 3 μm). For the insulator 414, it is also possible to use either a negative type photosensitive material that becomes insoluble in an etchant by light irradiation or a positive type one that becomes soluble in an etchant by light irradiation.

An EL layer 416 and a second electrode 417 are formed over the first electrode 413. The first electrode, the EL layer, and the second electrode can be formed with materials given in Embodiment 2. In addition, the EL layer 416 includes any of the heterocyclic compounds according to one embodiment of the present invention.

Further, the sealing substrate 404 is attached to the element substrate 410 with the sealing material 405, so that a light-emitting element 418 is provided in a space 407 enclosed by the element substrate 410, the sealing substrate 404, and the sealing material 405. The space 407 is filled with a filler, and may be filled with an inert gas (such as nitrogen or argon) or the sealing material.

Note that an epoxy-based resin is preferably used as the sealing material 405. Such a material preferably allows as little moisture and oxygen as possible to penetrate. As a material used for the sealing substrate 404, a plastic substrate formed of fiberglass-reinforced plastics (FRP), polyvinyl fluoride (PVF), polyester, acrylic, or the like can be used other than a glass substrate or a quartz substrate.

As described above, the active matrix light-emitting device including the light-emitting element according to one embodiment of the present invention can be obtained.

Figure 3A:
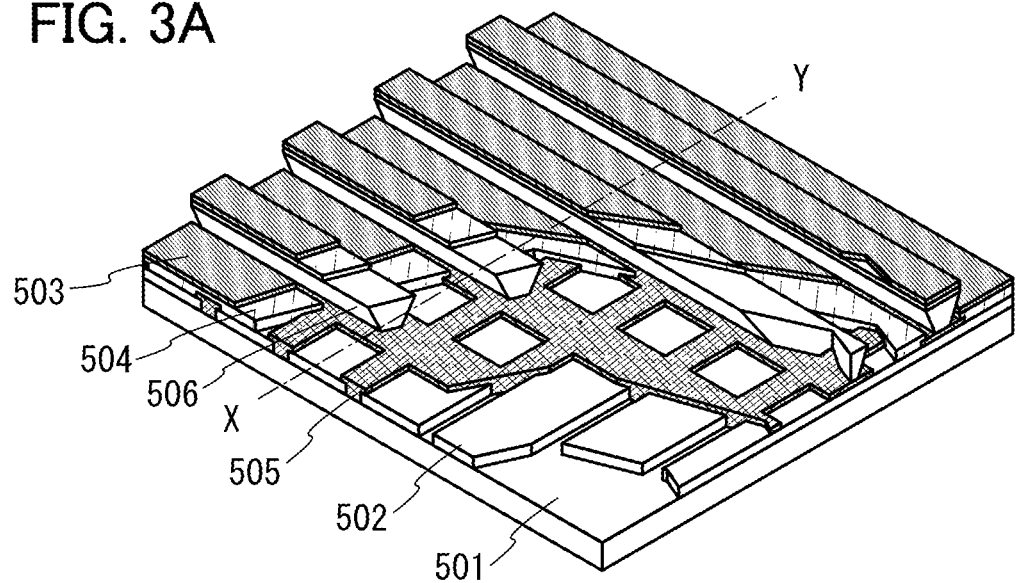
FIGS. 3A and 3B illustrate a light-emitting device according to one embodiment of the present invention.
Figure 3B:
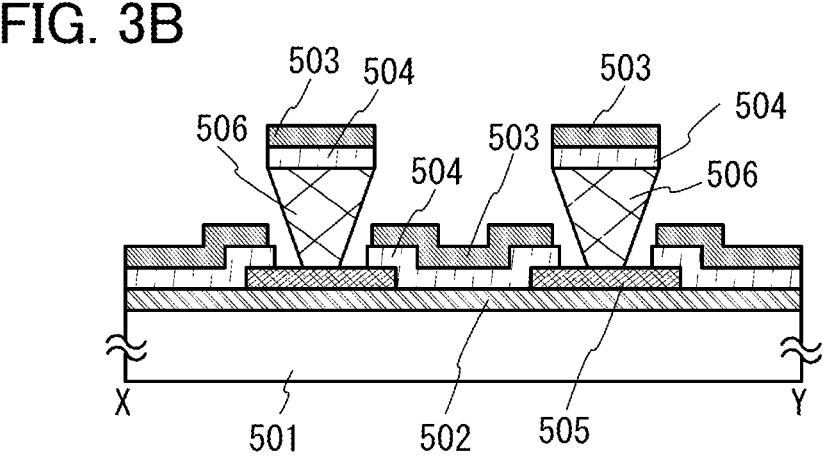

Further, a light-emitting element according to one embodiment of the present invention can be used for a passive matrix light-emitting device as well as the above active matrix light-emitting device. FIGS. 3A and 3B illustrate a perspective view and a cross-sectional view of a passive matrix light-emitting device including a light-emitting element according to one embodiment of the present invention. Note that FIG. 3A is a perspective view of the light-emitting device, and FIG. 3B is a cross-sectional view taken along line X-Y of FIG. 3A.

In FIGS. 3A and 3B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that a distance between both the sidewalls is gradually narrowed toward the surface of the substrate. In other words, a cross section taken along the direction of the short side of the partition layer 506 is trapezoidal, and the base (side in contact with the insulating layer 505) is shorter than the upper side (side not in contact with the insulating layer 505). With the partition layer 506 provided in such a way, a defect of a light-emitting element due to crosstalk or the like can be prevented.

Examples of light-emitting devices to which one embodiment of the present invention is applied are illustrated in FIGS. 22A to 22C. FIG. 22A is a top view illustrating the light-emitting devices, and FIGS. 22B and 22C are cross-sectional views taken along line E-F of FIG. 22A.

Light-emitting devices 900 illustrated in FIGS. 22A to 22C include a light-emitting element 908 (a first electrode 103, an EL layer 102, and a second electrode 108) over a first substrate 901. The light-emitting element 908 can be formed using any of the materials described in Embodiment 2. The EL layer 102 includes any of the heterocyclic compounds according to one embodiment of the present invention.

To the light-emitting devices of this embodiment, any of the following structures can be applied: a structure in which a light-emitting element emits light upward (such a structure is also referred to as a top emission structure); a structure in which a light-emitting element emits light upward and downward (such a structure is also referred to as a dual emission structure); and a structure in which a light-emitting element emits light downward (such a structure is also referred to as a bottom emission structure).

A light-emitting device having a bottom emission structure is illustrated in FIG. 22B.

The light-emitting device illustrated in FIG. 22B has the first electrode 103 over the first substrate 901, the EL layer 102 over the first electrode 103, and the second electrode 108 over the EL layer 102.

A first terminal 903 is electrically connected to an auxiliary wiring 910 and the first electrode 103, and a second terminal 904 is electrically connected to the second electrode 108. Further, an insulating layer 909 is formed between end portions of the first electrode 103 and the second electrode 108 and between the auxiliary wiring 910 and the EL layer 102. Note that although a structure in which the first electrode 103 is formed over the auxiliary wiring 910 is illustrated in FIG. 22B, a structure in which the auxiliary wiring 910 is formed over the first electrode 103 may be possible.

In addition, the first substrate 901 and the second substrate 902 are bonded together by a sealing material 912. Further, a desiccant 911 may be included between the first substrate 901 and the second substrate 902.

Further, the upper and/or lower portions of the first substrate 901 may be provided with a light extraction structure. As the light extraction structure, an uneven structure can be provided at an interface through which light is transmitted from the side having a high refractive index to the side having a low refractive index. A specific example is as follows: as illustrated in FIG. 22B, a light extraction structure 913a with minute unevenness is provided between the light-emitting element 908 having a high refractive index and the first substrate 901 having a lower refractive index, and a light extraction structure 913b with unevenness is provided between the first substrate 901 and the air.

However, in the light-emitting element, unevenness of the first electrode 103 might cause leakage current generation in the EL layer 102 formed over the first electrode 103. Therefore, in this embodiment, a planarization layer 914 having a refractive index higher than or equal to that of the EL layer 102 is provided in contact with the light extraction structure 913a. Accordingly, the first electrode 103 can be a flat film, and the leakage current generation in the EL layer due to the unevenness of the first electrode 103 can be suppressed. Further, because of the light extraction structure 913a at an interface between the planarization layer 914 and the first substrate 901, light which cannot be extracted to the air due to total reflection can be reduced, so that the light extraction efficiency of the light-emitting device can be increased.

The present invention is not limited to the structure in which the first substrate 901, the light extraction structure 913a, and the light extraction structure 913b are different components as in FIG. 22B. Two or all of these may be formed as one component. The light extraction structure 913a may be all formed inside a sealing region.

A light-emitting device having a top emission structure is illustrated in FIG. 22C.

The light-emitting device illustrated in FIG. 22C has the second electrode 108 over the first substrate 901, the EL layer 102 over the second electrode 108, and the first electrode 103 over the EL layer 102.

The first terminal 903 is electrically connected to the second electrode 108, and the second terminal 904 is electrically connected to the first electrode 103. Further, the insulating layer 909 is formed between end portions of the first electrode 103 and the second electrode 108.

In addition, the first substrate 901 and the second substrate 902 are bonded together by the sealing material 912. Further, an auxiliary wiring may be formed over the first electrode 103. Furthermore, the desiccant 911 may be included between the first substrate 901 and the second substrate 902. The desiccant 911 is preferably provided at a position that does not overlap a light-emitting region of a light-emitting element. Alternatively, a desiccant that transmits light from the light-emitting element is preferably used.

Although the light-emitting device 900 illustrated in FIG. 22A is octagonal, the present invention is not limited to this shape. The light-emitting device 900 and the light-emitting element 908 may have other polygonal shapes or a shape having a curve. As the shape of the light-emitting device 900, a triangle, a quadrangle, a regular hexagon, or the like is particularly preferred. The reason for this is that such a shape allows a plurality of light-emitting devices 900 to be provided in a limited area without a space therebetween, and also because such a shape enables effective use of the limited substrate area for formation of the light-emitting device 900. Further, the number of elements formed over the substrate is not limited to one and a plurality of elements may be provided.

As materials of the first substrate 901 and the second substrate 902, a material having a light-transmitting property, such as glass, quartz, or an organic resin can be used. At least one of the first substrate 901 and the second substrate 902 transmits light emitted from the light-emitting element.

In the case where an organic resin is used for the substrates, for example, any of the following can be used as the organic resin: polyester resins such as polyethylene terephthalate (PET) and polyethylene naphthalate (PEN), a polyacrylonitrile resin, a polyimide resin, a polymethylmethacrylate resin, a polycarbonate (PC) resin, a polyethersulfone (PES) resin, a polyamide resin, a cycloolefin resin, a polystyrene resin, a polyamide imide resin, a polyvinylchloride resin, and the like. A substrate in which a glass fiber is impregnated with an organic resin or a substrate in which an inorganic filler is mixed with an organic resin can also be used.

Thus, the light-emitting device to which one embodiment of the present invention is applied can be obtained.

The light-emitting devices described in this embodiment are formed using a light-emitting element according to one embodiment of the present invention, and accordingly, the light-emitting devices have low power consumption.

Note that this embodiment can be implemented in appropriate combination with any of the other embodiments.

Embodiment 4

In this embodiment, with reference to FIGS. 4A to 4E and FIGS. 5A and 5B, description is given of examples of a variety of electronic devices and lighting devices that are each completed by use of a light-emitting device according to one embodiment of the present invention.

Examples of the electronic devices are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pachinko machines, and the like.

An electronic device or a lighting device that has a light-emitting portion with a curved surface can be realized with a light-emitting element including any of the heterocyclic compounds according to one embodiment of the present invention, which is fabricated over a substrate having flexibility.

In addition, an electronic device or a lighting device that has a see-through light-emitting portion can be realized with a light-emitting element including any of the heterocyclic compounds according to one embodiment of the present invention, in which a pair of electrodes is formed using a material having a property of transmitting visible light.

Further, a light-emitting device to which one embodiment of the present invention is applied can also be applied to a lighting device for motor vehicles, examples of which are lighting devices for a dashboard, a windshield, a ceiling, and the like.

Figure 4A:
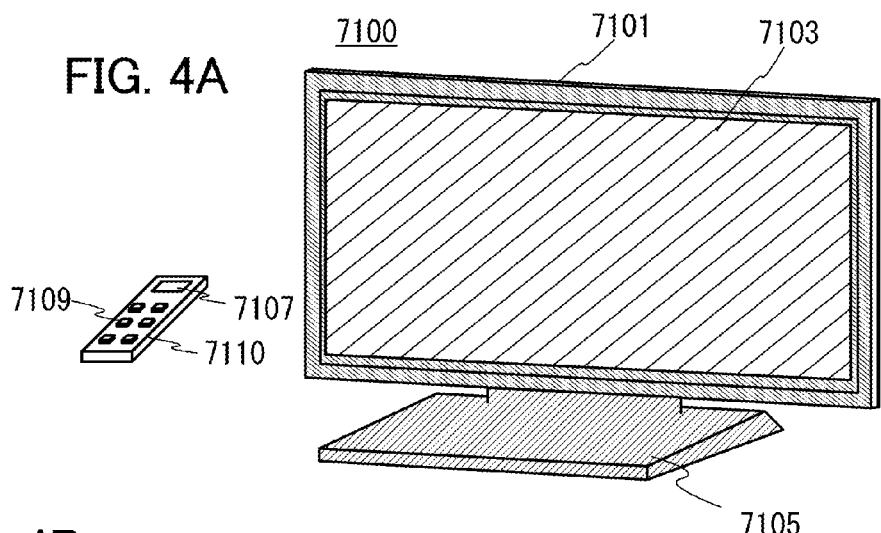
FIGS. 4A to 4E each illustrate an electronic device according to one embodiment of the present invention.

In FIG. 4A, an example of a television device is illustrated. In a television device 7100, a display portion 7103 is incorporated in a housing 7101. The display portion 7103 is capable of displaying images, and the light-emitting device can be used for the display portion 7103. In addition, here, the housing 7101 is supported by a stand 7105.

The television device 7100 can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 4B:
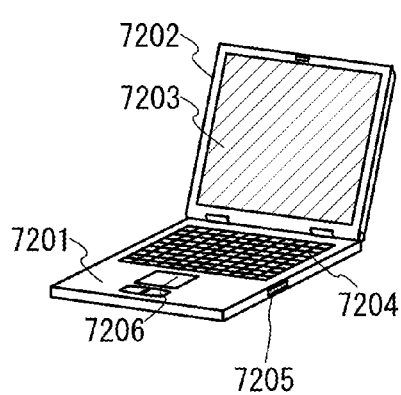

In FIG. 4B, a computer is illustrated, which includes a main body 7201, a housing 7202, a display portion 7203, a keyboard 7204, an external connection port 7205, a pointing device 7206, and the like. This computer is manufactured with the use of the light-emitting device for the display portion 7203.

Figure 4C:
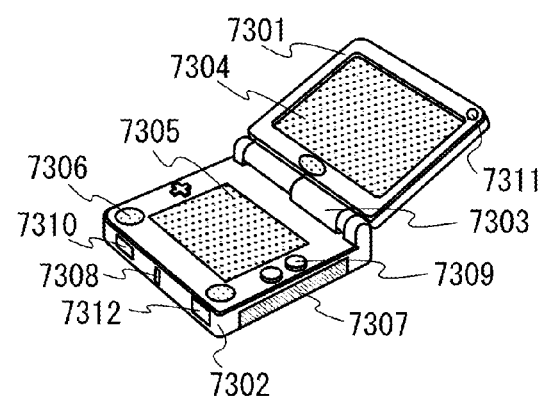

In FIG. 4C, a portable amusement machine is illustrated, which includes two housings, a housing 7301 and a housing 7302, connected with a joint portion 7303 so that the portable amusement machine can be opened or closed. A display portion 7304 is incorporated in the housing 7301 and a display portion 7305 is incorporated in the housing 7302. In addition, the portable amusement machine illustrated in FIG. 4C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substances, sound, time, hardness, electric field, current, voltage, electric power, radiation, flow rate, humidity, gradient, oscillation, odor, or infrared rays), and a microphone 7312), and the like. It is needless to say that the structure of the portable amusement machine is not limited to the above as long as the light-emitting device is used for at least either the display portion 7304 or the display portion 7305, or both, and may include other accessories as appropriate. The portable amusement machine illustrated in FIG. 4C has a function of reading out a program or data stored in a storage medium to display it on the display portion, and a function of sharing information with another portable amusement machine by wireless communication. The portable amusement machine illustrated in FIG. 4C can have a variety of functions without limitation to the above.

Figure 4D:
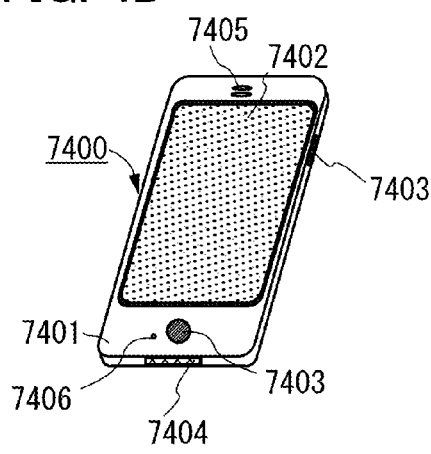

In FIG. 4D, an example of a cellular phone is illustrated. A cellular phone 7400 is provided with a display portion 7402 incorporated in a housing 7401, operation buttons 7403, an external connection port 7404, a speaker 7405, a microphone 7406, and the like. Note that the cellular phone 7400 is manufactured with the use of the light-emitting device for the display portion 7402.

When the display portion 7402 of the cellular phone 7400 illustrated in FIG. 4D is touched with a finger or the like, data can be input to the cellular phone 7400. Further, operations such as making a phone call and writing e-mail can be performed by touch on the display portion 7402 with a finger or the like.

There are mainly three screen modes of the display portion 7402. The first mode is a display mode mainly for displaying an image. The second mode is an input mode mainly for inputting information such as a character. The third mode is a display-and-input mode in which two modes of the display mode and the input mode are mixed.

For example, in the case where a phone call is made or e-mail is written, the character input mode mainly for inputting a character is selected for the display portion 7402 so that a character displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touch on the display portion 7402 or operation with the operation buttons 7403 of the housing 7401. The screen modes can also be switched depending on kinds of images displayed on the display portion 7402. For example, when a signal for an image to be displayed on the display portion is for moving images, the screen mode is switched to the display mode; when the signal is for text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, so that personal identification can be performed. Furthermore, by provision of a backlight or a sensing light source emitting near-infrared light for the display portion, an image of a finger vein, a palm vein, or the like can also be taken.

Figure 4E:
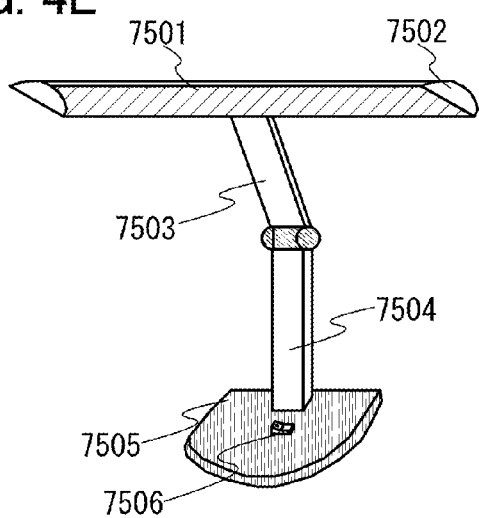

In FIG. 4E, a desk lamp is illustrated, which includes a lighting portion 7501, a shade 7502, an adjustable arm 7503, a support 7504, a base 7505, and a power switch 7506. The desk lamp is manufactured with the use of the light-emitting device for the lighting portion 7501. Note that the "lighting device" also includes ceiling lights, wall lights, and the like.

Figure 5A:
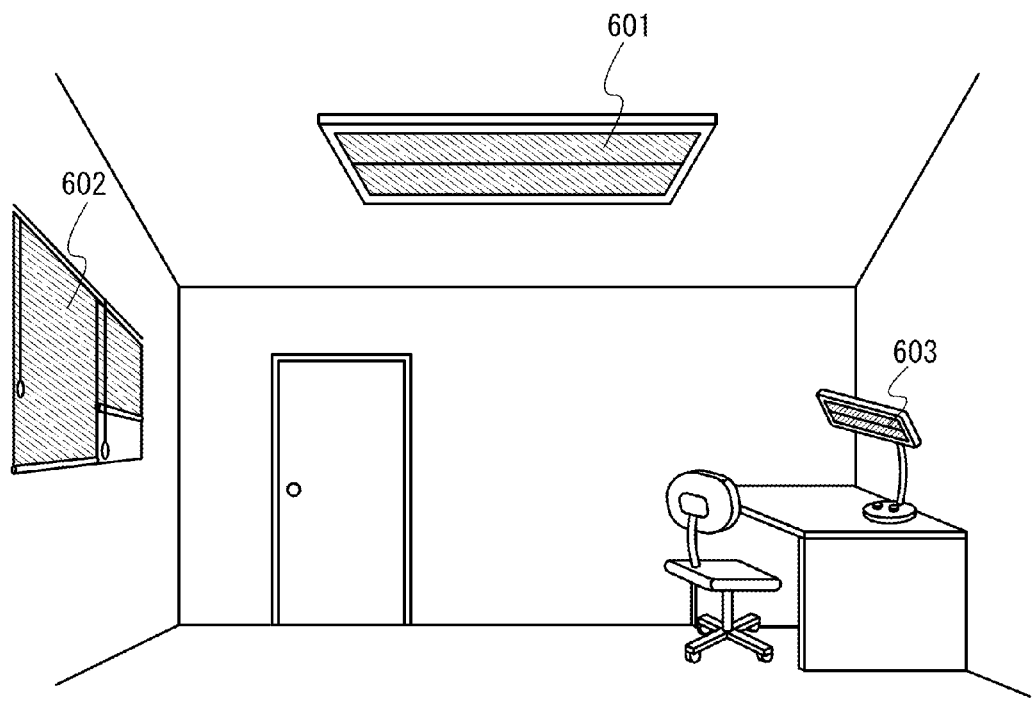
FIGS. 5A and 5B illustrate lighting devices according to one embodiment of the present invention.

In FIG. 5A, an example in which the light-emitting device is used for an interior lighting device 601 is illustrated. Since the light-emitting device can have a larger area, it can be used as a lighting device having a large area. Furthermore, the light-emitting device can be used as a roll-type lighting device 602. As illustrated in FIG. 5A, a desk lamp 603 described with reference to FIG. 4E may also be used in a room provided with the interior lighting device 601.

Figure 5B:
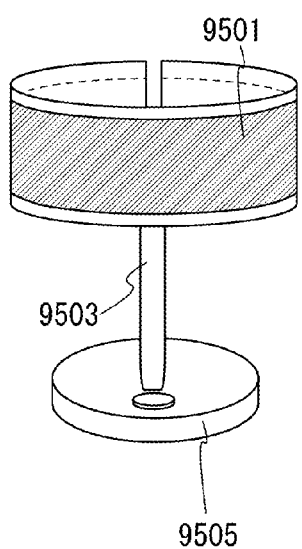

In FIG. 5B, an example of another lighting device is illustrated. A table lamp illustrated in FIG. 5B includes a lighting portion 9501, a support 9503, a support base 9505, and the like. The lighting portion 9501 includes any of the heterocyclic compounds according to one embodiment of the present invention. Thus, a lighting device that has a curved surface or a lighting portion that can be flexibly bent can be provided by fabrication of a light-emitting element over a substrate having flexibility. Such use of a flexible light-emitting device for a lighting device enables a place having a curved surface, such as the ceiling or dashboard of a motor vehicle, to be provided with the lighting device, as well as increases the degree of freedom in design of the lighting device.

In the above-described manner, electronic devices or lighting devices can be obtained by application of the light-emitting device. Application range of the light-emitting device is so wide that the light-emitting device can be applied to electronic devices in a variety of fields.

Note that the structure described in this embodiment can be combined with any of the structures described in the other embodiments as appropriate.

Example 1

Synthesis Example 1

This example gives specific descriptions of a method of synthesizing 6-[3-(dibenzothiophen-4-yl)phenyl]dibenzo[f,h]quinoxaline (abbreviation: 6mDBTPDBq-II) represented by the structural formula (101) in Embodiment 1. A structure of 6mDBTPDBq-II is illustrated below.

[Chemical Formula 28]

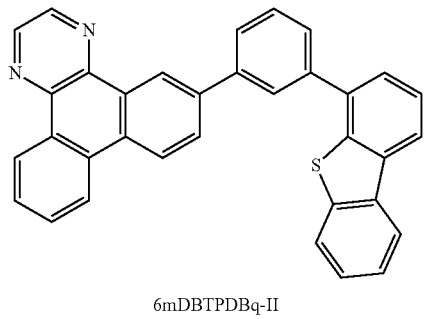

6mDBTPDBq-II

Step 1: Method of Synthesizing 6-Iododibenzo[f,h]quinoxaline

The synthesis scheme of Step 1 is illustrated in (B-1).

[Chemical Formula 29]

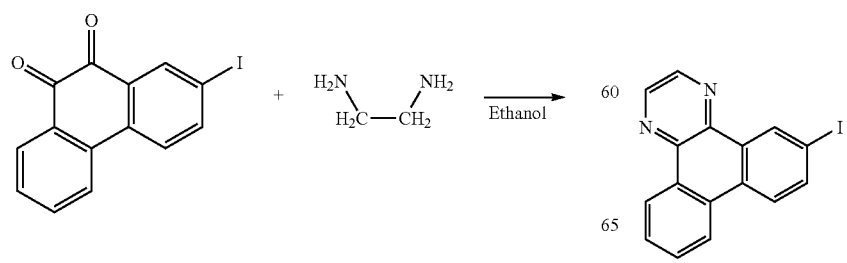

(B-1)

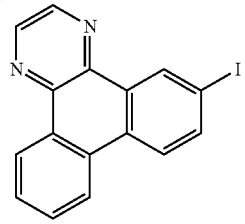

In a 200 mL three-neck flask, 10.6 g (32 mmol) of 2-iodo-9,10-phenanthrenedione, 3.7 g (62 mmol) of ethylenediamine, and 100 mL of ethanol were reacted by being heated and stirred while being refluxed under a nitrogen atmosphere for 5 hours. After the reaction, this reaction mixture solution was filtered and washed with water and toluene in this order. The obtained residue was purified by silica gel column chromatography. At this time, a mixed solution of toluene and hexane was used as a developing solvent for the chromatography. The obtained fraction was concentrated, and toluene was added thereto. The mixture was irradiated with ultrasonic waves and then recrystallized to give 3.0 g of a white powder that was the object of the synthesis in a yield of 26%.

The obtained compound in Step 1 was subjected to nuclear magnetic resonance (NMR) spectroscopy. The measurement data are shown below.

$^1$H NMR (CDCl$_3$, 300 MHz): δ (ppm)=7.77-7.82 (m, 2H), 8.07 (dd, J=9.0 Hz, J=2.1 Hz, 1H), 8.34 (d, J=8.7 Hz, 1H), 8.68 (dd, J=7.2 Hz, J=2.1 Hz, 1H), 8.92 (dd, J=6.3 Hz, J=1.8 Hz, 2H), 9.22 (dd, J=7.2 Hz, J=1.5 Hz, 1H), 9.59 (d, J=1.5 Hz, 1H).

Figure 7A:
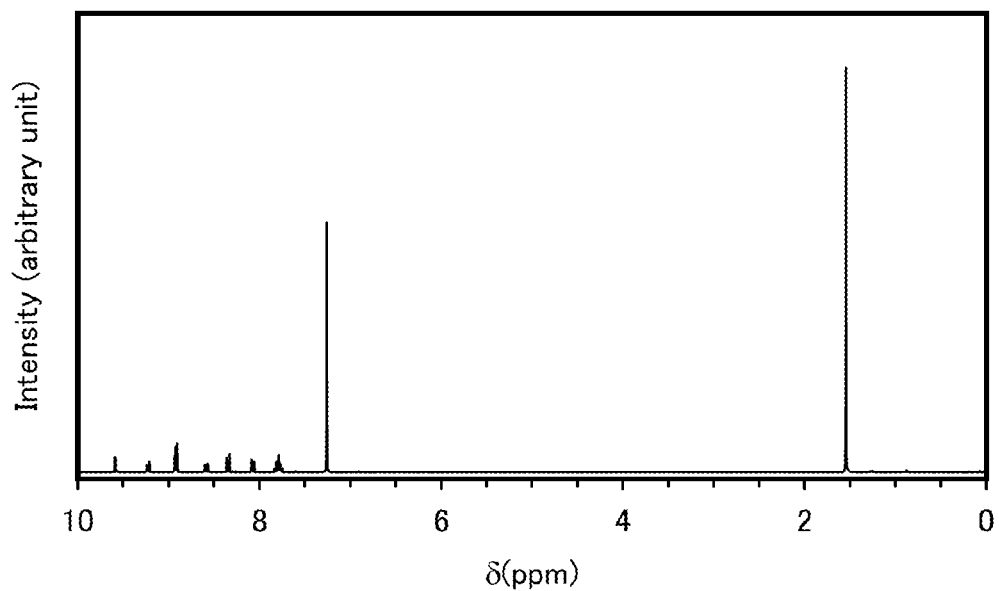
FIGS. 7A and 7B show $^1$H NMR charts of 6-iododibenzo[f,h]quinoxaline.
Figure 7B:
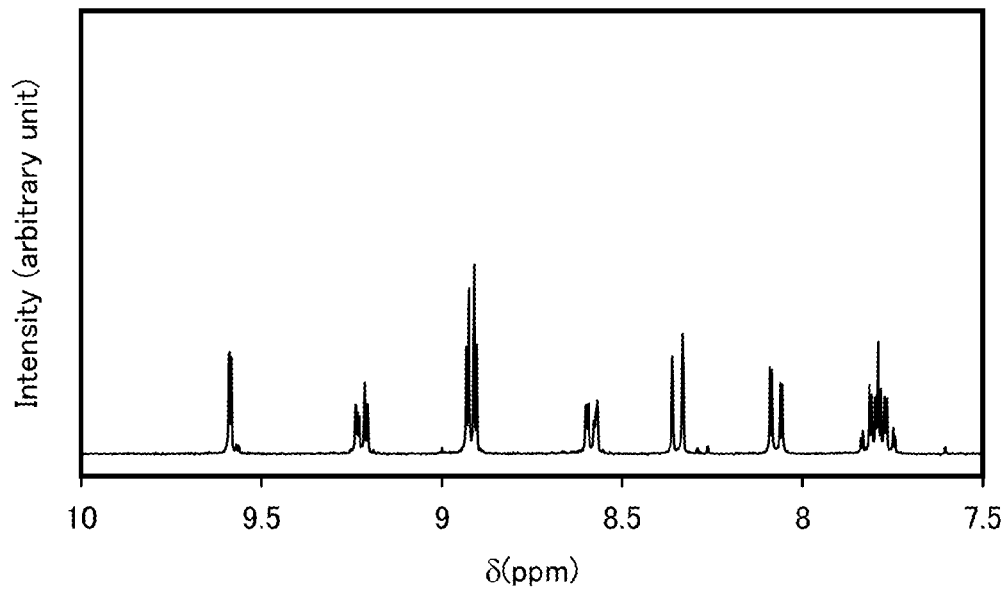

FIGS. 7A and 7B show the $^1$H NMR charts. Note that FIG. 7B is a chart showing an enlarged part of FIG. 7A in the range of 7.5 ppm to 10.0 ppm. The measurement results confirmed that the object of the synthesis, 6-iododibenzo[f,h]quinoxaline, was obtained.

The molecular weight of the above compound was measured by a GC-MS detector (ITQ1100 ion trap GC-MS system, manufactured by Thermo Fisher Scientific Inc.). With this, a main peak at a molecular weight of 481.8 (the mode was EI+) was detected, and thus it was confirmed that the object of the synthesis, 6-iododibenzo[f,h]quinoxaline, was obtained.

Step 2: Method of Synthesizing 6-[3-(Dibenzothiophen-4-yl)phenyl]dibenzo[f,h]quinoxaline (abbreviation: 6mDBTPDBq-II)

The synthesis scheme of Step 2 is illustrated in (B-2).

[Chemical Formula 30]

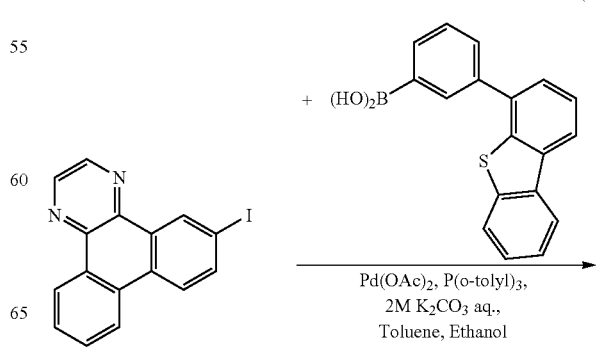

(B-2)

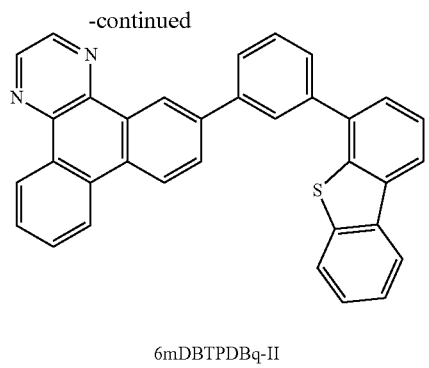

6mDBTPDBq-II

In a 200 mL three-neck flask, a mixture of 1.1 g (3.0 mmol) of 6-iododibenzo[f,h]quinoxaline, 1.0 g (3.3 mmol) of 3-(dibenzothiophen-4-yl)phenylboronic acid, 6.0 mg (30 μmol) of palladium(II)acetate, 9.0 mg (30 μmol) of tri(ortho-tolyl)phosphine, 30 mL of toluene, 3 mL of ethanol, and 3 mL of an aqueous solution of potassium carbonate (2 mol/L) was degassed while being stirred under reduced pressure, and was then reacted by being heated and stirred under a nitrogen atmosphere at 85° C. for 40 hours.

After the reaction, this reaction mixture solution was filtered and washed with water and toluene in this order. The obtained residue was purified by silica gel column chromatography. At this time, toluene was used as a developing solvent for the chromatography. The obtained fraction was concentrated, and toluene was added thereto. The mixture was irradiated with ultrasonic waves and then recrystallized to give 1.1 g of a pale yellow powder that was the object of the synthesis in a yield of 75%.

The Rf values of the object of the synthesis and 6-iododibenzo[f,h]quinoxaline were respectively 0.33 and 0.72, which were found by silica gel thin layer chromatography (TLC) (with a developing solvent of ethyl acetate and hexane in a ratio of 1:5).

Nuclear magnetic resonance (NMR) spectroscopy identified the compound obtained in Step 2 as 6-[3-(dibenzothiophen-4-yl)phenyl]dibenzo[f,h]quinoxaline (abbreviation: 6mDBTPDBq-II), which was the object of the synthesis.

$^1$H NMR data of the obtained compound are as follows: $^1$H NMR (CDCl$_3$, 300 MHz): δ (ppm)=7.47-7.47 (m, 2H), 7.59-7.86 (m, 7H), 7.95 (d, J=7.8 Hz, 1H), 8.14-8.23 (m, 4H), 8.66 (d, J=7.8 Hz, 1H), 8.73 (d, J=8.7 Hz, 1H), 8.91 (s, 2H), 9.26 (d, J=8.4 Hz, 1H), 9.59 (s, 1H).

Figure 8A:
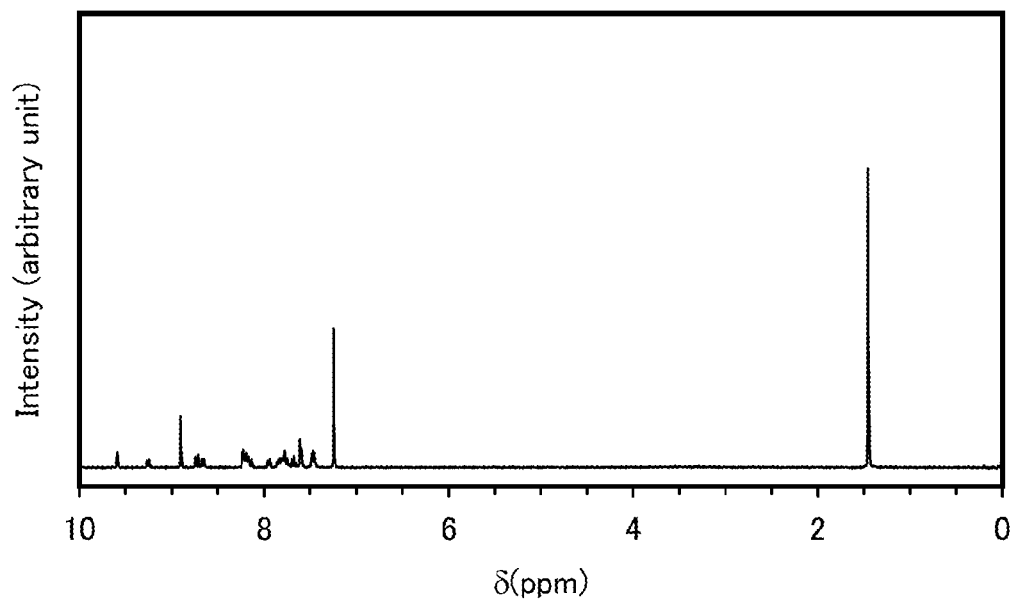
FIGS. 8A and 8B show $^1$H NMR charts of 6-[3-(dibenzothiophen-4-yl)phenyl]dibenzo[f,h]quinoxaline (abbreviation: 6mDBTPDBq-II)
Figure 8B:
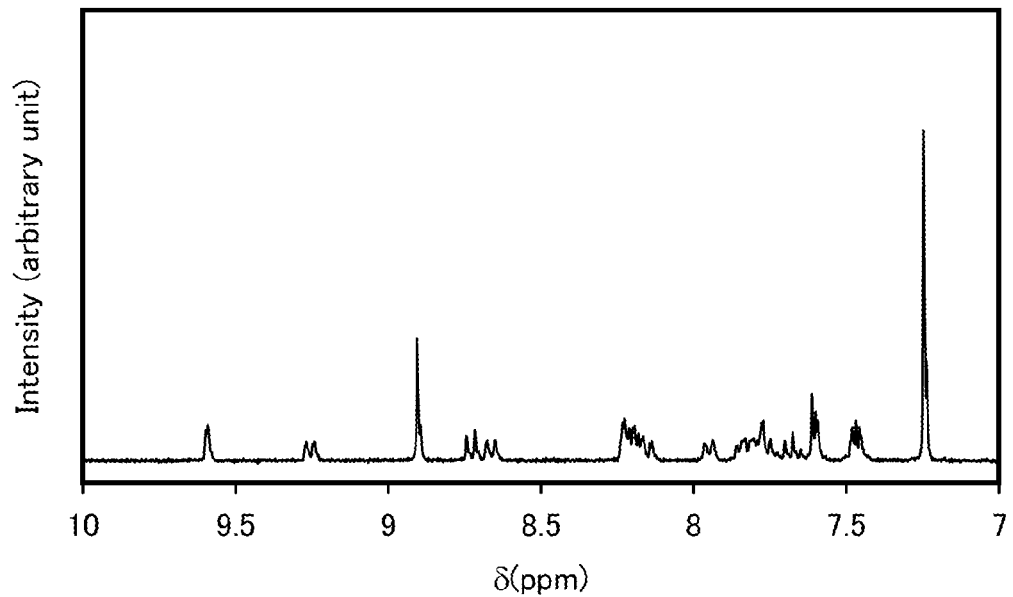

FIGS. 8A and 8B show the $^1$H NMR charts. Note that FIG. 8B is a chart showing an enlarged part of FIG. 8A in the range of 7.0 ppm to 10.0 ppm. The measurement results confirmed that the object of the synthesis, 6mDBTPDBq-II, was obtained.

The molecular weight of the above compound was measured by a TOF-MS detector (Waters Micromass LCT Premier, manufactured by Waters). A mixture solution containing acetonitrile and 0.1% of a formic acid solution (a mixture ratio of acetonitrile to the formic acid solution, 80:20 (volume ratio)) was used as a solvent. According to the measurement, it was confirmed that a main peak with a molecular weight of 562 (the mode was ES+) was detected and 6mDBTPDBq-II that was the object of the synthesis was obtained.

Figure 9A:
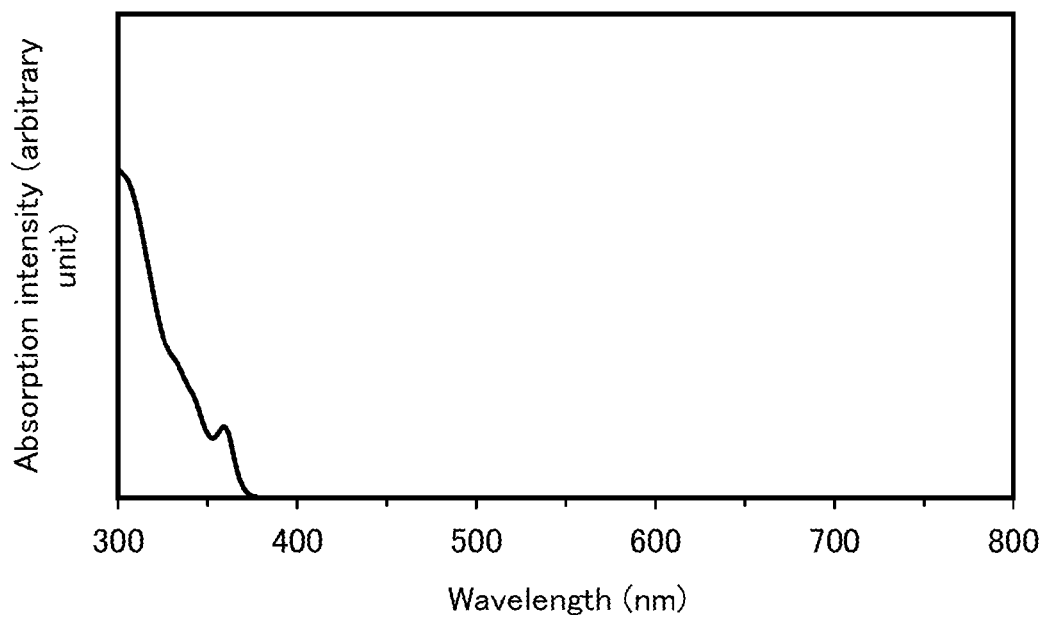
FIGS. 9A and 9B show respectively an absorption spectrum and an emission spectrum of 6mDBTPDBq-II in a toluene solution of 6mDBTPDBq-II.
Figure 9B:
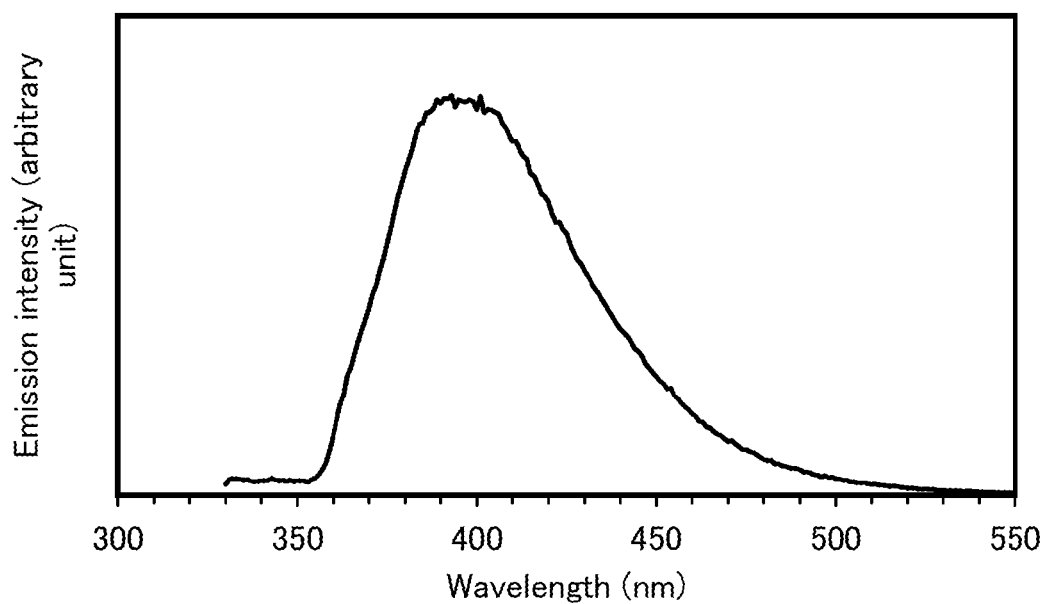
Figure 10A:
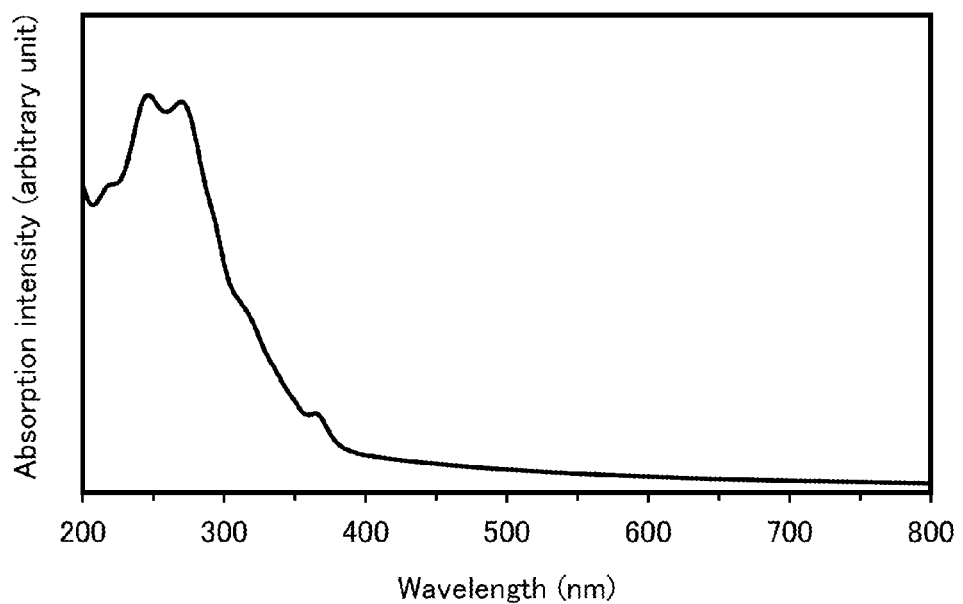
FIGS. 10A and 10B show respectively an absorption spectrum and an emission spectrum of a thin film of 6mDBTPDBq-II.
Figure 10B:
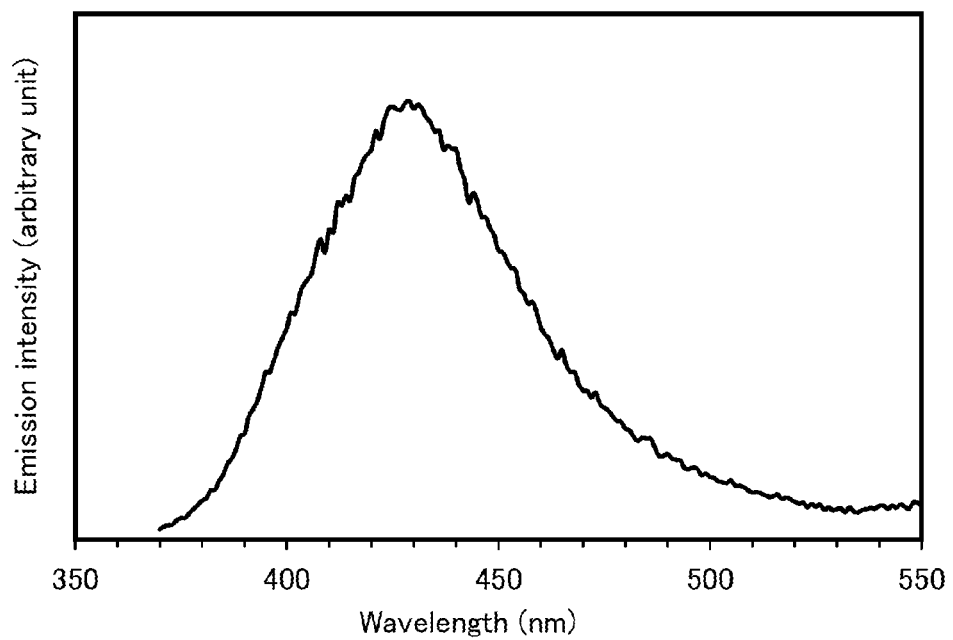

Further, FIG. 9A shows an absorption spectrum of 6mDBTPDBq-II in a toluene solution of 6mDBTPDBq-II, and FIG. 9B shows an emission spectrum thereof. FIG. 10A shows an absorption spectrum of a thin film of 6mDBTPDBq-II, and FIG. 10B shows an emission spectrum thereof. The absorption spectrum was measured using an ultraviolet-visible spectrophotometer (V-550, produced by JASCO Corporation). The measurements were performed with samples prepared in such a way that the solution was put in a quartz cell and the thin film was obtained by evaporation onto a quartz substrate. The figures show the absorption spectrum of the solution which was obtained by subtracting the absorption spectra of quartz and toluene from the absorption spectra of quartz and the solution, and the absorption spectrum of the thin film which was obtained by subtracting the absorption spectrum of a quartz substrate from the absorption spectra of the quartz substrate and the thin film. In each of FIG. 9A and FIG. 10A, the horizontal axis represents wavelength (nm) and the vertical axis represents absorption intensity (arbitrary unit). In each of FIG. 9B and FIG. 10B, the horizontal axis represents wavelength (nm) and the vertical axis represents emission intensity (arbitrary unit). In the case of the toluene solution, an absorption peak was observed at around 358 nm, and an emission wavelength peak was 395 nm (at an excitation wavelength of 290 nm). In the case of the thin film, an absorption peak was observed at around 365 nm, and an emission wavelength peak was 429 nm (at an excitation wavelength of 366 nm).

From emission wavelengths, it was found that 6mDBTPDBq-II emitted blue to bluish purple light and thus was able to be used as a light-emitting material for blue to bluish purple light. Further, it was also found that 6mDBTPDBq-II was able to be used as a host material of a fluorescent light-emitting material which emits light having a longer wavelength than light emitted by 6mDBTPDBq-II.

Further, by measurement with a photoelectron spectrometer (AC-2, manufactured by Riken Keiki, Co., Ltd.) in the air, the ionization potential of 6mDBTPDBq-II in the thin film was found to be 5.91 eV. As a result, the HOMO level was found to be −5.91 eV. The absorption edge was obtained from Tauc plot assuming direct transition with the absorption spectrum data of the thin film of 6mDBTPDBq-II. The absorption edge was estimated as an optical energy gap, and the energy gap was 3.23 eV. From the obtained value of the energy gap and the HOMO level, the LUMO level was −2.68 eV.

Example 2

Figure 6:
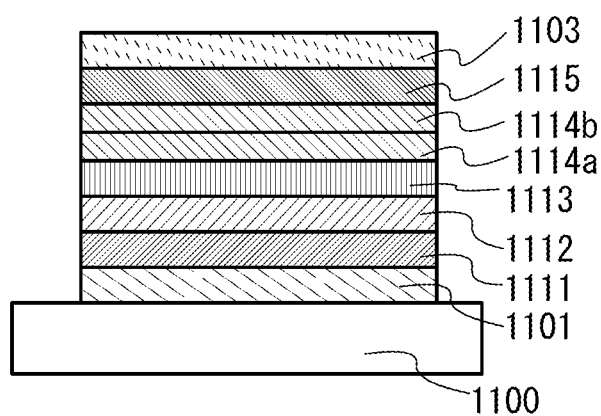
FIG. 6 illustrates a light-emitting element of Examples.

In this example, a light-emitting element according to one embodiment of the present invention is described referring to FIG. 6. Chemical formulae of materials used in this example are illustrated below.

[Chemical Formula 31]

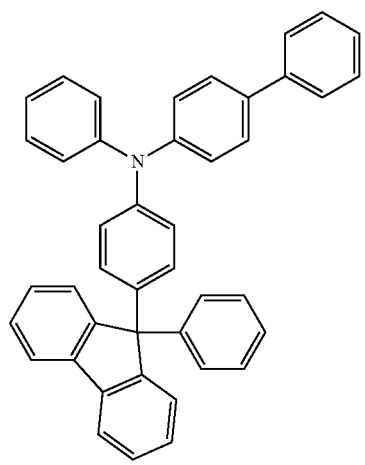

BPAFLP

-continued

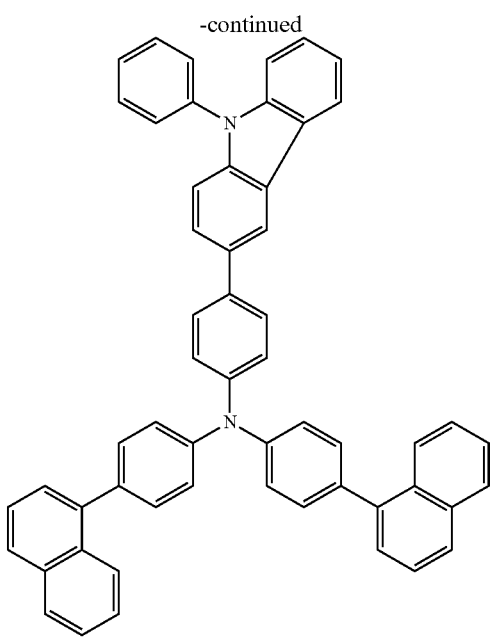

PCBNBB

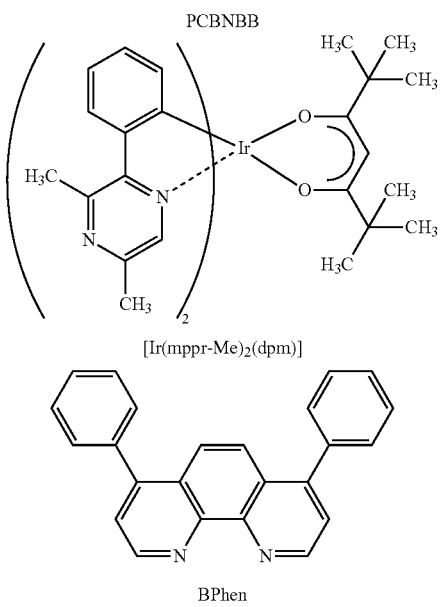

[Ir(mppr-Me)₂(dpm)]

BPhen

The ways how a light-emitting element 1 and a light-emitting element 2 were fabricated are described hereinbelow.

(Light-Emitting Element 1)

First, a film of indium tin oxide containing silicon oxide (ITSO) was formed over a glass substrate 1100 by a sputtering method, so that a first electrode 1101 was formed. Note that its thickness was set to 110 nm and the electrode area was set to 2 mm×2 mm. Here, the first electrode 1101 is an electrode that functions as an anode of the light-emitting element.

Then, in pretreatment for forming the light-emitting elements over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Then, the substrate 1100 over which the first electrode 1101 was formed was fixed to a substrate holder provided in a vacuum evaporation apparatus so that the surface on which the first electrode 1101 was formed faced downward. The pressure in the vacuum evaporation apparatus was reduced to about $10^{-4}$ Pa. After that, over the first electrode 1101, 4-phenyl-4'-(9-phenylfluoren-9-yl)triphenylamine (abbreviation: BPAFLP) and molybdenum(VI) oxide were co-evaporated by an evaporation method using resistance heating, so that a hole-injection layer 1111 was formed. The thickness of the hole-injection layer 1111 was set to 40 nm, and the weight ratio of BPAFLP to molybdenum oxide was adjusted to 4:2 (=BPAFLP:molybdenum oxide). Note that the co-evaporation method refers to an evaporation method in which evaporation is carried out from a plurality of evaporation sources at the same time in one treatment chamber.

Next, over the hole-injection layer 1111, a BPAFLP film was formed to a thickness of 20 nm, so that a hole-transport layer 1112 was formed.

Further, 6-[3-(dibenzothiophen-4-yl)phenyl]dibenzo[f,h]quinoxaline (abbreviation: 6mDBTPDBq-II) synthesized in Example 1, 4,4'-di(1-naphthyl)-4"-(9-phenyl-9H-carbazol-3-yl)triphenylamine (abbreviation: PCBNBB), and (dipivaloylmethanato)bis(3,5-dimethyl-2-phenylpyrazinato)iridium(III) (abbreviation: [Ir(mppr-Me)₂(dpm)]) were co-evaporated to form a light-emitting layer 1113 over the hole-transport layer 1112. The weight ratio of 6mDBTPDBq-II to PCBNBB and [Ir(mppr-Me)₂(dpm)] was adjusted to 0.8:0.2:0.05 (=6mDBTPDBq-II:PCBNBB:[Ir(mppr-Me)₂(dpm)]). The thickness of the light-emitting layer 1113 was set to 40 nm.

Further, a 6mDBTPDBq-II film was formed to a thickness of 10 nm over the light-emitting layer 1113, so that a first electron-transport layer 1114a was formed.

Then, a film of bathophenanthroline (abbreviation: BPhen) was formed to a thickness of 20 nm over the first electron-transport layer 1114a, so that a second electron-transport layer 1114b was formed.

Further, a film of lithium fluoride (LiF) was formed to a thickness of 1 nm over the second electron-transport layer 1114b using evaporation, so that an electron-injection layer 1115 was formed.

Lastly, an aluminum film was formed to a thickness of 200 nm using evaporation as the second electrode 1103 functioning as a cathode. Thus, the light-emitting element 1 of this example was fabricated.

Note that, in the above evaporation process, a resistance heating method was used for evaporation.

(Light-Emitting Element 2)

The light-emitting layer 1113 of the light-emitting element 2 was formed by co-evaporation of 6mDBTPDBq-II and [Ir(mppr-Me)₂(dpm)]. The weight ratio of 6mDBTPDBq-II to [Ir(mppr-Me)₂(dpm)] was adjusted to 1:0.05 (=6mDBTPDBq-II:[Ir(mppr-Me)₂(dpm)]). The thickness of the light-emitting layer 1113 was set to 40 nm. The components other than the light-emitting layer 1113 were formed in the same way as those of the light-emitting element 1.

Element structures of the light-emitting element 1 and the light-emitting element 2 obtained as described above is shown in Table 1.

TABLE 1

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 1 | ITSO 110 nm | BPAFLP:MoOx (= 4:2) 40 nm | BPAFLP 20 nm | 6mDBTPDBq-II:PCBNBB:[Ir(mppr-Me)$_2$(dpm)] (= 0.8:0.2:0.05) 40 nm | 6mDBTPDBq-II 10 nm | BPhen 20 nm | LiF 1 nm | Al 200 nm |
| Light-emitting element 2 | ITSO 110 nm | BPAFLP:MoOx (= 4:2) 40 nm | BPAFLP 20 nm | 6mDBTPDBq-II:[Ir(mppr-Me)$_2$(dpm)] (= 1:0.05) 40 nm | 6mDBTPDBq-II 10 nm | BPhen 20 nm | LiF 1 nm | Al 200 nm |

In a glove box containing a nitrogen atmosphere, the light-emitting element 1 and the light-emitting element 2 were sealed with a glass substrate so as not to be exposed to the air. Then, operation characteristics of these elements were measured. Note that the measurements were carried out at room temperature (in the atmosphere kept at 25° C.).

Figure 11:
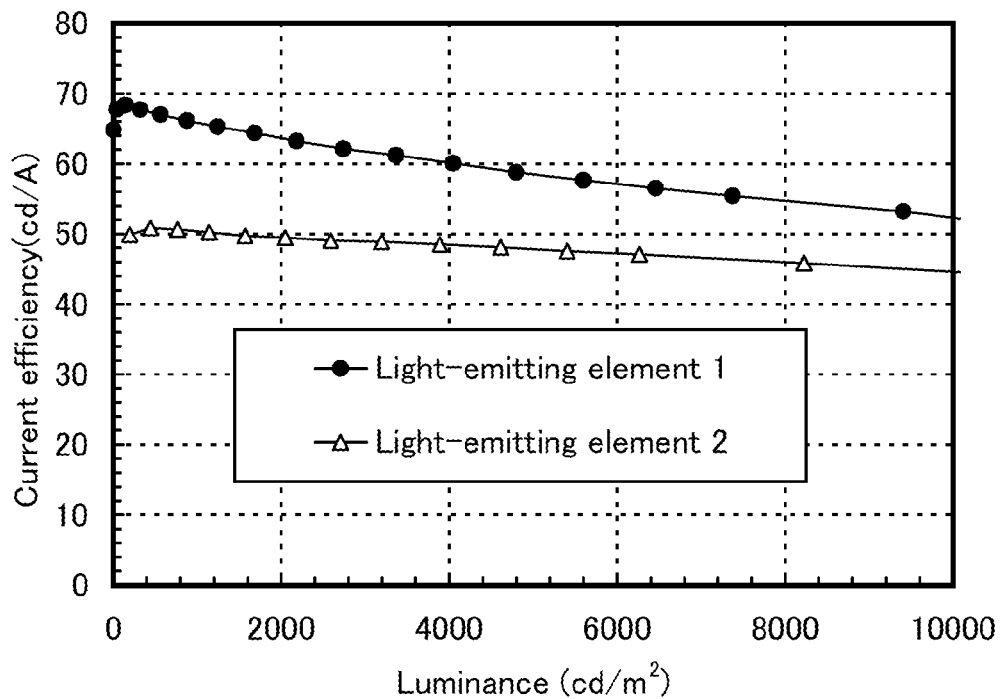
FIG. 11 shows current efficiency versus luminance characteristics of light-emitting elements of Example 2.
Figure 12:
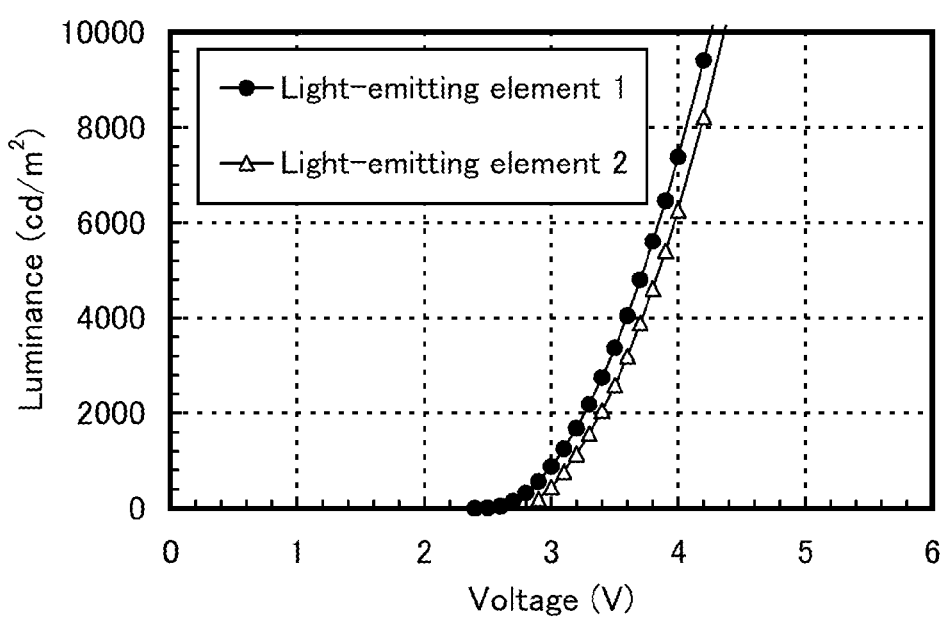
FIG. 12 shows luminance versus voltage characteristics of light-emitting elements of Example 2.
Figure 13:
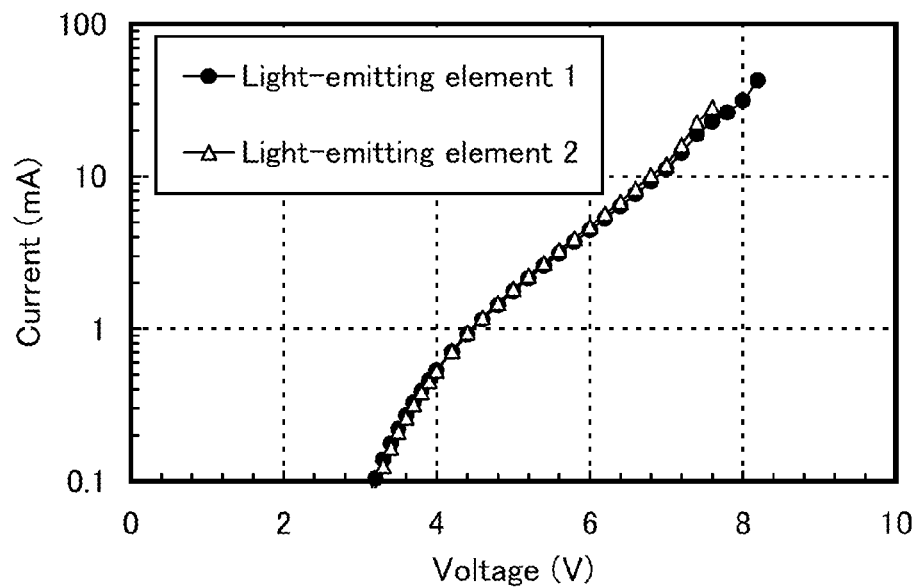
FIG. 13 shows current versus voltage characteristics of light-emitting elements of Example 2.
Figure 14:
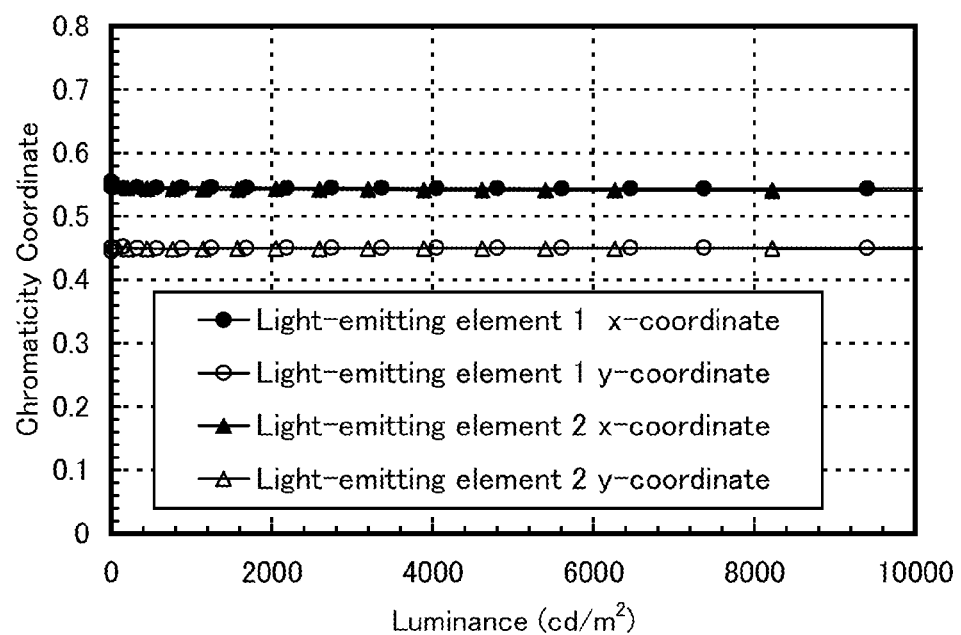
FIG. 14 shows chromaticity coordinate versus luminance characteristics of light-emitting elements of Example 2.
Figure 15:
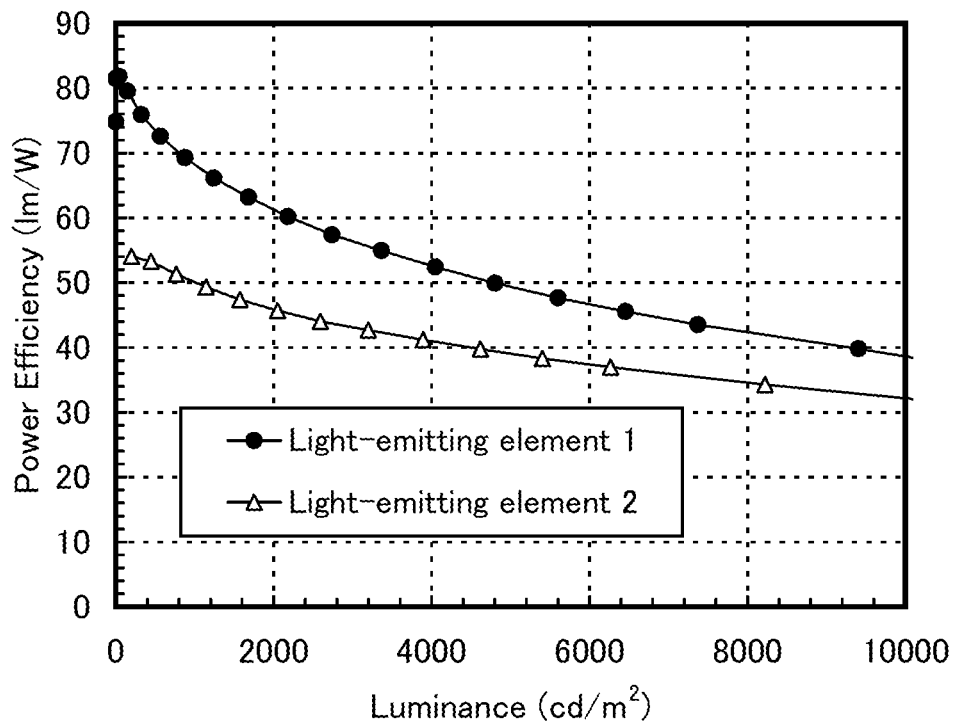
FIG. 15 shows power efficiency versus luminance characteristics of light-emitting elements of Example 2.
Figure 16:
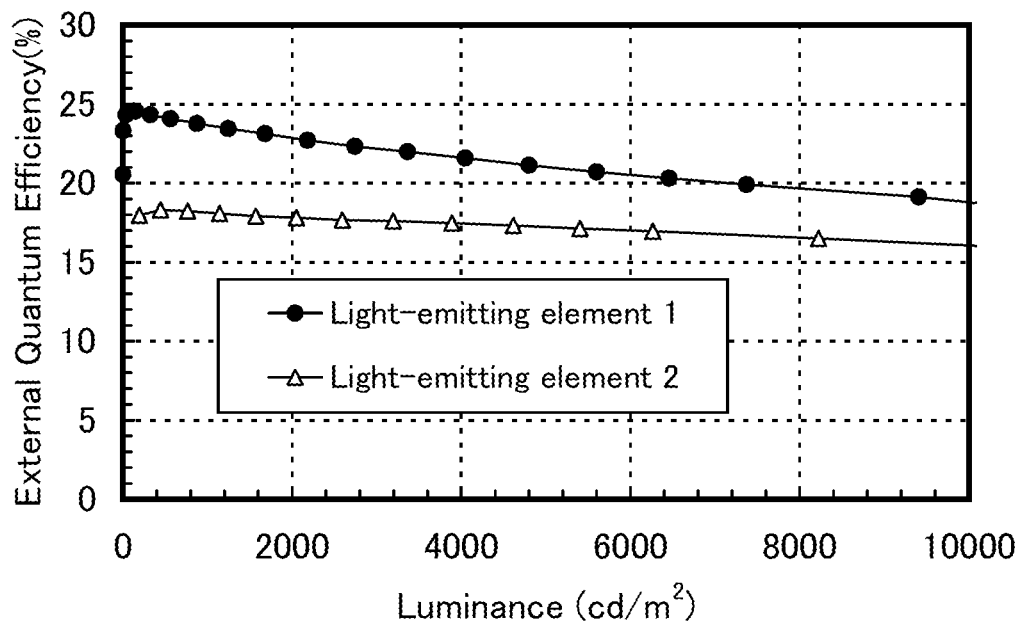
FIG. 16 shows external quantum efficiency versus luminance characteristics of light-emitting elements of Example 2.
Figure 17:
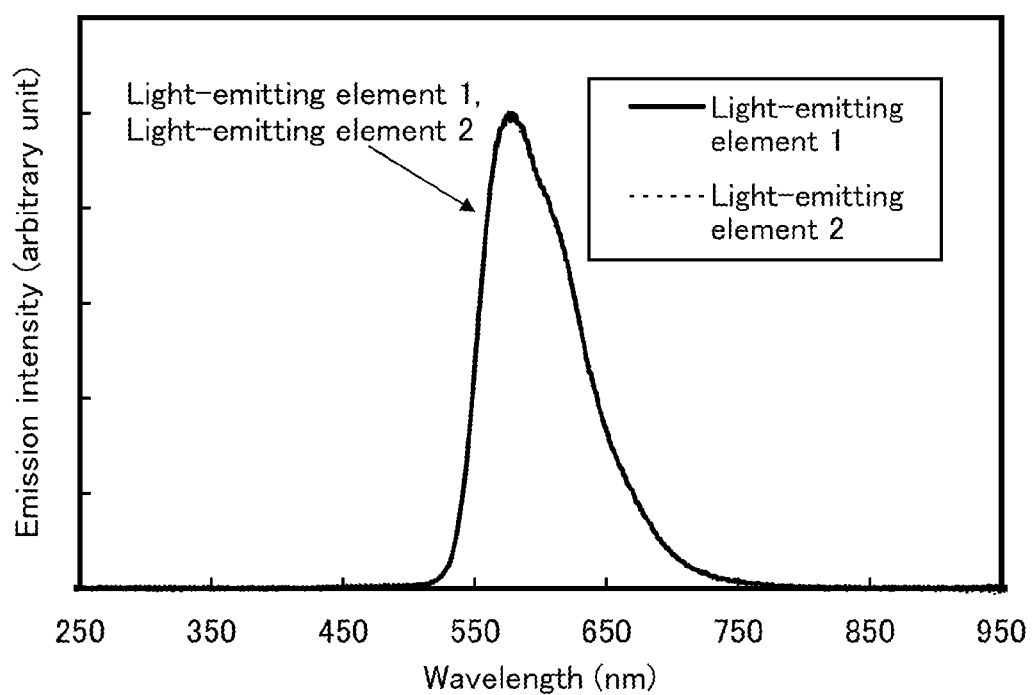
FIG. 17 shows an emission spectrum of light-emitting elements of Example 2.

FIG. 11 shows current efficiency versus luminance characteristics of the light-emitting elements 1 and 2. In FIG. 11, the horizontal axis represents luminance (cd/m$^2$) and the vertical axis represents current efficiency (cd/A). FIG. 12 shows luminance versus voltage characteristics. In FIG. 12, the horizontal axis represents voltage (V) and the vertical axis represents luminance (cd/m$^2$). FIG. 13 shows the current versus voltage characteristics. In FIG. 13, the horizontal axis represents voltage (V) and the vertical axis represents current (mA). FIG. 14 shows chromaticity coordinate versus luminance characteristics. In FIG. 14, the horizontal axis represents luminance (cd/m$^2$) and the vertical axis represents chromaticity coordinate (the x-coordinate or the y-coordinate). FIG. 15 shows power efficiency versus luminance characteristics. In FIG. 15, the horizontal axis represents luminance (cd/m$^2$) and the vertical axis represents power efficiency (lm/W). In addition, external quantum efficiency versus luminance characteristics are shown in FIG. 16. In FIG. 16, the horizontal axis represents luminance (cd/m$^2$) and the vertical axis represents external quantum efficiency (%). Further, Table 2 shows the voltage (V), current density (mA/cm$^2$), CIE chromaticity coordinates (x, y), luminance (cd/m$^2$), current efficiency (cd/A), power efficiency (lm/W), and external quantum efficiency (%) of each light-emitting element at a luminance of around 1000 cd/m$^2$.

the vertical axis represents emission intensity (arbitrary unit). As shown in FIG. 17, the emission spectrum of the light-emitting element 1 has a peak at 576 nm and the emission spectrum of the light-emitting element 2 has a peak at 578 nm. In addition, as shown in Table 2, the CIE chromaticity coordinates of the light-emitting element 1 were (x, y)=(0.55, 0.45) at a luminance of 870 cd/m$^2$ and the CIE chromaticity coordinates of the light-emitting element 2 were (x, y)=(0.54, 0.45) at a luminance of 1100 cd/m$^2$. It was found that the light-emitting elements 1 and 2 exhibited light emission from [Ir(mppr-Me)$_2$(dpm)].

From the above, it was found that 6mDBTPDBq-II had a high T1 level and was able to be favorably used as a host material in the case where a phosphorescent compound emitting at least orange light to light having a wavelength on a longer wavelength side than orange is used as a light-emitting substance.

As shown in FIG. 14, the light-emitting elements 1 and 2 show substantially no change in color over a range from low luminance to high luminance. It can be said from this result that the light-emitting elements 1 and 2 are elements having excellent carrier balance.

From the results in FIG. 11, FIG. 12, FIG. 13, FIG. 15, and FIG. 16, it was found that the light-emitting element 1 and the light-emitting element 2 each had low driving voltage. Moreover, it was also found that the light-emitting element 1 and the light-emitting element 2 each had high current efficiency, high external quantum efficiency, and high power efficiency. In particular, the light-emitting element 1 was shown to have higher current efficiency, higher external quantum efficiency, and higher power efficiency than the light-emitting element 2.

TABLE 2

| | Voltage (V) | Current density (mA/cm$^2$) | Chromaticity x | Chromaticity y | Luminance (cd/m$^2$) | Current efficiency (cd/A) | Power efficiency (lm/W) | External quantum efficiency (%) |
|---|---|---|---|---|---|---|---|---|
| Light-emitting element 1 | 3.0 | 1.3 | 0.55 | 0.45 | 870 | 66 | 69 | 24 |
| Light-emitting element 2 | 3.2 | 2.3 | 0.54 | 0.45 | 1100 | 50 | 49 | 18 |

FIG. 17 shows emission spectra of the light-emitting elements 1 and 2 which were obtained when a current of 0.1 mA was made to flow in the light-emitting elements 1 and 2. In FIG. 17, the horizontal axis represents wavelength (nm) and A factor in that can be considered as a material with a high hole-transport property such as an amine-based compound, which was contained in the light-emitting layer of the light-emitting element 1.

As described above, by using 6mDBTPDBq-II as a host material of a light-emitting layer, a light-emitting element having low driving voltage and high current efficiency was able to be fabricated. Further, it was found that emission efficiency of the light-emitting element was able to be higher when the host material was doped with a material having a higher hole-transport property.

Next, a reliability test of the light-emitting element 1 was carried out. In the reliability testing, the light-emitting element 1 was driven under the conditions where the initial luminance was set to 5000 cd/m$^2$ and the current density was constant.

The light-emitting element 1 kept 80% of the initial luminance after the driving for 82 hours.

From the above results, it was confirmed that a highly reliable element can be obtained by using 6mDBTPDBq-II as a host material of a light-emitting layer.

Example 3

In this example, a light-emitting element according to one embodiment of the present invention will be described referring to FIG. 6. Chemical formulae of materials used in this example are illustrated below. Note that the chemical formulae of the materials which are shown above are omitted.

[Chemical Formula 32]

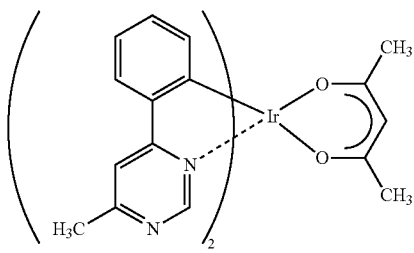

[Ir(mppm)$_2$(acac)]

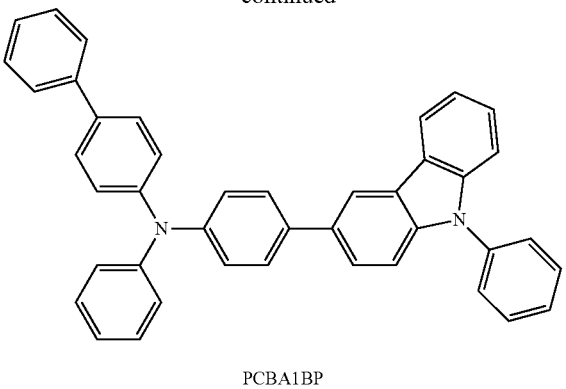

PCBA1BP

A method of fabricating a light-emitting element 3 of this example will be described below.

(Light-Emitting Element 3)

The components other than the light-emitting layer 1113 were formed in the same way as those of the light-emitting element 1. The light-emitting layer 1113 of the light-emitting element 3 is described below.

The light-emitting layer 1113 of the light-emitting element 3 was formed by co-evaporation of 6mDBTPDBq-II which was synthesized in Example 1, 4-phenyl-4'-(9-phenyl-9H-carbazol-3-yl)triphenylamine (abbreviation: PCBA1BP), and (acetylacetonato)bis(6-methyl-4-phenylpyrimidinato)iridium(III) (abbreviation: [Ir(mppm)$_2$(acac)]). The weight ratio of 6mDBTPDBq-II to PCBA1BP and [Ir(mppm)$_2$(acac)] was adjusted to 0.8:0.2:0.05 (=6mDBTPDBq-II:PCBA1BP:[Ir(mppm)$_2$(acac)]). The thickness of the light-emitting layer 1113 was set to 40 nm.

An element structure of the light-emitting element 3 which was obtained is shown in Table 3.

TABLE 3

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 3 | ITSO 110 nm | BPAFLP:MoOx (=4:2) 40 nm | BPAFLP 20 nm | 6mDBTPDBq-II:PCBA1BP:[Ir(mppm)$_2$(acac)] (= 0.8:0.2:0.05) 40 nm | 6mDBTPDBq-II 10 nm | BPhen 20 nm | LiF 1 nm | Al 200 nm |

In a glove box containing a nitrogen atmosphere, the light-emitting element 3 was sealed with a glass substrate so as not to be exposed to the air. Then, operation characteristics of the element were measured. Note that the measurements were carried out at room temperature (in the atmosphere kept at 25° C.).

Figure 18:
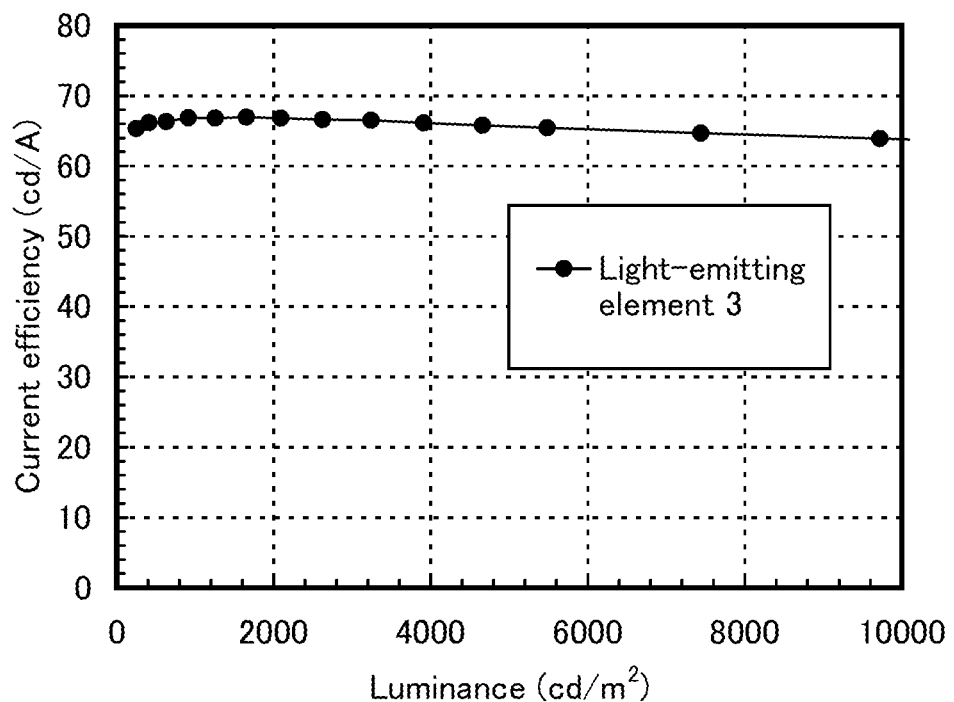
FIG. 18 shows current efficiency versus luminance characteristics of a light-emitting element of Example 3.
Figure 19:
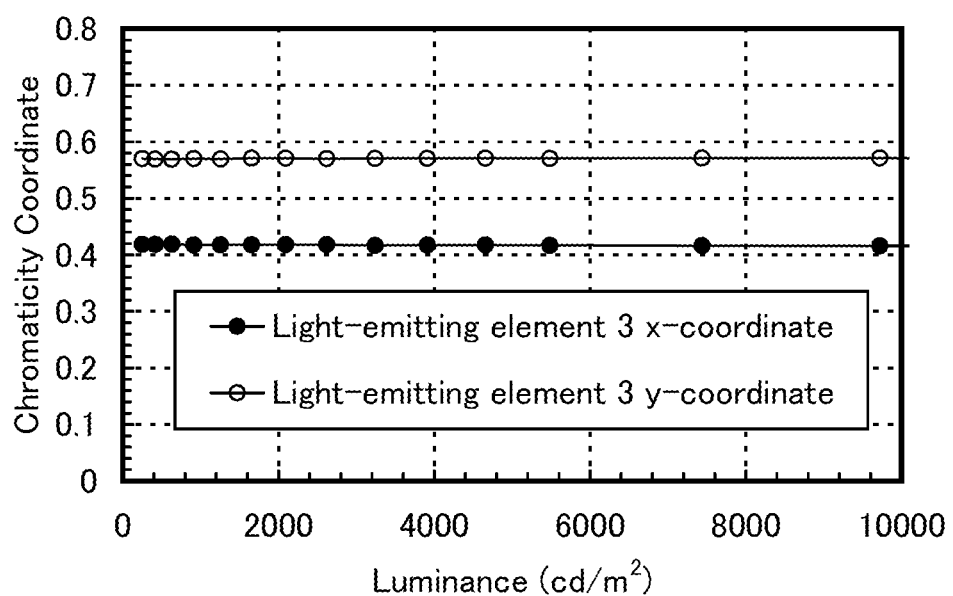
FIG. 19 shows chromaticity coordinate versus luminance characteristics of a light-emitting element of Example 3.
Figure 20:
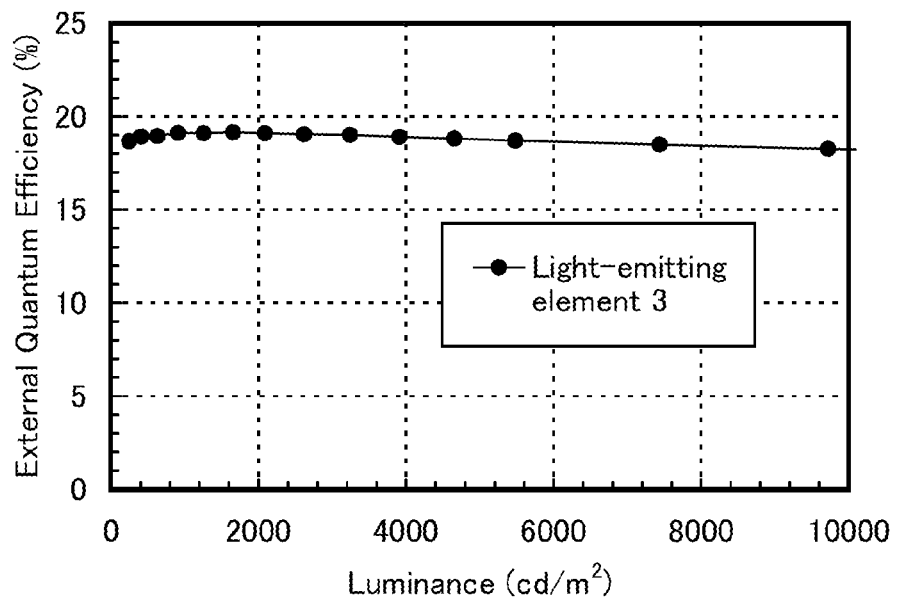
FIG. 20 shows external quantum efficiency versus luminance characteristics of a light-emitting element of Example 3.

FIG. 18 shows current efficiency versus luminance characteristics of the light-emitting element 3. In FIG. 18, the horizontal axis represents luminance (cd/m$^2$) and the vertical axis represents current efficiency (cd/A). FIG. 19 shows chromaticity coordinate versus luminance characteristics. In FIG. 19, the horizontal axis represents luminance (cd/m$^2$) and the vertical axis represents chromaticity coordinate (the x-coordinate or the y-coordinate). In addition, FIG. 20 shows external quantum efficiency versus luminance characteristics. In FIG. 20, the horizontal axis represents luminance (cd/m$^2$) and the vertical axis represents external quantum efficiency (%). Further, Table 4 shows the voltage (V), current density (mA/cm$^2$), CIE chromaticity coordinates (x, y), and current efficiency (cd/A) of the light-emitting element 3 at a luminance of 910 cd/m$^2$.

[Chemical Formula 33]

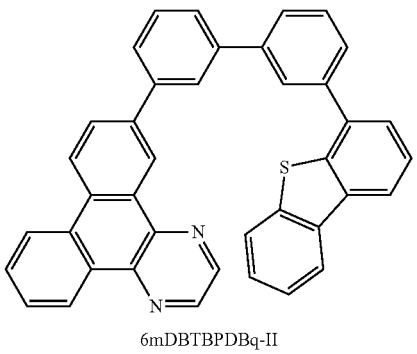

6mDBTBPDBq-II

TABLE 4

| | Voltage (V) | Current density (mA/cm$^2$) | Chromaticity x | Chromaticity y | Luminance (cd/m$^2$) | Current efficiency (cd/A) |
|---|---|---|---|---|---|---|
| Light-emitting element 3 | 3.2 | 1.4 | 0.42 | 0.57 | 910 | 67 |

Figure 21:
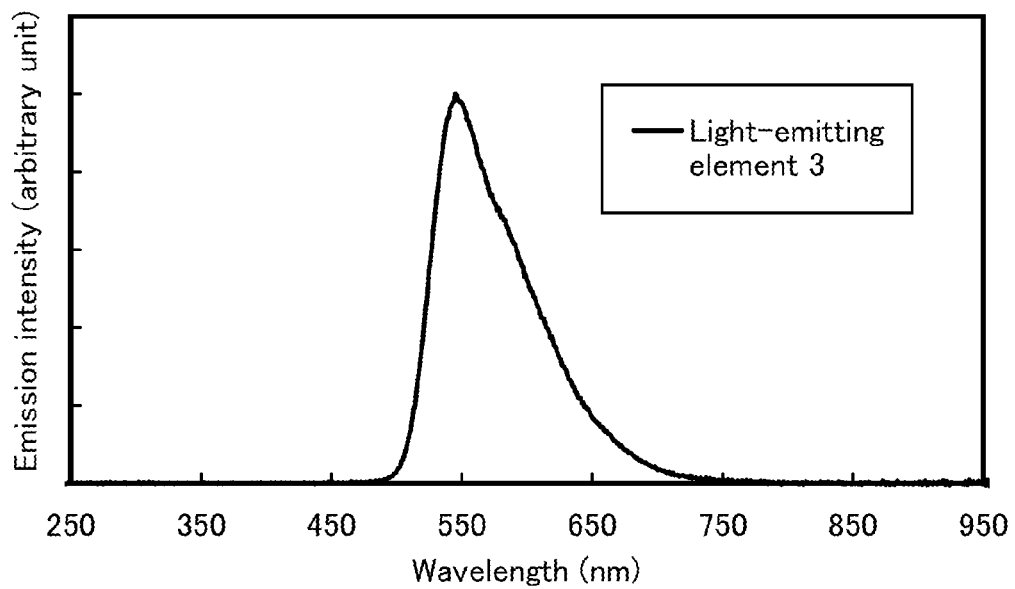
FIG. 21 shows an emission spectrum of a light-emitting element of Example 3.

FIG. 21 shows an emission spectrum of the light-emitting element 3 which was obtained when a current of 0.1 mA was made to flow in the light-emitting element 3. In FIG. 21, the horizontal axis represents wavelength (nm) and the vertical axis represents emission intensity (arbitrary unit). As shown in FIG. 21, the emission spectrum of the light-emitting element 3 has a peak at 545 nm. In addition, as shown in Table 4, the CIE chromaticity coordinates of the light-emitting element 3 were (x, y)=(0.42, 0.57) at a luminance of 910 cd/m$^2$. It was found that the light-emitting element 3 exhibited light emission from [Ir(mppm)$_2$(acac)].

From the above, it was found that 6mDBTPDBq-II had a high T1 level and was able to be favorably used as a host material in the case where a phosphorescent compound emitting at least yellow light to light having a wavelength on a longer wavelength side than yellow is used as a light-emitting substance.

As shown in FIG. 19, the light-emitting element 3 shows substantially no change in color over a range from low luminance to high luminance. It can be said from this result that the light-emitting element 3 is an element having excellent carrier balance.

From Table 4, FIG. 18, and FIG. 20, it was found that the light-emitting element 3 had high current efficiency and high external quantum efficiency. It was also found that the light-emitting element 3 had low driving voltage.

As described above, by using 6mDBTPDBq-II as a host material of a light-emitting layer, a light-emitting element having low driving voltage was able to be fabricated. In addition, current efficiency of the light-emitting element was able to be high.

Example 4

Synthesis Example 2

This example gives specific descriptions of a method of synthesizing 6-[3-(3'-dibenzothiophen-4-yl)biphenyl]dibenzo[f,h]quinoxaline (abbreviation: 6mDBTBPDBq-II) represented by the structural formula (105) in Embodiment 1. A structure of 6mDBTBPDBq-II is illustrated below.

A scheme of this synthesis example is illustrated in (C-1).

[Chemical Formula 34]

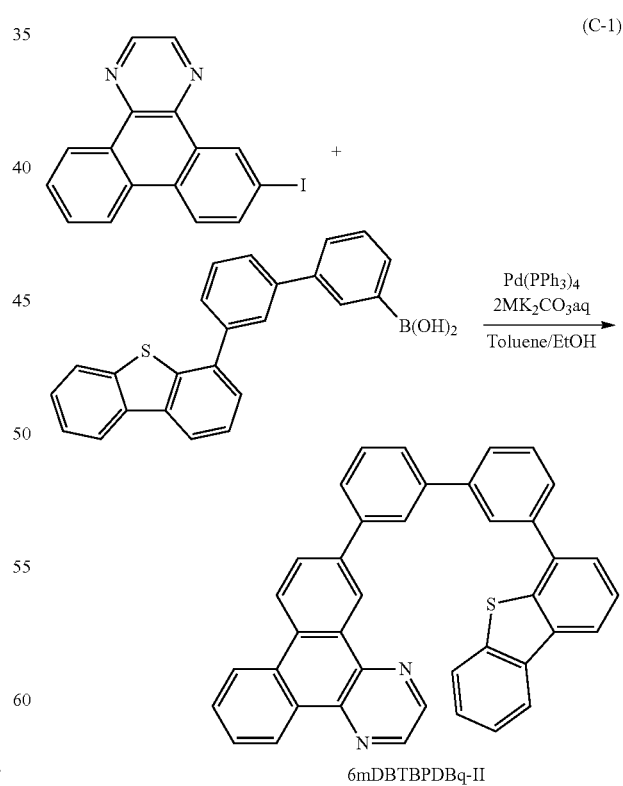

(C-1)

6mDBTBPDBq-II

In a 100 mL three-neck flask were put 0.9 g (2.6 mmol) of 6-iododibenzo[f,h]quinoxaline, 1.0 g (2.7 mmol) of 3-(3'-dibenzothiophen-4-yl)biphenylboronic acid, 30 mL of toluene, 3 mL of ethanol, and 4.0 mL of a 2M aqueous solution of potassium carbonate. This mixture was degassed by stirring under reduced pressure, and the air in the flask was replaced with nitrogen. To this mixture was added 62 mg (0.05 mmol) of tetrakis(triphenylphosphine)palladium(0). This mixture was stirred under a nitrogen stream at 80° C. for 18 hours. After a predetermined time elapsed, the solid precipitated in the system was collected by suction filtration. Water was added to this solid, and irradiation with ultrasonic waves was performed. A solid was collected by suction filtration. In a similar manner, ethanol was added to this solid, and irradiation with ultrasonic waves was performed. A solid was collected by suction filtration. A toluene solution of the obtained solid was suction-filtered through alumina and Celite (produced by Wako Pure Chemical Industries, Ltd., Catalog No. 531-16855), and the filtrate was concentrated to give a solid. Further, this solid was recrystallized from toluene to give 1.1 g of the object of the synthesis in 73% yield.

Nuclear magnetic resonance (NMR) spectroscopy identified the compound obtained in this synthesis example as 6-[3-(3'-dibenzothiophen-4-yl)biphenyl]dibenzo[f,h]quinoxaline (abbreviation: 6mDBTBPDBq-II), which was the object of the synthesis.

$^1$H NMR data of the obtained compound are as follows: $^1$H NMR (CDCl$_3$, 300 MHz): δ (ppm)=7.44-7.52 (m, 2H), 7.59-7.68 (m, 4H), 7.74-7.91 (m, 7H), 8.11-8.23 (m, 5H), 8.67 (d, J=7.5H, 1H), 8.73 (d, J=8.4 Hz, 1H), 8.91 (dd, J=9.0 Hz, 1.8 Hz, 2H), 9.24 (dd, J=6.0 Hz, 1.2 Hz, 1H), 9.56 (d=2.1 Hz, 1H).

Figure 23A:
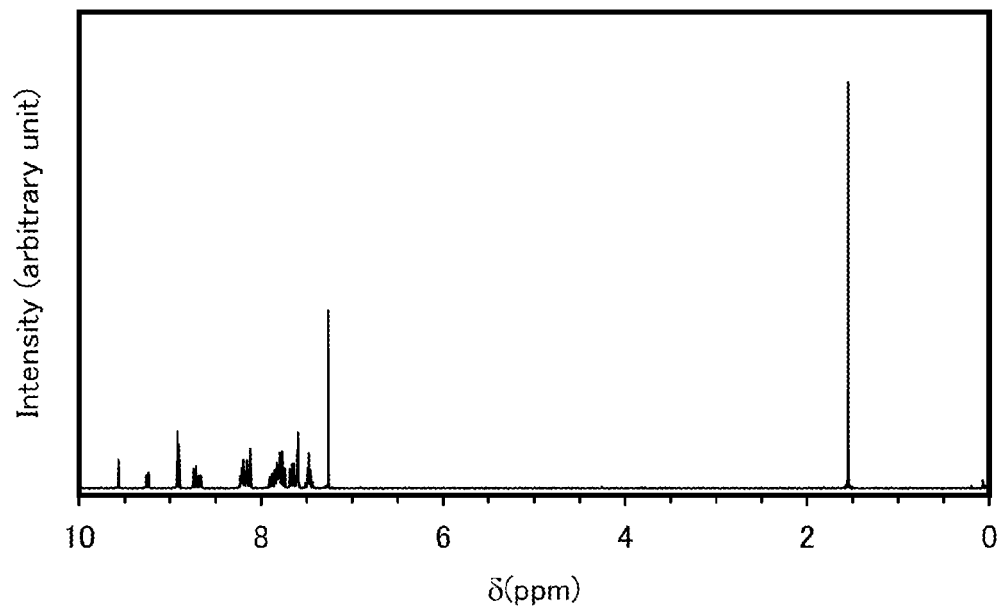
FIGS. 23A and 23B show $^1$H NMR charts of 6-[3-(3'-dibenzothiophen-4-yl)biphenyl]dibenzo[f,h]quinoxaline (abbreviation: 6mDBTBPDBq-II)
Figure 23B:
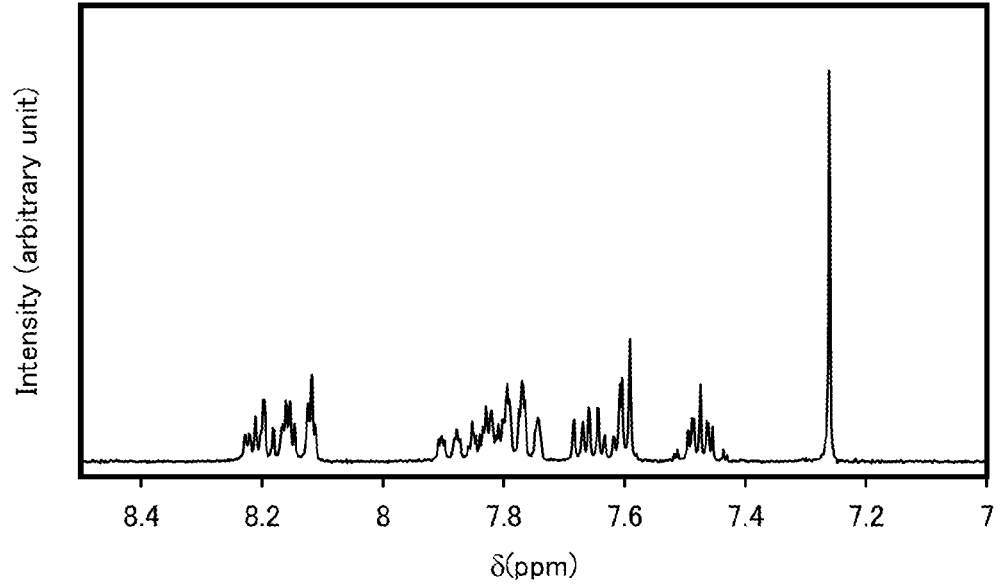

FIGS. 23A and 23B show the $^1$H NMR charts. Note that FIG. 23B is a chart showing an enlarged part of FIG. 23A in the range of 7.0 ppm to 8.5 ppm. The measurement results confirmed that the object of the synthesis, 6mDBTBPDBq-II, was obtained.

Figure 24A:
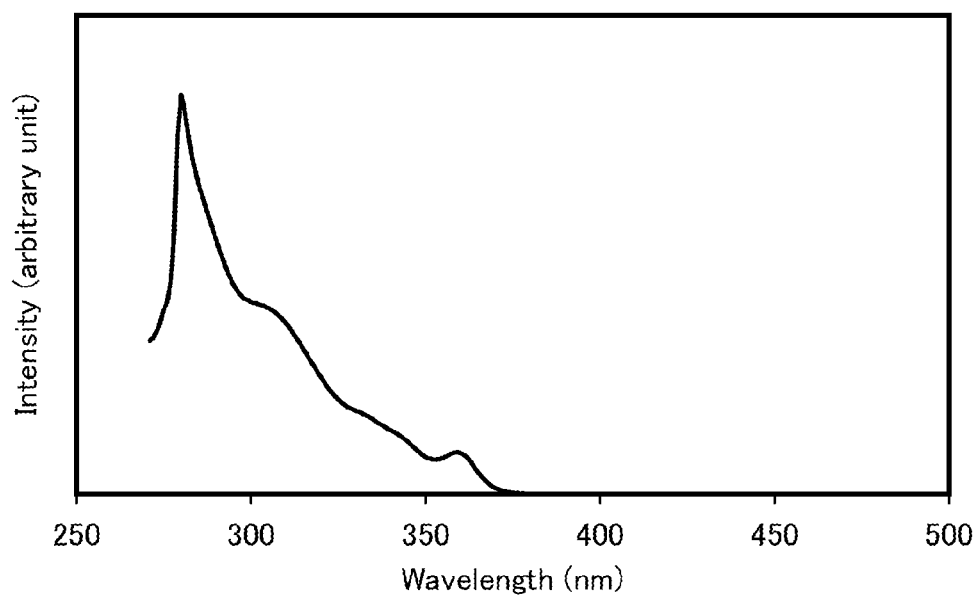
FIGS. 24A and 24B show respectively an absorption spectrum and an emission spectrum of 6mDBTBPDBq-II in a toluene solution of 6mDBTBPDBq-II.
Figure 24B:
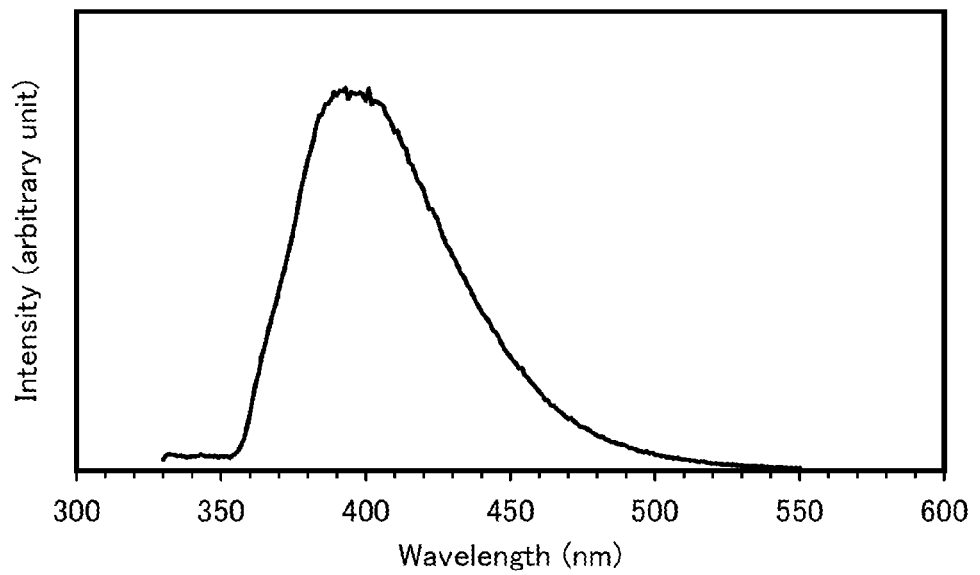
Figure 25A:
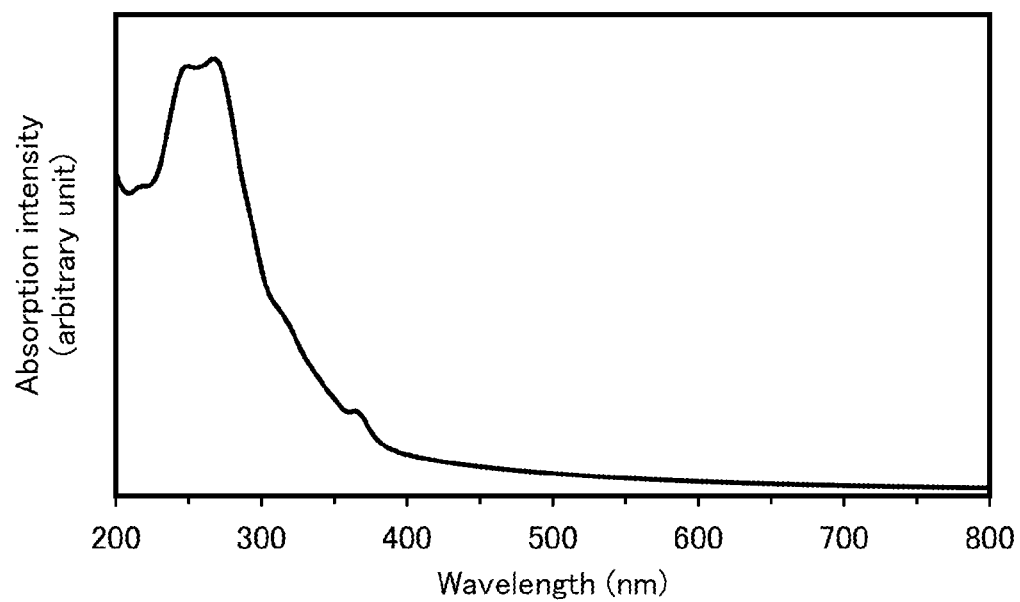
FIGS. 25A and 25B show respectively an absorption spectrum and an emission spectrum of a thin film of 6mDBTBPDBq-II.
Figure 25B:
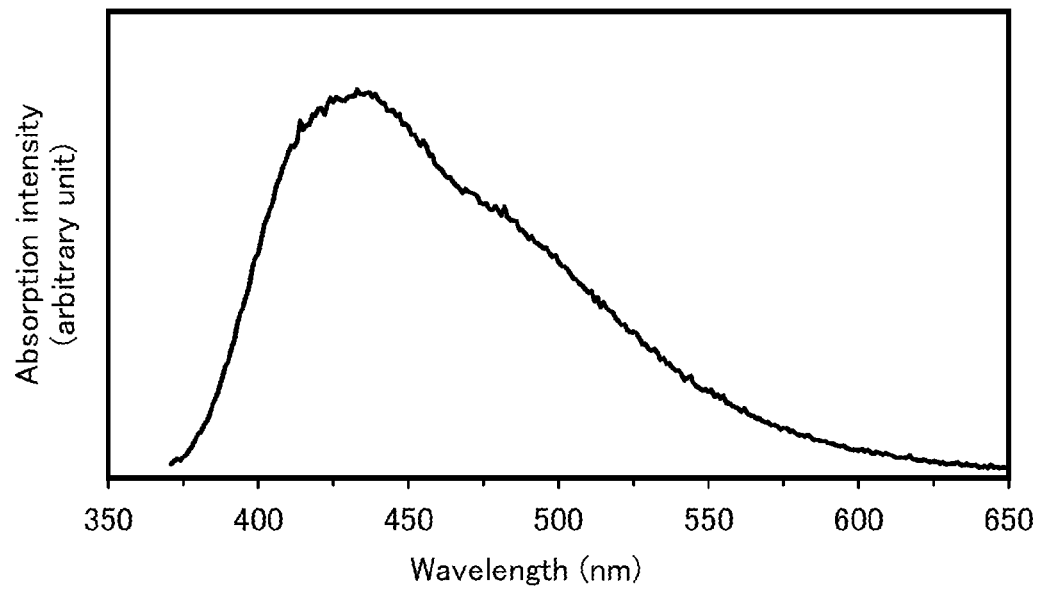

Further, FIG. 24A shows an absorption spectrum of 6mDBTBPDBq-II in a toluene solution of 6mDBTBPDBq-II, and FIG. 24B shows an emission spectrum thereof. FIG. 25A shows an absorption spectrum of a thin film of 6mDBTBPDBq-II, and FIG. 25B shows an emission spectrum thereof. The absorption spectrum was measured using an ultraviolet-visible spectrophotometer (V-550, produced by JASCO Corporation). The measurements were performed with samples prepared in such a way that the solution was put in a quartz cell and the thin film was obtained by evaporation onto a quartz substrate. The figures show the absorption spectrum of the solution which was obtained by subtracting the absorption spectra of quartz and toluene from the absorption spectra of quartz and the solution, and the absorption spectrum of the thin film which was obtained by subtracting the absorption spectrum of a quartz substrate from the absorption spectra of the quartz substrate and the thin film. In each of FIG. 24A and FIG. 25A, the horizontal axis represents wavelength (nm) and the vertical axis represents absorption intensity (arbitrary unit). In each of FIG. 24B and FIG. 25B, the horizontal axis represents wavelength (nm) and the vertical axis represents emission intensity (arbitrary unit). In the case of the toluene solution, an absorption peak was observed at around 359 nm, and an emission wavelength peak was 393 nm. In the case of the thin film, absorption peaks were observed at around 218 nm, 249 nm, 267 nm, 311 nm, and 364 nm, and emission wavelength peaks were 433 nm and 475 nm (at an excitation wavelength of 365 nm).

From emission wavelengths, it was found that 6mDBTBPDBq-II emitted blue to bluish purple light and thus was able to be used as a light-emitting material for blue to bluish purple light. Further, it was also found that 6mDBTBPDBq-II was able to be used as a host material of a fluorescent light-emitting material which emits light having a longer wavelength than light emitted by 6mDBTBPDBq-II.

Further, by measurement with a photoelectron spectrometer (AC-2, manufactured by Riken Keiki, Co., Ltd.) in the air, the ionization potential of 6mDBTBPDBq-II in the thin film was found to be 5.98 eV. As a result, the HOMO level was found to be −5.98 eV. The absorption edge was obtained from Tauc plot assuming direct transition with the absorption spectrum data of the thin film of 6mDBTBPDBq-II. The absorption edge was estimated as an optical energy gap, and the energy gap was 3.22 eV. From the obtained value of the energy gap and the HOMO level, the LUMO level was −2.76 eV.

Reference Example 1

An example of synthesis of (dipivaloylmethanato)bis(3,5-dimethyl-2-phenylpyrazinato)iridium(III) (abbreviation: [Ir(mppr-Me)$_2$(dpm)]) used in the example above will be described. The structure of [Ir(mppr-Me)$_2$(dpm)] is illustrated below.

[Chemical Formula 35]

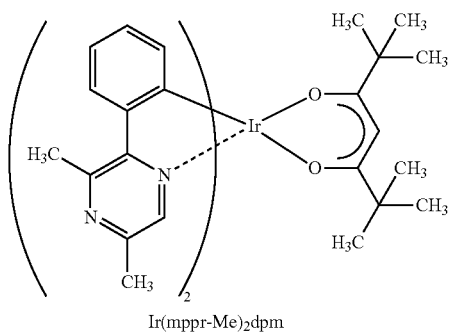

Ir(mppr-Me)$_2$dpm

First, 20 mL of 2-ethoxyethanol, 1.55 g of a dinuclear complex di-μ-chloro-bis[bis(3,5-dimethyl-2-phenylpyrazinato)iridium(III)] (abbreviation: [Ir(mppr-Me)$_2$Cl]$_2$), 0.8 ml of dipivaloylmethane, and 1.38 g of sodium carbonate were mixed. The mixture was irradiated with microwaves under argon bubbling for 30 minutes, whereby the mixture was reacted. After reaction, the reaction solution was cooled down to room temperature, and water was added thereto. This mixture solution was separated into an organic layer and an aqueous layer, and organic substances were extracted from the aqueous layer with dichloromethane. The organic layer was combined with the solution of the extracted organic substances, and the mixture was washed with water, followed by drying with anhydrous magnesium sulfate. After that, the mixture was gravity-filtered, and the filtrate was concentrated to be dried and hardened. This solid was recrystallized from a mixed solvent of dichloromethane and ethanol to give a red powder in a yield of 67%. A synthesis scheme is illustrated below. Note that the irradiation with microwaves was performed using a microwave synthesis system (Discover, produced by CEM Corporation). The synthesis scheme of this step is illustrated in the following (x-1).

[Chemical Formula 36]

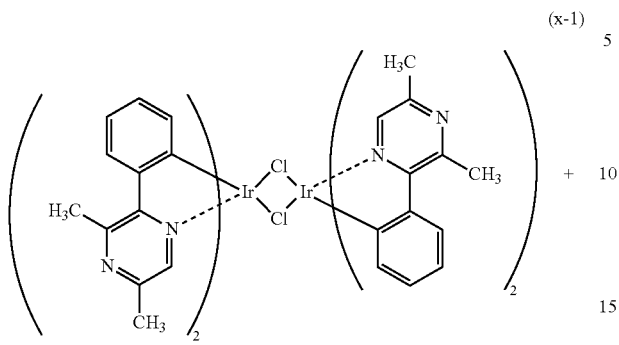

Ir(mppr-Me)₂dpm

Note that nuclear magnetic resonance (¹H NMR) spectroscopy identified this compound as an organometallic complex [Ir(mppr-Me)₂(dpm)], which was the object of the synthesis. The obtained ¹H NMR analysis results are shown below.

¹H NMR. δ (CDCl₃): 0.90 (s, 1H), 2.59 (s, 6H), 3.04 (s, 6H), 5.49 (s, 1H), 6.32 (dd, 2H), 6.70 (dt, 2H), 6.88 (dt, 2H), 7.86 (d, 2H), 8.19 (s, 2H).

Reference Example 2

An example of synthesis of (acetylacetonato)bis(6-methyl-4-phenylpyrimidinato)iridium(III) (abbreviation: [Ir(mppm)₂ (acac)]) used in the above example will be described. The structure of [Ir(mppm)₂(acac)] is illustrated below.

[Chemical Formula 37]

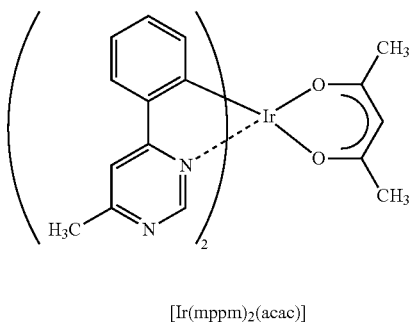

[Ir(mppm)₂(acac)]

Step 1: Synthesis of 4-Methyl-6-phenylpyrimidine (abbreviation: Hmppm)

First, in a recovery flask equipped with a reflux pipe were put 4.90 g of 4-chloro-6-methylpyrimidine, 4.80 g of phenylboronic acid, 4.03 g of sodium carbonate, 0.16 g of bis(triphenylphosphine)palladium(II)dichloride (abbreviation: Pd(PPh₃)₂Cl₂), 20 mL of water, and 10 mL of acetonitrile, and the air in the flask was replaced with argon. This reaction container was subjected to irradiation with microwaves (2.45 GHz, 100 W) for 60 minutes so that heating was performed. Here, in the flask were further put 2.28 g of phenylboronic acid, 2.02 g of sodium carbonate, 0.082 g of Pd(PPh₃)₂Cl₂, 5 mL of water, and 10 mL of acetonitrile, and the mixture was subjected to irradiation with microwaves (2.45 GHz, 100 W) for 60 minutes so that heating was performed. After that, water was added to this solution and an organic layer was subjected to extraction with dichloromethane. The solution of the obtained extract was washed with a saturated sodium carbonate aqueous solution, water, and saturated brine in this order and dried over magnesium sulfate. After the drying, the solution was filtered. The solvent of this solution was distilled off, and then the obtained residue was purified by silica gel column chromatography using dichloromethane and ethyl acetate as a developing solvent in a volume ratio of 9:1. As a result, a pyrimidine derivative Hmppm, which was the object of the synthesis, was obtained (orange oily substance, 46% yield). Note that for the microwave irradiation, a microwave synthesis system (Discover, produced by CEM Corporation) was used. A synthesis scheme (y-1) of Step 1 is illustrated below.

[Chemical Formula 38]

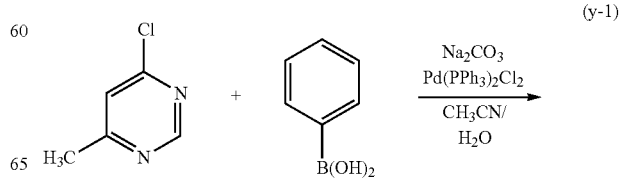

Step 2: Synthesis of Di-μ-chloro-bis[bis(6-methyl-4-phenylpyrimidinato)iridium(III)] (abbreviation: [Ir(mppm)₂Cl]₂)

Next, in a recovery flask equipped with a reflux pipe were put 15 mL of 2-ethoxyethanol, 5 mL of water, 1.51 g of Hmppm obtained in Step 1 above, and 1.26 g of iridium chloride hydrate (IrCl₃·H₂O), and the air in the flask was replaced with argon. After that, irradiation with microwaves (2.45 GHz, 100 W) was performed for one hour to cause a reaction. After the solvent was distilled off, and the obtained residue was washed with ethanol and filtered to give a dinuclear complex [Ir(mppm)₂Cl]₂ was obtained (dark green powder, 77% yield). A synthesis scheme (y-2) of Step 2 is illustrated below.

[Chemical Formula 39]

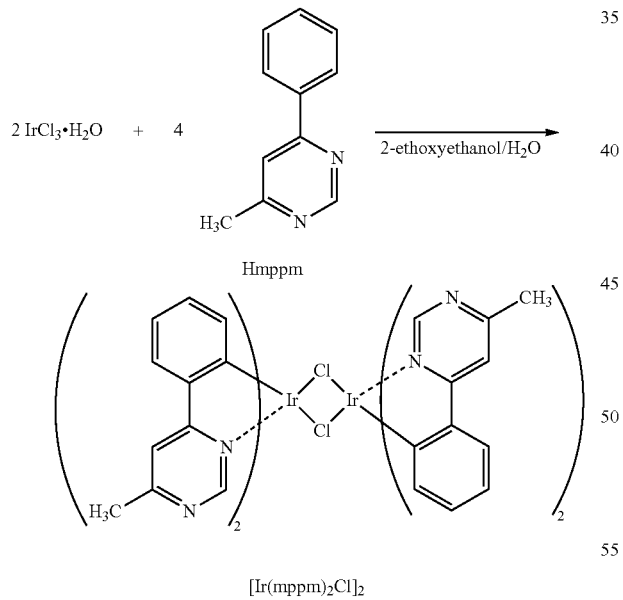

Step 3: Synthesis of (Acetylacetonato)bis(6-methyl-4-phenylpyrimidinato)iridium(III) (abbreviation: [Ir(mppm)₂(acac)])

Furthermore, in a recovery flask equipped with a reflux pipe were put 40 mL of 2-ethoxyethanol, 1.84 g of the dinuclear complex [Ir(mppm)₂Cl]₂ obtained in Step 2 above, 0.48 g of acetylacetone, and 1.73 g of sodium carbonate, and the air in the flask was replaced with argon. After that, irradiation with microwaves (2.45 GHz, 100 W) was performed for 60 minutes to cause a reaction. The solvent was distilled off, the obtained residue was dissolved in dichloromethane, and filtration was performed to remove an insoluble portion. The obtained filtrate was washed with water and then with saturated brine, and was dried over magnesium sulfate. After the drying, the solution was filtered. The solvent of this solution was distilled off, and then the obtained residue was purified by silica gel column chromatography using dichloromethane and ethyl acetate in a volume ratio of 4:1 as a developing solvent. After that, recrystallization was carried out with a mixed solvent of dichloromethane and hexane to give a yellow powder that was the object of the synthesis (44% yield). A synthesis scheme (y-3) of Step 3 is illustrated below.

[Chemical Formula 40]

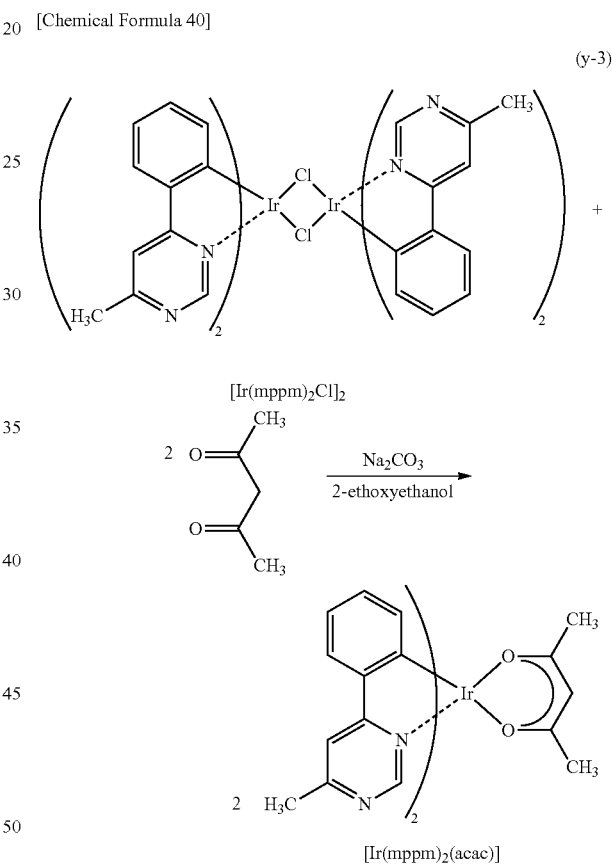

The results of nuclear magnetic resonance (¹H NMR) spectroscopy, by which the yellow powder obtained in Step 3 above was analyzed, are shown below. The results show that [Ir(mppm)₂(acac)] was obtained.

¹H NMR. δ (CDCl₃): 1.78 (s, 6H), 2.81 (s, 6H), 5.24 (s, 1H), 6.37 (d, 2H), 6.77 (t, 2H), 6.85 (t, 2H), 7.61-7.63 (m, 4H), 8.97 (s, 2H).

This application is based on Japanese Patent Application serial No. 2011-020124 filed with the Japan Patent Office on Feb. 1, 2011 and Japanese Patent Application serial No. 2011-181469 filed with the Japan Patent Office on Aug. 23, 2011, the entire contents of which are hereby incorporated by reference.

What is claimed is:

1. A heterocyclic compound represented by a general formula (G1),

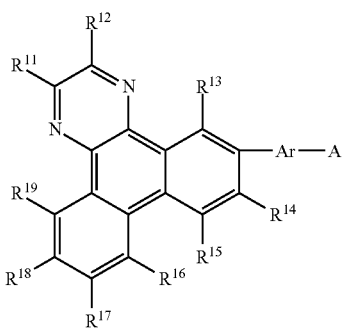

(G1)

wherein A represents a substituted or unsubstituted dibenzothiophenyl group or a substituted or unsubstituted dibenzofuranyl group, a substituent of the substituted dibenzothiophenyl group and the substituted dibenzofuranyl group being any of an alkyl group having 1 to 4 carbon atoms and an aryl group having 6 to 14 carbon atoms, wherein $R^{11}$ to $R^{19}$ separately represent any of hydrogen, an alkyl group having 1 to 4 carbon atoms, and an aryl group having 6 to 14 carbon atoms, and wherein Ar represents a substituted or unsubstituted arylene group having 6 to 13 carbon atoms, a substituent of the substituted arylene group being any of an alkyl group having 1 to 4 carbon atoms and an aryl group having 6 to 14 carbon atoms.

2. The heterocyclic compound according to claim 1, wherein Ar is a biphenyldiyl group.

3. The heterocyclic compound according to claim 1, wherein Ar is a phenylene group.

4. The heterocyclic compound according to claim 1, wherein Ar is an m-phenylene group.

5. A heterocyclic compound represented by a general formula (G2-1),

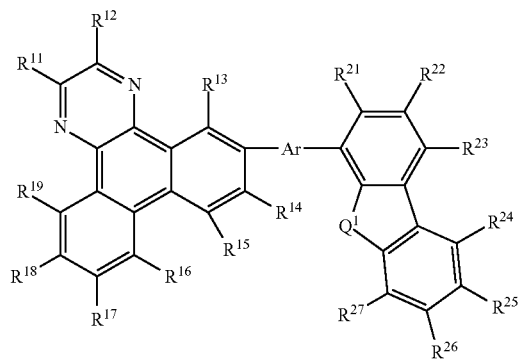

(G2-1)

wherein $Q^1$ represents a sulfur atom or an oxygen atom,
wherein $R^{11}$ to $R^{19}$ and $R^{21}$ to $R^{27}$ separately represent any of hydrogen, an alkyl group having 1 to 4 carbon atoms, and an aryl group having 6 to 14 carbon atoms, and wherein Ar represents a substituted or unsubstituted arylene group having 6 to 13 carbon atoms, a substituent of the substituted arylene group being any of an alkyl group having 1 to 4 carbon atoms, and an aryl group having 6 to 14 carbon atoms.

6. The heterocyclic compound according to claim 5, wherein Ar is a biphenyldiyl group.

7. The heterocyclic compound according to claim 5, wherein Ar is a phenylene group.

8. The heterocyclic compound according to claim 5, wherein Ar is an m-phenylene group.

9. A heterocyclic compound represented by a general formula (G2-3),

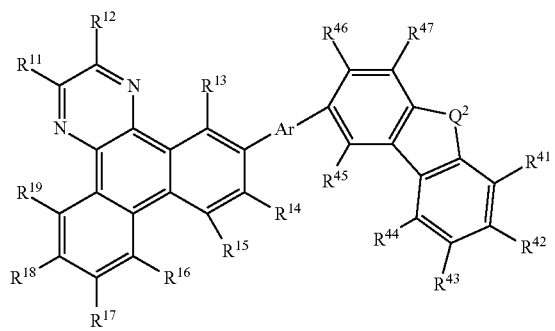

(G2-3)

wherein $Q^2$ represents a sulfur atom or an oxygen atom,
wherein $R^{11}$ to $R^{19}$ and $R^{41}$ to $R^{47}$ separately represent any of hydrogen, an alkyl group having 1 to 4 carbon atoms, and an aryl group having 6 to 14 carbon atoms, and wherein Ar represents a substituted or unsubstituted arylene group having 6 to 13 carbon atoms, a substituent of the substituted arylene group being any of an alkyl group having 1 to 4 carbon atoms, and an aryl group having 6 to 14 carbon atoms.

10. The heterocyclic compound according to claim 9, wherein Ar is a biphenyldiyl group.

11. The heterocyclic compound according to claim 9, wherein Ar is a phenylene group.

12. The heterocyclic compound according to claim 9, wherein Ar is an m-phenylene group.

13. A heterocyclic compound represented by a general formula (G3-1),

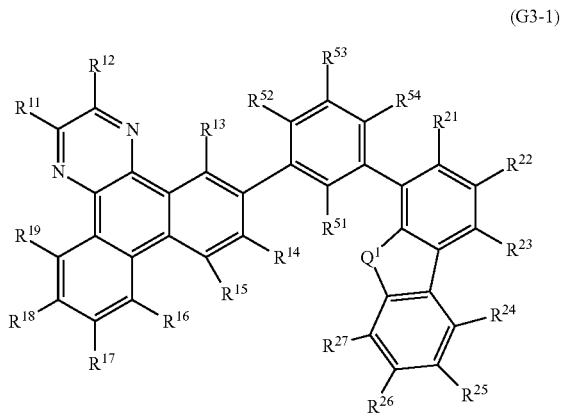

(G3-1)

wherein $Q^1$ represents a sulfur atom or an oxygen atom, and wherein $R^{11}$ to $R^{19}$, $R^{21}$ to $R^{27}$, and $R^{51}$ to $R^{54}$ separately represent any of hydrogen, an alkyl group having 1 to 4 carbon atoms, and an aryl group having 6 to 14 carbon atoms.

14. A heterocyclic compound represented by a general formula (G3-3),

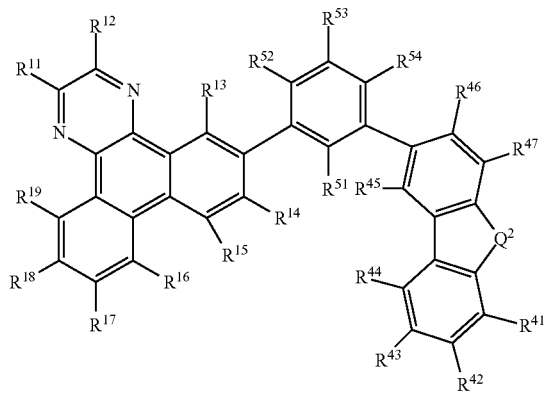

(G3-3)

wherein $Q^2$ represents a sulfur atom or an oxygen atom, and wherein $R^{11}$ to $R^{19}$, $R^{41}$ to $R^{47}$, and $R^{51}$ to $R^{54}$ separately represent any of hydrogen, an alkyl group having 1 to 4 carbon atoms, and an aryl group having 6 to 14 carbon atoms.

15. A light-emitting element comprising the heterocyclic compound according to claim 1.

16. A light-emitting device comprising the light-emitting element according to claim 15.

17. An electronic device comprising the light-emitting element according to claim 15.

18. A lighting device comprising the light-emitting element according to claim 15.

19. The heterocyclic compound according to claim 5, wherein the heterocyclic compound is represented by a chemical formula (101) or (107)

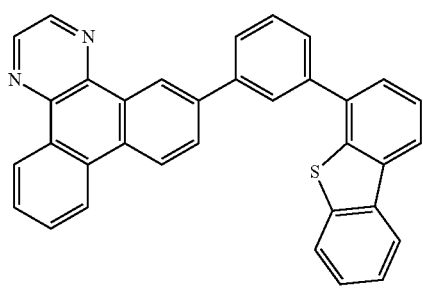

(101)

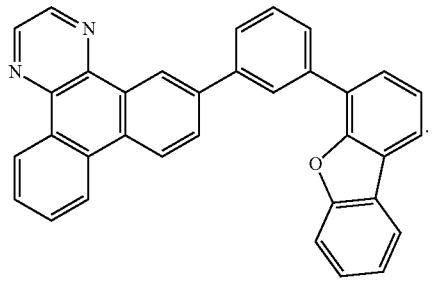

(107)

20. The heterocyclic compound according to claim 5, wherein the heterocyclic compound is represented by a chemical formula (105) or (111)

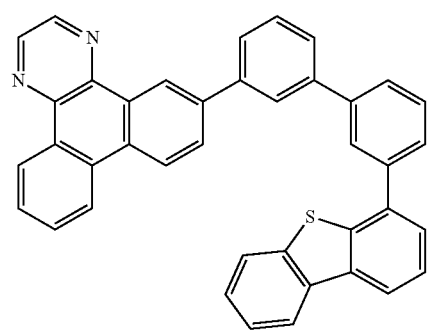

(105)

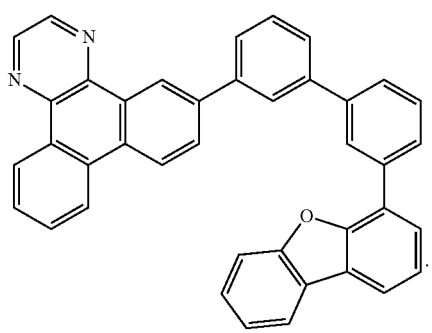

(111)

21. The heterocyclic compound according to claim 5, wherein the heterocyclic compound is represented by a chemical formula (125)

(125)
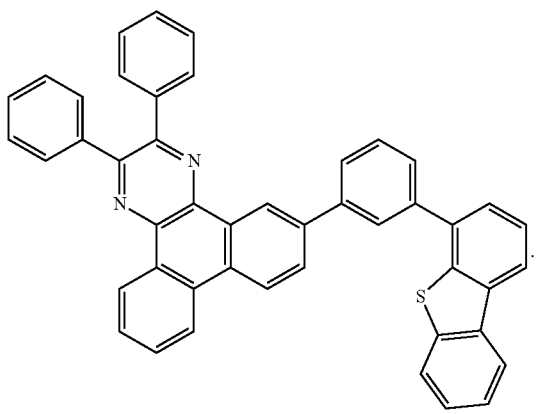
22. The heterocyclic compound according to claim 5, wherein the heterocyclic compound is represented by a chemical formula (128)
(128)
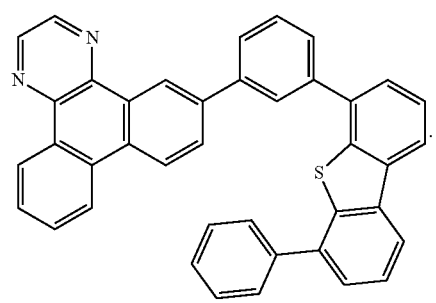
23. The heterocyclic compound according to claim 5, wherein the heterocyclic compound is represented by a chemical formula (129)
(129)
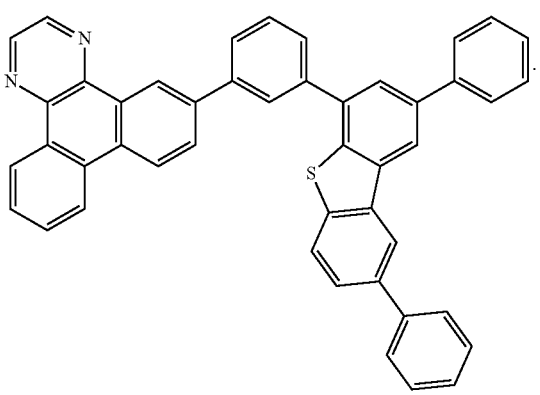
* * * * *